(12) United States Patent
Barton et al.

(10) Patent No.: US 7,622,302 B1
(45) Date of Patent: Nov. 24, 2009

(54) PROCESS FOR IMPROVING THE MANUFACTURE OF CLAVAMS E.G. CLAVULANIC ACID

(75) Inventors: Barry Barton, Worthing (GB); Alison Michelle Griffin, Worthing (GB); Susan Jensen, Edmonton (CA); Annie Wong, Edmonton (CA)

(73) Assignees: Glaxo Group Limited, Middlesex (GB); The Governors of the University of Alberta, Edmonton, Alberta (CA)

( * ) Notice: Subject to any disclaimer, the term of this patent is extended or adjusted under 35 U.S.C. 154(b) by 186 days.

(21) Appl. No.: 10/552,571

(22) PCT Filed: Apr. 13, 2004

(86) PCT No.: PCT/EP2004/004001

§ 371 (c)(1),
(2), (4) Date: Oct. 11, 2005

(87) PCT Pub. No.: WO2004/092389

PCT Pub. Date: Oct. 28, 2004

(30) Foreign Application Priority Data

Apr. 15, 2003 (GB) ................................ 0308696.4

(51) Int. Cl.
C12N 15/74 (2006.01)
(52) U.S. Cl. .................................................... 435/471
(58) Field of Classification Search ........................ None
See application file for complete search history.

(56) References Cited

U.S. PATENT DOCUMENTS 4,202,819 A    5/1980   Kellett et al. ............. 260/245.3

FOREIGN PATENT DOCUMENTS

| CA | 2108113 | 4/1995 |
|---|---|---|
| EP | 0 550549 | 9/1990 |
| ES | 550549 | 5/1987 |
| JP | 53-104796 | 9/1978 |
| WO | WO98/33896 | 8/1998 |
| WO | WO00/03581 | 1/2000 |
| WO | WO01/30977 | 5/2001 |
| WO | WO03/040372 | 5/2003 |

OTHER PUBLICATIONS

Tahlan et al. (Antimicrobial Agents and Chemotherapy, Mar. 2004; 48(3): 930-939).*
Liras P., et al., "Clavulanic acid, a β-lactamase inhibitor: biosynthesis and molecular genetics," *Applied Microbiology and Biotechnology*, Springer Verlag Berlin, Germany (2000) 54(4):467-475.
Mosher R., et al., "Genes Specific for the Biosynthesis of Clavam Metabolites Antipodal to Clavulanic Acid are Clustered with the Gene for Clavaminate Synthase 1 in *Streptomyces clavuligerus,*" *Antimicrobial Agents and Chemotherapy, American Society for Microbiology*, Washington, DC (May 1999) 43(5):1215-1224.

A.L. Demain, "Biosynthesis and Regulation of Beta-Lactam Antibiotics", *50 Years of Penicillin Applications, History & Trends* (1990).
Townsend, et al., "Biosynthesis of clavulanic Acid: Origin of the $C^3$ Unit," *J. Am. Chem. Soc.*, 107(4):1066-1068 (1985).
Valentine, et al., "Evidence that Arginine is a Later Metabolic Intermediate than Ornithine in the Biosyntheis of Clavulanic Acid by *Streptomyces clavuligerus,*" *J. Chem. Soc. Chem. Comm.*, 15:1210-1211 (1993).
Janc, et al., "Emerging Evidence for a Shared Biosynthetic Pathway Among Clavulanic Acid and the Structurally Diverse Clavam Metabolites," *Bioorg. Med. Chem. Lett.*, 3:2313-2316 (1993).
Rohl, et al., "Biological properties and mode of action of clavams," *Arch. Microbiol.*, 147:315-320 (1987).
Aidoo, et al., "Cloning, sequencing and disruption of a gene from *Streptomyces clavuligerus* involved in clavulanic acid biosynthesis," *Gene*, 147:41-46 (1994).
Sambrook, et al., *Molecular Cloning: A Laboratory Manual, 2nd Edition*. Cold Spring Harbor Laboratory, Cold Spring Harbor, NY (1989).
"Postassium Clavulanate," *British Pharmacopoeia* (1993); Addendum (1994) pp. 1362-1363.
"Clavulanate Potassium," *British Pharmacopoeia Official Monographs, USP* 23 NF18 pp. 384-385 (1985).
Hopwood, et al., *Genetic Manipulation of Streptomyces. A Cloning Manual* (1985).
Stahl, et al., "Development and Application of Nucleic Acid Probes," *Nucleic Acid Techniques in Bacterial Systematics.* Ed. E. Stackebrandt & M. Goodfellow. Toronto: John Wiley & Sons, pp. 204-248 (1991).
Doran, et al., "Isolation and Characterization of a β-Lactamase-Inhibitory Protein from *Streptomyces clavuligerus* and Cloning and Analysis of the Corresponding Gene," *J. Bacteriol.* 172(9):4909-4918 (1990).
Vieira, et al., "Production of Single-Stranded Plasmid DNA," *Methods Enzymol.*, 153: 3-11 (1987).
Sanger, et al., "DNA Sequencing with Chain-terminating Inhibitors," *Proc. Natl. Acad. Sci. USA*, 74: 5463-5467 (1977).
Ward, et al., "Construction and Characterisation of a Series of Multi-Copy Promoter-Probe Plasmid Vectors for *Streptomyces* Using the Aminoglycoside Phosphotransferase Gene fro Tn5 as Indicator," *Mol. Gen. Genet.* 203: 468-478 (1986).
Pruess, et al.,"A New Clavam Antibiotic from *Streptomyces clavuligerus,*" *Journal of Antibiotics*, XXXVI(3): 208-212 (Mar. 1983).
Paradkar, et al., "Functional analysis of the Gene Encoding the Clavaminate Synthase 2 Isoenzyme Involved in Clavulanic Acid Biosynthesis in *Streptomyces clavuligerus,*" *Journal of Bacteriology*, 177: 1307-1314 (1995).
Hodgson, J.E. et al., "Clavulanic Acid Biosynthesis in *Streptomyces clavuligerus*: Gene Cloning and Characterization," *Gene*, (1995) vol. 166, pp. 49-55.

(Continued)

*Primary Examiner*—Janet L. Epps-Smith
*Assistant Examiner*—Scott Long
(74) *Attorney, Agent, or Firm*—Andrea V. Lockenour; William T. Han; Sherry M. Knowles

(57) ABSTRACT

New processes for improving the manufacture of clavams e.g. clavulanic acid. Novel DNA sequences and new microorganisms capable of producing increased amounts of clavulanic acid are also disclosed.

2 Claims, 13 Drawing Sheets

OTHER PUBLICATIONS

Busby, R.W., "Expression and Purification of Two Isozymes of Clavaminate Synthase and Initial Characterization of the Iron Binding Site," *J. Biological Chem.*, (1995), vol. 270(9), pp. 4262-4269.

Brown, D. et al., "Structures of Three Novel β-lactams Isolated from *Streptomyces clavuligerus*," J.C.S. Chem. Comm., (1979), pp. 282-283.

Marsh, E.N. et al., "Two Isozymes of Clavaminate Synthase Central to Clavulanic Acid Formation: Cloning and Sequencing of Both Genes from *Streptomycs clavuligerus*," *Biochemistry*, (1992), vol. 31, pp. 12648-12657.

Elson, et al., "Studies on the Biosynthesis of Clavulanic Acid." *J. Antibiotics*, XXXI(6): 568 (1978).

Evans, R. H. et al., "Ro 22-5417, A New Clavam Antibiotic from *Streptomyces clavuligerus* II. Fermentation, Isolation and Structure" *J. Antiobiotics*, (1983), vol. 36(3), pp. 213-216.

Muller, J-C. et al, "Ro 22-5417, A New Clavam Antibiotic from *Streptomyces clavuligerus* III Absolute Stereochemistry," *J. Antiobiotics*, (1983), vol. 36(3), pp. 216-224.

King, H.D. et al., "Clavamycins, New Clavam Antibiotics from Two Variants of *Streptomyces hygroscopicus* I. Taxonomy of the Producing Organisms, Germentation, and Biological Activities," *J. Antiobiotics*, (1986), vol. 39(4), pp. 510-515.

Janc, J.W. et al., "Purification and Characterizatgion of Clavaminate Synthase from *Streptomyces antibioticus*," *J. Biological Chem.*, (1995), vol. 270(10), pp. 5399-5404.

Iwata-Reuly, D. and C. A. Townsend, "Common Origin of Clavulanic Acid and Other Clavam Metabolites in *Streptomyces*," *J. Am. Chem. Soc.*, (1992), vol. 114, pp. 2762-2763.

Paradkar, A. S. and S. E. Jensen, "Functional Analysis of the Gene Encoding the Clavaminate Synthase 2 Isoenzyme Involved in Clavulanic Acid Biosynthesis in *Streptomyces clavuligerus*," *J. Bacteriology*, (1995), vol. 177(5), pp. 1307-1314.

Baldwin, J. E. et al., "Enzymes of Valcalavam Biosynthesis," *Tetrahedron Letters*, (1994), vol. 35(17), pp. 2783-2786.

Egan, L.A. et al., "Probable Role of Clavaminic Acid as the Terminal Intermediate in the Common Pathway to Clavulanic Acid and the Antipodal Clavam Metabolites," *J. Am. Chem. Soc.*, (1997), vol. 119, pp. 2348-2355.

* cited by examiner

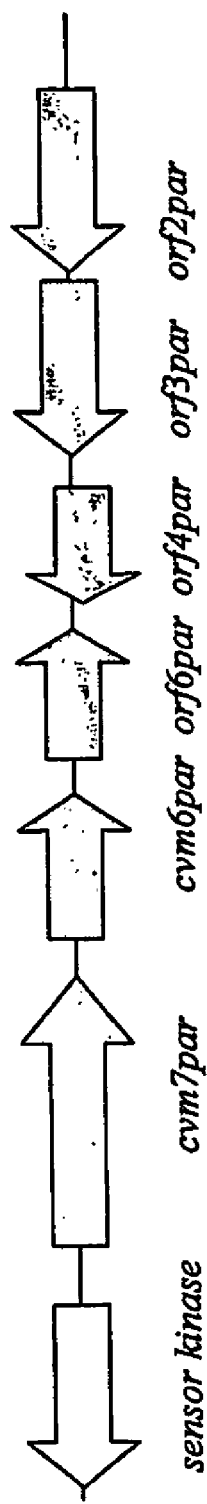
Figure 1. Diagram of the paralogue cluster

**Fig.2 Orientation of *cvm7* to published cvm cluster**
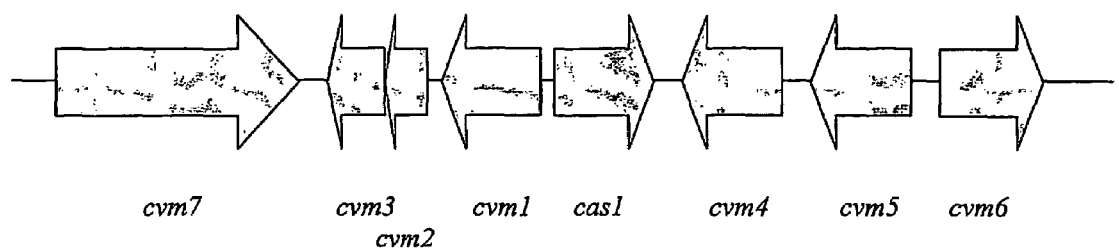

Figure 3. Annotated sequence of the paralogue cluster

Figure 3 Continued

```
1281 gatgccggtg gccacgaggt cggtgaaacc ggccagccgg tcctcggtgt cggcgggcag cggttccgcg gtcagcgaga 1360
1361 tgccatcat cacgccccac agccgtccct cgacgttgat cggcacgccg acgaccgaac cGAAGCCGGC CGCCCTGGCG 1440
1441 AAGTCGGCGG GTGCCCCGGA CGACTCGGCG GCCGTCGTCG CCGGCCCGTC CGGCCCCGTG TCGGACACCA GCGTCACCAC 1520
1521 GTTCCGGCCG TCGGGGTCCA CCCGGGTGCC GATGGGAAAG AGCGGGCCGT GCAGACTTCT GGACCCAGCC CCGACGGGCG 1600
1601 TCGCCATGCC GTCCGGATCG AGCCTGATGA TTCCGGTCAC ATCGTTGCCG AGCAGTTCTC CGACTTCGGC GGCGACCGTC 1680
                                                                                       start
1681 GCGAACATCT GTTCCGGTGG GGTGGCCCTG GCCACCAGGG TCGCCACCCG TGGAGTGCC GCCCGCTCCT CGACGATCTG 1760
sensor kinase →
1761 TTCGCACGAC ACGACCGCTG CCAGG CCCC CTACCCGCCC GATGACGCCC GCATACCGGG TATCACGGCA CATCAGCATG 1840
1841 ACGTCCGCCG TGAACGCCCG CCGTCTTCCT CCGGTCCGCC TCAACGTGGC CCGCCGGAGT CGCCCGGCCG AACGGCGGGA 1920
1921 CCGTCTTCCT CCGGTCCGCC GGTTGGTGGG AAGGGATGTT GGCCGCTGGC TGACCTCGGG AGTTTGCAGC TAGCTGGAAT 2000
2001 CAGCGGTTCG GGTTGGTGGG AAGGGATGTT GGCCGCTGGC AAGCCGATCG CGGGTTCTCC ACGGGGGAGA GATCCGCGAA 2080
2081 TGCGTCGCGG AGAGTCGGTC CGCTTCCCCG AGTCGCCGTG TCGGACGTCT CCCGGTGTCC GGACCCGTCC GGCAACCTCC 2160
2161 CGGGCGAAGG AGCTGCCGTG CTGTCATCAG CGGCCGTTGGC GCCGTCAGCC GAAGAGTTCG CCCGGTGTCC GGACCCGTCC
                                                                  start of cvm7par →
2241 CCACCGCGCT CTGTCATCAG CGGCCGTCGGC GCCGTCAGCC ACGCA GAGAA GATCGGATAC GCAGTGTACG AGTGCAGGA 2320
2321 TGAGGTTCGT CACGACGTCC CCGGCCTGCC GGTCCGTCA CCGTCCATCA CCGTCCTGGG CTGTCTGGGC GTACGGCCCG 2400
2401 ACGGCCGGAA ACTGGAGCTG GGCCCCTCGC GTCAGCGGGC CGTTTTCGCC CTGCTGCTCA TCAACGCGGG CAGTGTGGTG 2480
2481 CCGGTCGACt cgatcgtctt ccgtatctgg ggcaactcac caccggggcgc ggtcaccgcg acgctccagt cctatgtgtc 2560
```

```
2561 ccggctgcgg aaactcctgg ccgagtgtgt gctccccgac ggttcgacac ccgaactgct gcaccagccg ccgggctaca 2640
2641 ccctcgcgct cggcaccgag cacatcgacg cgaaccgttt tgagcaggcc atcaggacag ggcgccggct ctcgcgcgag 2720
2721 gagcagcacc aggaggcgcg ggccgtgctc tgccaggccc tgctgagctg gggcgggaca ccgtacgagg agctgagcgc 2800
2801 gtacgacttc gccgtccagg aggccaatcg gctgagcag ctccggctgg gcgccgtgga gacatgggcg cactgctgtc 2880
2881 tgcggctggg gcgggacgag gaggTGATGG ACCAGCTCAA GCCGGAGGTG CAGGCGCAATC CGCTGCGGGA GCGGCTGATC 2960
2961 GGGCAGCTCA TGCAGGCGCA GTACCGGCTG CAGGACGTAC CAGGACGCGCT CGGGATCCT GCGTCAGGAC GGCGGGCCCT 3040
3041 GGCCGAGGAG CTGGGGACCG ATCCGGGCAA GGAGCTGGCC GCGCTGCACG GCCGTGACGG TGTCGGTCC GGCACAGCCG 3120
3121 ACCGCGTCGT CCCGGCGTCC GCGCCGCCGT CGGCGGGGG CGGGCGGGGG GATGACGGTG GCGGGGGCG CGGGGCGGC 3200
3201 TCGAGGCCGT TGACGCGGCC GGTGCGGGGC CCGTTTCCGC GGCTCCGGCT CCGGCTCCG CTCCGCTCCT GCGTCGGTTC 3280
3281 CCCCGCGTCC GCCTCCGGCT CCGTTTCCGC GTCCGTTCCG GTTCCTGGCT GTAGCCGCGC CCGTTTCCGG CCATGTCTCC 3360
3361 CCACCTTCTT TCCCGGCTCC GTTTCTGGCT CGGCGTCCGT TGCCGCGTCC CGCAGACCCT CCGGGGCGAG CCGGTCCACG GGGGCGCGCA 3440
3441 GGGCCCGGGT CCGCTTTCGG GTCCGTGGCG CTCCACCGGC CGCCGTGGGC CCGGGCGAG GCGGCGACGA GCTgcgcggt ctgctggagt 3520
3521 GGGGATGCGC ACCGGGCAGG TGTTCCCCAC GCTGCCGCCG TTCGTCGGGC GCGGCAAGAC CCGGCTCCTC 3680
3601 ccgcgacgtc cgcgttccac acctcggggc gggtgccgtt cgtcgtcggc gaggcggca gcggcaagac ccggctcctc 3680
3681 tccgagttgg agcgctcggt tccggacagt gtgcgcacgg tctgtttcgag agtgaggacc ggcccgacta ggcggcgga 3760
3761 ctgccggtgg acgaccgtgg tgcggcatct gtacgcgatg tggccggaac gtatgcacgg attcccccggt tggctgcggc 3840
3841 gcgcactcgc ggaactgctt ccccggagcc gcccggagcc acaggggccg cactccccccg acggggcga ggagaacagc 3920
```

```
3921 ggcaacgggg acgtgcgggg cgacggggac agcacccgg   cgcacaccct cacgctcgcg cccgctctcg cgccccgcg  4000
4001 ctccagagag gctcgtttca ccctgcacga cgccgtgtgc   caggcgcttc tgcgcacggt ccgcgaaccc gtggtgatca 4080
4081 tgctggagga catggagcgg gccgagcgcc cctcgctcgc   cctgctgcgc ctcctggtgg agcaactgcg ctcgtcccc  4160
4161 ctgctgctcg tggtcaccac ggcgcacttc cggctcgcgc   acgacgccga gctgcgacgg gccgcccgcg tgatcctcca 4240
4241 gtcgaccggc gcgcgcccgg tcctgctgaa cgccctgac   gcacgggcca ccggggaact cgccggaggg atgctgggca 4320
4321 aggccccgga cacctcctc  gtacggggcc tgcacgagcg   ctccgcgggg aaccgtact  tcctcgtcca gctcctccgc 4400
4401 tcgctccgggc agggctcgc cccgcgcctgc gccggtgct   cgacatctgc gcggtcgtgg agcgcagttg cgaacggcgt gtgatcgaga 4480
4481 gagcgtgcgg cccgcgcctgc gccggtgct  cgacatctgc   gcggtcgtgg agcgcagttg cgaacggcgt gtgatcgaga 4560
4561 ccgtgctgcg ccatgaggga atcccgctgg agaacgtccg   tacggcggtc cgcgggggtc tgctggagga agaccccgac 4640
4641 gaccccgggc ggctgaggtt cgtgcatccg ctggtccggg   aggccgtctg ggacgacctg gagaacacccc gtccgcccgt 4720
              stop cvm7par→
4721 gtcccgttcc tccgcgttcg gggcgctggc cacggtctga   gtccccggcc ccgggggtcct cgGCGGCGGG CGGCGGCTTGC 4800
4801 GCGCTCCCCG ACGCGGGGCT TGATCCCCCG GGGCCAGCGG   ACGCGCAGCC GGGTGCAAGG GGCGGTGCCG ACACTGGGCG 4880
4881 GGGGCGGCC  GTGGCCGGTC CACCCACCCG GCCGCCCACC   GAGGAGCCCC CATTGGACAC GTACGCAGCG GATACGTACC 4960
4961 CGCGGTCCGG CACCCACCAC CCGACGCGCA GAGCCGCGTC   TCCCCACGCG CGTCCCCGGA CCCGTCCCGG CACCCGTTCC 5040
                                                                              start cvm6par→
5041 GAGCCGCGCC CGGACCCGCC CGCGAGGCC  GCCGTGGCTGC  TCGGCGGGA  CCCGCGCCCAT ATGTTCCACC CGGTCCTGCC 5120
5121 CCGGGGCCGC GAGGACCGCA CCGTTCTGGT CTCCGGCCGC   GGCTGCACCG TACGGACACAC CGAAGGGGCGC ACCTATCTCG 5200
```

```
5201 ACGCCTCGTC GGTGCTCGGA CTGACCCAGA TCGGCCATGG ACGTGAGGAG ATCGCGCAGG CCGCCGCCGA GCAGATGCGG 5280
5281 ACACTCGGTC ACTTCCACAC CTGGGGCACC ATCAGCAACG ACAAGGCCAT CCGACTGGCC GGCGCCCTCA CCGACCTGGC 5360
5361 GCCCCAGGGT CTCCAGCGCG TCTACTTCAC CAGCGGCGGC GGCGAGGGCG TCGAGATCGC CCTGCGCATG GCCCGTTACT 5440
5441 TCCACCACCG CACCGGCAGC CCGGAGCGCA CCTGGATCTT GTCGCGCCGC ACGGCATCGG CTACGGCAGC 5520
5521 GGTACGGTGT CGGGCTCGCC CGCCTACCAC GACGGGTTCG GCCCCATGTG CACCACCTCA CGCCGCCCGA 5600
5601 CCCGTACCAC GCCGAGCTGT ACGACGGCGA GAGTACTGCC TGCGCGAACT CGCCCGCCACC ATCGACGAGA 5680
5681 TCGGCCCCCG GCGGATCGCC GGGAGCCGGT GGCGGGCGCG TCGTCCCGCC GCCGGACTAC 5760
5761 TGGCCGCGCG TCGCCGCGCT GCTGCGCTCC CACGGCATCC GAGTACTCCT GTCACCGCGT TCGGCCGCAC 5840
5841 GGGGACCTGG TTCGCGGCCG GGCGGTGCTC AGCACTTCGG GGTGACCCCC TGACCGGAA GGGCATCACC TCCGGGTATG 5920
5921 TCCCGCACGG GGCGGACACC CTGACCGAGG AGTCGCGGGA CGCCGTGAAC GGGGAGACGG GGTTCCCGAT CGGCTTCACC 6000
6001 TATACCGGTC ACCCCACGGC GTGCCCCGTC GCGCTCGCCA ATCTCGACAT CATCGAACGG GAAGGGCTGC TGGAGAACGC 6080
6081 GGTGAAGGTG GGCGACCACC TCGCCGGGCG GCTGGGCGCC CTGCGCGGGC TGCCCGCCGT GGGGACGTC CGGCAACTGG 6160
6161 GCATGATGCT CGCCGTCGAG ACAAGACGGC CCGCACCCCG CTGCCGGGCG GCACCCTCGG GTCGTGGAAC 6240
6241 GCGCTGCGCG AGGACGCGGG CGTCATCGTC CGGGCCACGC CGGCTCCTCAAT CCGGGCTCG TGATGGACCG 6320
```

```
6321 GGCCACGGCG GACGAGGTGG CGGACGGGCT CGGACTCGGTG CTGCGGCCGC TGGCACCCGA CGGGCGGATC GGCGCGGCCC 6400
     stop cvm6par ↑
6401 CCCGGGCGGGG GTGACGAGAC CGCGGGCCGC CACCCGCGGG GGGCGCCGGG TCGGCACAGC GGCCGACCCG GCGCCTTCCC 6480
6481 CGTTTCCCGG CGCCTTTTCC GTGCCCCGGC GCCGTTCCCG TGGCCCCTGC CCCTGCCCCT GCTCGGGCGC TCCTCCCTCC 6560
6561 GCTGTGGCGC CGTTCCCGTT CCAGGCGCGT GTCGAGCCGC CGCCAAGCGC CCCGTGCCAC GGTGGGAGAC CGCCGCCCGA 6640
6641 CGGGGCGCGC GGAGCCCGGC AAGCCC AAGG GAAG CCCGT CCGATGCGTG CCTCTTCGCC CAGAGGGTTC CGGCGTGCACC 6720
                                                        ↑ start orf6par
6721 ACGGTCACGC CGGGATCAGG GGGTCCCACG CGGACCTCGC CGTCATCGCC TCCGACGTTC CCGGCGCGGT CGGGCGGGTG 6800
6801 TTCACCCGGT CGCGGTTCGC GGCAACGCCA ACGCCGGGAC CGGCCCGAGT GTGCTGCTCA GCCGGGACGC GGGATCGCCC GGGGCGTGGT 6880
6881 GGTGCTGTCC GGCGACGAGC AGGGATGTGC CGGCCCGGGA GGTGCCGCCCAT CTGGTGGCCG 6960
6961 GGATCGTCGA CTGCGACGGG AGGGATGTGC TGATCGCCTC CACGGGACCC GTCGCGAGC GGTATCCGAT GTCCCGTGTC 7040
7041 CGGGCCCATC TGCGGGCCGC TTACCGGGTC CGACTTCGA CGGCGGGCG GCGGCCGTGC TGGCACCGC 7120
7121 GGGGCGCCCGT CCCACGATCC GGGGCGGCG GTGGCGCGAC GGGAGCCTGA TCGGTGTCGC CAAGGGCCCG GGTACGGGCC 7200
7201 CGGCGGAGCA GGACGACCGG TCGGCGCTGG CAGGTGAGCC CGTCGTCCT CGACCAGATC 7280
7281 TTCCGACGGG TCGGCGGGGG CGCCTTCCAC CGCCTGGGCT CGGGGCGCCA CGGCCGTTCT 7360
7361 CGGCAACGGG CTCGCCGTTC GGGTGGACCT TGGGCGCGCT CGTCGGGCGC CTGGTCAGGG 7440
7441 ACGTCGTCCG GGACAGCGGC ACCGGGCGTC ACGACACCGA GCAGGCCGGG 7520
```

```
7521  CGGCGTGGGCC GGGCGGTGGT CGACGCGCCG TCGCTGAGGG CCGCGGTGCA CGGCCCGGCA CCCGACTGGG CGCCGGTCGC  7600
7601  CGCCGTGGGCG GGTGGACACG GGGACGAAGG CCCCGGCCGG TCTCCCCGGG GGATCACGAT CCGGGTCGGC GGCCGGGAGG  7680
7681  TCTTCCCCGC CCCCGCGAC CGGGCCCGCC CGGACGCCGT CACGCGGTAT CCGCACGGCG GCGAGGTGAC CGTCCATATC  7760
7761  GACCTCGGTG TCCCGGGCCG GGCGCCCGGC GCGTTCACGG TCCACGGGCTG CGACCTCCTG CGGGGTACC CGGCCCTCGG  7840
7841  CGCCGGCCGG GCCGTCTGAA CGGGCGCTCC GGGCGCGGGA GCGCAGGGAA CACGGGAGCG
      stop orf6par →                                                                        7920
7921  GGCCCCGGTGG TCGATCGGCC ACCGGGCCCG CTCCCCGTCGT TCCGTCCGCT GTCCCCCGGCC GCCCTACCCC CACCGCTGCC  8000
                                                                       ← stop orf4par
8001  CGGCGAAGTC CACGGGCGCT CCGGCCGCTC CCGGCCGTCCA CCGGCCGCGAC CGGTCCGTCGT GCGTTCTCGG CGCCCGCCCC  8080
8081  GGTGGCAGGG GAGAGTCCAG AGCAGGGAGG TGATCCCCGA CGGTCGCCGAC GGCGTACTGG TAGAGCAGTT CGGCCGTCGG  8160
8161  CTCGCCCGCC AGCAGGGAGG TGAAGTCGGC AGGGTCAGCA CCTCGCCCGCA GCCGGGGACA CCTCGACCAC GTCGAAGCCG  8240
8241  GCTGCCCGAC CACGTCGAGC AGGGTCAGCA CCTCGCCCGA GGCGGACACGCC GCCGACGTG CCGTGCCCGCC GTGTGCCGGT  8320
8321  TACGCCGGGT CGACGACGTC GATGTCGACG GAGACGTACA GCGGCAGGCC GCGGGATCT GCCCGGATCT GCTCGGCGAT  8400
8401  GCCGGCCGGT GAGCGCCGGG TGAAGTCGGC GACGGTGACG ATGCTGACGC CGTGCCCGCC CGGTAGTCC AGGGAGTCGG  8480
8481  GCCGCGGATT GTGGCCGCGG ATGCCGACCT GGACCAGGCG CTCCGGGTCC ACCAGCCCT CTTCGATGGC CCAGCGGAAG  8560
8561  GGGTGCCGT GGTGGTAGGT ACGGGTGGGT TGGTGTCGCT GTGCGCGTCC AGGTGCAGGA CGGCGACCCG  8640
```

```
8641  GCCGTGGCGG  GCGTGCACGG  CGGCCAGGGC  GGCCAGGGAG  AGCGAGTGGT  CCCCGCCCAG  CATCAGGAAC  GCGTCGTTGC  8720
8721  GTTCCAGGAG  CCGGGTCAGG  GCGACCGTCG  CGGTGTCCAT  CGCCAGGTCC  ATCGAGAAGG  GGCTGAGGTC  GATGTCGCCC  8800
8801  CCGTCGACCA  CGTCGATCCG  GTCGAAGACC  CCTGGGCCCC  GGTCGATGCC  GACGCCGTGG  ATCAGGCTGG  ACTCGTGCCG  8880
8881  GATGGCGCGC  GGCGCGAACC  GCGCGCCGGG  CCGGTAGCTG  GTGCCTCCGT  CGTACGGGGC  GCCGACGACC  ACCACGTCAT  8960
                                                                                              start orf4par→
8961  GGCCGATCGG  GTCGGGGCCG  TGGCGCAGCC  CGGTAGCGCG  GCCCGGTTGG  GCGTAGCGCG  GGAGACGGC   GGTGGACACC  9040
9041  CTGGCCGTTC  CCGGCGCACC  CGGCCCCTGCT  CCCGTTCCCG  TACCGACGCC  GTGCGGGCTC  CCGTTCCCGT  9120
9043  GCCGACCCCC  GTTCCCGAAC  GGGCTCCCGT  TCCCGCGTGG  AATCCCGTTC  CGGCCACCCC  CCGCGCCCGC  GGGCCGCGGC  9200
9201  TGCCCCTCCC  TCCGAGACCG  CGGCCGCCGCC  TCCTGCGGCC  GTTGCGCTC   TGCCGGCCGG  GCCACCGGTG  CACGCCCGCC  9280
                                                                                              ↓ stop
9281  GCACCGTCCG  CGCCGCCGCC  GGTGCCGTTG  CCGCGCCGCG  GTTGCCCGCC  CCGTTCTGGC  CGCTCATACG  9360
      orf3par
9361  ACCACCCGGC  CCTGGAGCCT  GAGCCGCCGC  ACCGCGTCGA  CGGAGCGGCC  CACCGTCTCG  CCGAAGTCCA  CGTCCTCCGG  9440
9441  CGGCACCGTG  TCGATGACCA  CCGCGTCGTA  CAGGCGCGCGT  GCCATGGCGC  CCTTGACGGC  CGTCACCTCG  TCGCCGGGA   9520
9521  TCCCTTCCGC  GAGGAGCAGT  GCAGCAGGCC  CCGGTCCACG  GCCGACCCCC  TCGTGGATGC  CCAGCTTGGG  GCGGGCCACG  9600
9601  GTCTCGGCGG  GCAGCAGGCC  GGAGAGGGCC  CGGTGGTGGT  CCCACTTGTC  TGCCGCAACA  CGGCGTTTGA  GCCCGGGTTC  9680
9681  GAGGGAGACC  AGCCGCGTCCA  GGACCGGCCG  GTCCCAGTAC  GGTGGGGTGG  TCCACTTCCC  GCCGATGCCC  GCGAGGACGG  9760
```

```
 9761  GGGACATCTC  GTTGAGGCCG  TCGAAGCCCG  CCATGTCGCC  CGCCATCTCG  TCGTCGAGGG  ACCAGAGCGA  GGCCGTGCGC   9840
 9841  CGGTGCATAC  CGCCGAGCGG  GATGTCGGCG  CCGTACCCGG  TGAGGATGCG  GAGCGGCCCG  GTGTCGAGCC  GCGGTAGAG   9920
 9921  GGCCGACGAGC  GGCAGCAGGT  ACTCCAGGAC  CGTGGGGTCG  GTGATCTCCG  CGGCGGCGAC  CGCCAGGGC   AGTTCCCTGA  10000
10001  CGAGTTCGGC  CGAGTGGAGC  CGGATCTCGC  TGTGCGCGGT  GCCCAGGTGG  ACGGCGACCG  AGCGGGCCGC  GTCGAACTCG  10080
10081  TCGGACACCT  CGGTGCCCAT  CGACACGGAC  CGTGTCCCGG  GTGCCAGGGC  CGCCGTGTGG  GGGCGGACTC  CCCCGGAGTC  10160
10161  GATGCCGCCG  GACAGGACGA  CGGTGGGGGC  CGCCCTCCCCG  CCCCGTGGCG  GGGCGGAC    CGCCGTGGCG  AGGGCGTTCG  10240
10241  CGACCAGGTC  CACCCGCCTCC  CGTTCGCCGG  GTGCAGCAGG  GGTGTCCAGG  TGCGGACCGC  CCTGGCGGTG  10320
10321  ATGTCGGAGC  CGCCGACTCC  GTGCAGCAGG  AGGGGCGGTCC  CCGGCGGGAC  CCCGCAGACG  CCCCGCGCCC  CCGGCGCGGT  10400
10401  GTGGGTGCCG  GACAGGCCCA  GCGGCCGCGC  CGGCTCGTGC  GCCAGGGTCT  TCGCCTCGGT  GGCGGCGCTC  AGCCCGTCA   10480
10481  CGTCGGCGCG  CAGCCACAGC  GGTACCGGAAC  CGGCCGTGGGC  GGTGGCCGGG  ACGGTGCGCG  CGGTGGAGGC  GTCGGTGAGC  10560
10561  AGTGCGGGGA  ACCGTCCGTT  CAGGAGCCGG  GGCCCCAGCG  CCGCCAGGCG  GCCAGCAGCA  GTTCGGCGTC  10640
10641  GCCGAGGGCG  GCAGAGGAGC  CGCCGAGCGC  TCCGGGTCAGC  TCGGCGCCGGT  TGTACAGCTC  GCCCGCCAGG  AGCAGCCGGA  10720
10721  CCTGGCCCGTC  GGCGACCAGG  ACGGGCGGAA  GGCCACCAGG  TCCGGCGGGG  CCGCTCCAGA  GCGGGTACGC  GGTGCCGTCG  10800
10801  TGCACGGGGA  CATGGGTCCC  GCGGACGGGCC  AAGCGGGGTG  CGCTGCCGGG  TTCGGAGTGA  CCCGCCGGGC  CGCCGCCGGG  10880
10881  GCGGGCCCTCG  GTGCCGATGC  GCACCCGGAA  TCCGTACACG  AGGTCGGGGC  CGGGACATGGT  GAA TGTCC  TC  ACGGGTGG  10960
         ← end orf2par                                                          start orf3par →
10961  TCAGATGGCC  AGGGCGGCGA  AACCGCCCGA  CTGGAAGTCG  TAGGCCACCG  GTACCTCGAT  CAGGAACGGG  CGGCCGAGTC  11040
```

```
11041 CGGCGCCCTT GGTGAGGGCG GCGAGCAGCG AGGTGCGGTC GGTGGCGCGG ACGGCCTCGC AGCCGTTGGC CTCGGCGAGC 11120
11121 TGGACGAAGT CGACGCTTCC GAAGCCGACG GCGGGGGCGT GGGAGCGCTG GTGTCCGAGG TTCTGGTACA GCTCGATCAG 11200
11201 GCCGTTGCGG TCGTTGTTGA CGACGACCAT CGACATCGGC AGGCCCAGGC GCACGGCCGT CTCGATGTCG GCGCTGTTGG 11280
11281 AGTGGAAGCC GCCGTCGCCC GCGATCGAGA AGACGGGCTC GCCGGGCCGG GCGATCTGGG CGGCCATGGC GGCGGGCAGT 11360
11361 CCGTAGCCGA AGCTGGAGCA GCCCGCGGAG GTGAGGAATC CGTACGGCTG GTCGGACTTG GCGAAGAGCA CGCCGTAGTG 11440
11441 GCGGAAGAAG CCGATGTCGC TGACGAAGGT GCCGTTGTCG AGGACGGAGT TCATGCAGTC GCCAGGGCGC GATCACCTGG 11520
11521 TGCCCGTCCTC GTACTCGGTG GGGTCGGCGA GGAATTCGGC GACGCGGGCG CGCAGGGCGC TGAGGTCGTG CCGGGTCTTG 11600
11601 GGGGCGAGGC CCGAGGTTGA CCTCGGGGGC GCGGTGACGA ATTCGGCGAC GTTGGTGACG CGGCCCCCCG ATGTCGATGT 11680
11681 CAGCTCCGGG ATCGGGTTGA CCGATCGTAG CCGATCGCCA GGAGGAGGTC GTGGTCTTGG CCGGGGCCGG CGAGGGCCCG 11760
11761 GGTCCTCGGC GTAGTCGTAG TGTAGCCGCT GATGGCGCCG TAGTTGAGCG GGCGGGGACG CGAGGGCCCG GTGGCCGAGA 11840
11841 ATGCCGTCCA TGTAGCCGCT GATGGCGCCG TAGTTGAGCG GGTGGTCGTG CGGCAGGACG CCCTTGGCGG TGTAGGTGGT 11920
11921 GACGACGGGG ATGTTCAGCC GCTCGGCGAG GGCGCGCAGG GCGTCGACGG GATGACGGCG CTACCGACGA 12000
12001 CGAGGAGGGG GTTCTCGGCC TCGCGCACCA GCTCAGCGGC CTCGTCGAGG CGGCGCGCC AGTCGGCGTC CAGGGCGTGG 12080
12081 GTGGGGGTGG CCCGGACCAG GGGGGCGTCG GTGGGGTGC CGTTCAGCTC GGCGCCGAGG AGTCGACCG GCAGGCTGAT 12160
12161 GAAGCTGGGA CCCACGGGCT CGATCCGGCT GTTGAGGACG GCGCTGTCGA CGAGGTTGAC GATGTCCTCG CCCGCGTTCGA 12240
```

```
12241 GCTGGACGCT GAACTTGGTC AGCGGGCCCA TCACGGCGGT GCTGTCCAGG CACTGGTGGG TGACGTTGGG
GTAGCAGTCG 12320
12321 TACGACTCGG ACTGCGCGGC CAGCGCGATG ACCGAGCTGC GGTCCAGGGC GGAGGTGGCG ACGCCGGTGG
CCAGGTTGGT 12400
12401 CATGCCGGGG CCCAGGGTCG CGAAGCACGC CTGGGGGCGG TTGGTGATCC GGGCGAGGAC GTCCGCCATC
ACCCCGGCGG 12480
12481 TGAACTCGTG CCGGGTCAGG ACGAAGTCGA GTCCTTCGAC CTCGTCGAAG AGAATGGCGG ACGCCTCCCG
GCCGACGACG 12560
                                                          start of orf2par ←
12561 CCGAATACAT GGTCGACACC GTACTGGTGA AGACGTTCCA GCATGGCTTT CGCGGTCGTG GTGGCCATGG
AGATCTCCTT 12640
12641 CGCATCGGAC GGGCGCCGGG ATGGCGCCCC GGAAAACGCG GCACCGGGCG GTGCGCACCG GGTGGCGCAC
ACCGTGGGTG 12720
12721 GTGGCGTTGC CACTGTGCGG ATCGCCTCTT GGCGGCGGTC GGACGCCCGG CTTGGACAGA ATGGGCAAGG
CGCGTTCAAG 12800
12801 GCATGGCGTC CATCGTCCTC GTGGCGCTTT TCGTGAAATC CGTCCGGCGC CGACGGTCTC CATCCGATTC
CGTCCCCTTC 12880
12881 CGTCCACCGA TCCGAGGAGA ATCCATGGAT GTCCTGGCCG CGTTGGAGCG CAAGCCCAGC CTGAATCTTT
TCCCCATCGA 12960
12961 GAACCGGCTG TCGCCGCGCG CCAGTGCCGC GCTGGCCACC GACGCCGTCA ACCGCTATCC GTACTCCGAG
ACCCCGGTGG 13040
13041 CCGTCTACGG CGATGTCACG GGGCTGGCCG AGGTGTACGC GTACTGCGAG GACCTGGCCA AGCGCTTCTT
CGGGGCGCGC 13120
13121 CACGCCGGTG TGCAGTTCCT GTCCGGTCTG CACACCATGC ACACCGTGCT GACCGCCCTG ACCCCGCCCG
GCGGGCGCGT 13200
13201 CCTGGTCCTC GCGCCGGAGG ACGGCGGCCA CTACGCCACG GTGACGATCT GCCGGGGCTT CGGCTACGAG
GTCGAGTTCT 13280
13281 TACCTTCGAC CGCCGGACAC CTGGAGATCG ACT
13313 (SEQ ID NO:16)
        |   10    |   20    |   30    |   40    |   50    |   60    |   70
|   80
```

Figure 3k

SEQUENCE LISTING

<160> NUMBER OF SEQ ID NOS: 28

<210> SEQ ID NO 1
<211> LENGTH: 1314
<212> TYPE: DNA
<213> ORGANISM: Streptomyces Clavuligerus

<400> SEQUENCE: 1

| | | | | | |
|---|---|---|---|---|---|
| atgttccacc | cggtcctgcc | ccggggccgc | gaggaccgca | ccgttctggt | ctccggccgc | 60 |
| ggctgcaccg | tacgggacac | cgaagggcgc | acctatctcg | acgcctcgtc | ggtgctcgga | 120 |
| ctgacccaga | tcggccatgg | acgtgaggag | atcgcgcagg | ccgccgccga | gcagatgcgg | 180 |
| acactcggtc | acttccacac | ctggggcacc | atcagcaacg | acaaggccat | ccgactggcc | 240 |
| gcgcgcctca | ccgacctggc | gccccagggt | ctccagcgcg | tctacttcac | cagcggcggc | 300 |
| ggcgagggcg | tcgagatcgc | cctgcgcatg | gcccgttact | ccaccaccg | caccggcagc | 360 |
| ccggagcgca | cctggatctt | gtcgcgccgc | accgcctacc | acggcatcgg | ctacggcagc | 420 |
| ggtacggtgt | cgggctcgcc | cgcctaccag | gacgggttcg | gcccggtgct | gccccatgtg | 480 |
| caccacctca | cgccgcccga | cccgtaccac | gccgagctgt | acgacggcga | ggacgtcacg | 540 |
| gagtactgcc | tgcgcgaact | cgcccgcacc | atcgacgaga | tcggcccgg | gcggatcgcc | 600 |
| gcgatgatcg | gggagccggt | catgggcgcg | gcggcgccg | tcgtcccgcc | gccggactac | 660 |
| tggccgcgcg | tcgccgcgct | gctgcgctcc | cacggcatcc | tgctgatcct | ggacgaggtc | 720 |
| gtcaccgcgt | tcggccgcac | ggggacctgg | ttcgcggccg | agcacttcgg | ggtgaccccc | 780 |
| gatctgctgg | tgaccgcgaa | gggcatcacc | tccgggtatg | tcccgcacgg | ggcggtgctc | 840 |
| ctgaccgagg | aggtcgcgga | cgccgtgaac | ggggagacgg | ggttcccgat | cggcttcacc | 900 |
| tataccggtc | accccacggc | gtgcgccgtc | gcgctcgcca | atctcgacat | catcgaacgg | 960 |
| gaagggctgc | tggagaacgc | ggtgaaggtg | gcgaccacc | tcgccgggcg | gctggcggcc | 1020 |
| ctgcgcgggc | tgcccgccgt | gggggacgtc | cggcaactgg | gcatgatgct | cgccgtcgag | 1080 |
| ctggtgtcgg | acaagacggc | ccgcaccccg | ctgccggggcg | gcaccctcgg | ggtcgtggac | 1140 |
| gcgctgcgcg | aggacgcggg | cgtcatcgtc | cgggccacgc | cgcgctccct | ggtcctcaat | 1200 |
| ccggcgctcg | tgatggaccg | ggccacggcg | gacgaggtgg | cggacgggct | ggactcggtg | 1260 |
| ctgcggcggc | tggcacccga | cgggcggatc | ggcgcggccc | ccggcgggg | gtga | 1314 |

<210> SEQ ID NO 2
<211> LENGTH: 2464
<212> TYPE: DNA
<213> ORGANISM: Streptomyces Clavuligerus

<400> SEQUENCE: 2

| | | | | | |
|---|---|---|---|---|---|
| gtgtacgagt | gcagcgatga | ggttcgtcac | gacgtccccg | gcctgccggg | tccgtcaccg | 60 |
| tccatcaccg | tcctgggctg | tctgggcgta | cgcgccgacg | gccggaaact | ggagctgggc | 120 |
| cctccgcgtc | agcgggccgt | tttcgccctg | ctgctcatca | cgcgggcag | tgtggtgccg | 180 |
| gtcgactcga | tcgtcttccg | tatctggggc | aactcaccac | cgggcgcggt | caccgcgacg | 240 |
| ctccagtcct | atgtgtcccg | gctgcggaaa | ctcctggccg | agtgtgtgct | cccggacggt | 300 |
| tcgacaccca | aactgctgca | ccagccgccg | ggctacaccc | tcgcgctcgg | caccgagcac | 360 |
| atcgacgcga | accgttttga | gcaggccatc | aggacagggc | gccggctctc | gcgcgaggag | 420 |

```
cagcaccagg aggcgcgggc cgtgctctgc caggccctgc tgagctgggg cgggacaccg    480
tacgaggagc tgagcgcgta cgacttcgcc gtccaggagg ccaatcggct ggagcagctc    540
cggctgggcg ccgtggagac atgggcgcac tgctgtctgc ggctgggcg  ggacgaggag    600 gtgatggacc agctcaagcc ggaggtgcag cgcaatccgc tgcgggagcg gctgatcggg    660
cagctcatgc aggcgcagta ccggctgggg tgccaggcgg acgcgctcag gacgtacgag    720
gcgacgcggc gggccctggc cgaggagctg ggaccgatc  cgggcaagga gctggcggcg    780
ctgcacgcgg cgatcctgcg tcaggacaac ggtctggacc gcgtcgtccc ggcgtccgcg    840
ccgccgtcgg cggggtcgg  gcggggggcc gtgacggtgt cggtcccggc acagcggtcg    900
aggccgttga cgcggccggt ggcggggcgg gcgcgggtcc cggggcgat  gacggtggcg    960 gcgggcgcgg gggcggcccc cgcgtccgcc tccggctccg tttccgcgtc cgtttccggc   1020
tccggctccg gctccggctc cgctcctgcg tcggttccca ccttctttcc cggctccgtt   1080
tctggctcgg cgtccgttgc cgcgtccgta ccgcgcccg  tttccggcca tgtctccggg   1140
cccgggtccg ctttcgggtc cgtggcgctc accggccgc  agaccctccg gggcgagccg   1200
gtccacgggg gcgcgcaggg gatgcgcacc gggcaggtgt tccccacgct gccgccgttc   1260
gtcgggcgcg cgacgagct  gcgcggtctg ctggagtccg cgacgtccgc gttccacacc   1320
tcggggcggg tggcgttcgt cgtcggcgag cgggcagcg  gcaagacccg gctcctctcc   1380
gagttggagc gctcggttcc ggacagtgtg cgcaccgtct gggcgtcctg ttcggagagt   1440
gaggaccggc ccgactactg gccgtggacg accgtgctgc ggcatctgta cgcgatgtgg   1500
ccggaacgta tgcacggatt ccccggttgg ctgcggcgcg cactcgcgga actgcttccc   1560
gaggtgggcc cggagccaca ggggccgcac tcccccgacg ggggcgagga aacagcggc   1620 aacggggacg tgcgggcga  cggggacagc accccgccgc acaccctcac gctcgcgccc   1680
gctctcgcgc cccgcgctc  cagagaggct cgtttcaccc tgcacgacgc cgtgtgccag   1740
gcgcttctgc gcacggtccg cgaacccgtg gtgatcatgc tggaggacat ggagcgggcc   1800 gacgcccct  cgctcgccct gctgcgcctc ctggtgagc  aactgcgcac cgtcccctg   1860 ctgctcgtgg tcaccacgcg caccttccgg ctcgcgcacg acgccgagct gcgacgggcc   1920
gccgccgtga tcctccagtc gaccggcgcg cgccgggtcc tgctgaacgc cctggacgca   1980
cgggccaccg gggaactcgc cggagggatg ctgggcaagg ccccggacac cctcctcgta   2040
cgggccctgc acgagcgctc cgccgggaac ccgtacttcc tcgtccagct cctccgctcg   2100
ctccggcagg ggctcgccgc cgcctgggag acggagatcc cggacgagct ggccggggtc   2160
gtgctgcaac ggctgtcgag cgtgccgccc gccgtgcgcc gggtgctcga catctgcgcg   2220
gtcgtggagc gcagttgcga acggcgtgtg atcgagaccg tgctgcgcca tgagggaatc   2280
ccgctggaga acgtccgtac ggcggtccgc ggcggtctgc tggaggaaga ccccgacgac   2340
cccgggcggc tgaggttcgt gcatccgctg gtccgggagg ccgtctggga cgacctggag   2400 aacaccgtc  ggcccgtstc vmargtcccg ttcctccgcg ctcggggcgc tggccacggt   2460
ctga                                                                2464
```

<210> SEQ ID NO 3
<211> LENGTH: 437
<212> TYPE: PRT
<213> ORGANISM: Streptomycesl clavuligerus

<400> SEQUENCE: 3

```
Met Phe His Pro Val Leu Pro Arg Gly Arg Glu Asp Arg Thr Val Leu
  1               5                  10                  15

Val Ser Gly Arg Gly Cys Thr Val Arg Asp Thr Glu Gly Arg Thr Tyr
             20                  25                  30

Leu Asp Ala Ser Ser Val Leu Gly Leu Thr Gln Ile Gly His Gly Arg
             35                  40                  45

Glu Glu Ile Ala Gln Ala Ala Glu Gln Met Arg Thr Leu Gly His
 50                  55                  60

Phe His Thr Trp Gly Thr Ile Ser Asn Asp Lys Ala Ile Arg Leu Ala
 65                  70                  75                  80

Ala Arg Leu Thr Asp Leu Ala Pro Gln Gly Leu Gln Arg Val Tyr Phe
                 85                  90                  95

Thr Ser Gly Gly Gly Glu Gly Val Glu Ile Ala Leu Arg Met Ala Arg
                100                 105                 110

Tyr Phe His His Arg Thr Gly Ser Pro Glu Arg Thr Trp Ile Leu Ser
            115                 120                 125

Arg Arg Thr Ala Tyr His Gly Ile Gly Tyr Gly Ser Gly Thr Val Ser
130                 135                 140

Gly Ser Pro Ala Tyr Gln Asp Gly Phe Gly Pro Val Leu Pro His Val
145                 150                 155                 160

His His Leu Thr Pro Pro Asp Pro Tyr His Ala Glu Leu Tyr Asp Gly
                165                 170                 175

Glu Asp Val Thr Glu Tyr Cys Leu Arg Glu Leu Ala Arg Thr Ile Asp
            180                 185                 190

Glu Ile Gly Pro Gly Arg Ile Ala Ala Met Ile Gly Glu Pro Val Met
            195                 200                 205

Gly Ala Gly Gly Ala Val Val Pro Pro Asp Tyr Trp Pro Arg Val
210                 215                 220

Ala Ala Leu Leu Arg Ser His Gly Ile Leu Leu Ile Leu Asp Glu Val
225                 230                 235                 240

Val Thr Ala Phe Gly Arg Thr Gly Thr Trp Phe Ala Ala Glu His Phe
                245                 250                 255

Gly Val Thr Pro Asp Leu Leu Val Thr Ala Lys Gly Ile Thr Ser Gly
            260                 265                 270

Tyr Val Pro His Gly Ala Val Leu Leu Thr Glu Glu Val Ala Asp Ala
275                 280                 285

Val Asn Gly Glu Thr Gly Phe Pro Ile Gly Phe Thr Tyr Thr Gly His
            290                 295                 300

Pro Thr Ala Cys Ala Val Ala Leu Ala Asn Leu Asp Ile Ile Glu Arg
305                 310                 315                 320

Glu Gly Leu Leu Glu Asn Ala Val Lys Val Gly Asp His Leu Ala Gly
                325                 330                 335

Arg Leu Ala Ala Leu Arg Gly Leu Pro Ala Val Gly Asp Val Arg Gln
            340                 345                 350

Leu Gly Met Met Leu Ala Val Glu Leu Val Ser Asp Lys Thr Ala Arg
            355                 360                 365

Thr Pro Leu Pro Gly Gly Thr Leu Gly Val Val Asp Ala Leu Arg Glu
370                 375                 380

Asp Ala Gly Val Ile Val Arg Ala Thr Pro Arg Ser Leu Val Leu Asn
385                 390                 395                 400

Pro Ala Leu Val Met Asp Arg Ala Thr Ala Asp Glu Val Ala Asp Gly
                405                 410                 415
```

```
Leu Asp Ser Val Leu Arg Arg Leu Ala Pro Asp Gly Arg Ile Gly Ala
        420                 425                 430

Ala Pro Arg Arg Gly
        435

<210> SEQ ID NO 4
<211> LENGTH: 818
<212> TYPE: PRT
<213> ORGANISM: Streptomyces Clavuligerus

<400> SEQUENCE: 4

Val Tyr Glu Cys Ser Asp Glu Val Arg His Asp Val Pro Gly Leu Pro
  1               5                  10                  15

Gly Pro Ser Pro Ser Ile Thr Val Leu Gly Cys Leu Gly Val Arg Ala
             20                  25                  30

Asp Gly Arg Lys Leu Glu Leu Gly Pro Pro Arg Gln Arg Ala Val Phe
         35                  40                  45

Ala Leu Leu Leu Ile Asn Ala Gly Ser Val Val Pro Val Asp Ser Ile
     50                  55                  60

Val Phe Arg Ile Trp Gly Asn Ser Pro Pro Gly Ala Val Thr Ala Thr
 65                  70                  75                  80

Leu Gln Ser Tyr Val Ser Arg Leu Arg Lys Leu Leu Ala Glu Cys Val
                 85                  90                  95

Leu Pro Asp Gly Ser Thr Pro Glu Leu Leu His Gln Pro Pro Gly Tyr
            100                 105                 110

Thr Leu Ala Leu Gly Thr Glu His Ile Asp Ala Asn Arg Phe Glu Gln
        115                 120                 125

Ala Ile Arg Thr Gly Arg Arg Leu Ser Arg Glu Glu Gln His Gln Glu
    130                 135                 140

Ala Arg Ala Val Leu Cys Gln Ala Leu Leu Ser Trp Gly Gly Thr Pro
145                 150                 155                 160

Tyr Glu Glu Leu Ser Ala Tyr Asp Phe Ala Val Gln Glu Ala Asn Arg
                165                 170                 175

Leu Glu Gln Leu Arg Leu Gly Ala Val Glu Thr Trp Ala His Cys Cys
            180                 185                 190

Leu Arg Leu Gly Arg Asp Glu Val Met Asp Gln Leu Lys Pro Glu
        195                 200                 205

Val Gln Arg Asn Pro Leu Arg Glu Arg Leu Ile Gly Gln Leu Met Gln
    210                 215                 220

Ala Gln Tyr Arg Leu Gly Cys Gln Ala Asp Ala Leu Arg Thr Tyr Glu
225                 230                 235                 240

Ala Thr Arg Arg Ala Leu Ala Glu Glu Leu Gly Thr Asp Pro Gly Lys
                245                 250                 255

Glu Leu Ala Ala Leu His Ala Ala Ile Leu Arg Gln Asp Asn Gly Leu
            260                 265                 270

Asp Arg Val Val Pro Ala Ser Ala Pro Ser Ala Gly Val Gly Arg
        275                 280                 285

Gly Ala Val Thr Val Ser Val Pro Ala Gln Arg Ser Arg Pro Leu Thr
    290                 295                 300

Arg Pro Val Ala Gly Arg Ala Arg Val Pro Gly Ala Met Thr Val Ala
305                 310                 315                 320

Ala Gly Ala Gly Ala Ala Pro Ala Ser Ala Ser Gly Ser Val Ser Ala
                325                 330                 335

Ser Val Ser Gly Ser Gly Ser Gly Ser Ala Pro Ala Ser Val
            340                 345                 350
```

```
Pro Thr Phe Phe Pro Gly Ser Val Ser Gly Ser Ala Ser Val Ala Ala
        355                 360                 365

Ser Val Ala Ala Pro Val Ser Gly His Val Ser Gly Pro Gly Ser Ala
        370                 375                 380

Phe Gly Ser Val Ala Leu His Arg Pro Gln Thr Leu Arg Gly Glu Pro
385                 390                 395                 400

Val His Gly Gly Ala Gln Gly Met Arg Thr Gly Gln Val Phe Pro Thr
                405                 410                 415

Leu Pro Pro Phe Val Gly Arg Gly Asp Glu Leu Arg Gly Leu Leu Glu
            420                 425                 430

Ser Ala Thr Ser Ala Phe His Thr Ser Gly Arg Val Ala Phe Val Val
            435                 440                 445

Gly Glu Ala Gly Ser Gly Lys Thr Arg Leu Leu Ser Glu Leu Glu Arg
        450                 455                 460

Ser Val Pro Asp Ser Val Arg Thr Val Trp Ala Ser Cys Ser Glu Ser
465                 470                 475                 480

Glu Asp Arg Pro Asp Tyr Trp Pro Trp Thr Thr Val Leu Arg His Leu
                485                 490                 495

Tyr Ala Met Trp Pro Glu Arg Met His Gly Phe Pro Gly Trp Leu Arg
            500                 505                 510

Arg Ala Leu Ala Glu Leu Leu Pro Glu Val Gly Pro Glu Pro Gln Gly
            515                 520                 525

Pro His Ser Pro Asp Gly Gly Glu Glu Asn Ser Gly Asn Gly Asp Gly
        530                 535                 540

Ala Gly Asp Gly Asp Ser Thr Pro Ala His Thr Leu Thr Leu Ala Pro
545                 550                 555                 560

Ala Leu Ala Pro Pro Arg Ser Arg Glu Ala Arg Phe Thr Leu His Asp
                565                 570                 575

Ala Val Cys Gln Ala Leu Leu Arg Thr Val Arg Glu Pro Val Val Ile
            580                 585                 590

Met Leu Glu Asp Met Glu Arg Ala Asp Ala Pro Ser Leu Ala Leu Leu
            595                 600                 605

Arg Leu Leu Val Glu Gln Leu Arg Thr Val Pro Leu Leu Leu Val Val
        610                 615                 620

Thr Thr Arg Thr Phe Arg Leu Ala His Asp Ala Glu Leu Arg Arg Ala
625                 630                 635                 640

Ala Ala Val Ile Leu Gln Ser Thr Gly Ala Arg Arg Val Leu Leu Asn
                645                 650                 655

Ala Leu Asp Ala Arg Ala Thr Gly Glu Leu Ala Gly Gly Met Leu Gly
            660                 665                 670

Lys Ala Pro Asp Thr Leu Leu Val Arg Ala Leu His Glu Arg Ser Ala
            675                 680                 685

Gly Asn Pro Tyr Phe Leu Val Gln Leu Leu Arg Ser Leu Arg Gln Gly
        690                 695                 700

Leu Ala Ala Ala Trp Glu Thr Glu Ile Pro Asp Glu Leu Ala Gly Val
705                 710                 715                 720

Val Leu Gln Arg Leu Ser Ser Val Pro Pro Ala Val Arg Arg Val Leu
                725                 730                 735

Asp Ile Cys Ala Val Val Glu Arg Ser Cys Glu Arg Arg Val Ile Glu
            740                 745                 750

Thr Val Leu Arg His Glu Gly Ile Pro Leu Glu Asn Val Arg Thr Ala
            755                 760                 765
```

```
Val Arg Gly Gly Leu Glu Glu Asp Pro Asp Pro Gly Arg Leu
        770             775             780
Arg Phe Val His Pro Leu Val Arg Glu Ala Val Trp Asp Asp Leu Glu
785             790             795             800
Asn Thr Arg Arg Pro Val Ser Arg Ser Ser Ala Leu Gly Ala Leu Ala
                805             810             815
Thr Val
```

<210> SEQ ID NO 5
<211> LENGTH: 1330
<212> TYPE: DNA
<213> ORGANISM: Streptomyces Clavuligerus

<400> SEQUENCE: 5

```
gtgcccggct ccggactcga agcactggac cgtgccaccc tcatccaccc caccctctcc      60
ggaaacaccg cggaacggat cgtgctgacc tcggggtccg gcagccgggt ccgcgacacc     120
gacggccggg agtacctgga cgcgagcgcc gtcctcgggg tgacccaggt gggccacggc     180
cgggccgagc tggcccgggt cgcggccgag cagatggccc ggctggagta cttccacacc     240
tgggggacga tcagcaacga ccgggcggtg gagctggcgg cacggctggt ggggctgagc     300
ccggagccgc tgaccgcgt ctacttcacc agcggcgggg ccgagggcaa cgagatcgcc     360
ctgcggatgg cccggctcta ccaccaccgg gcgggagt ccgcccgtac ctggatactc      420
tcccgccggt cggcctacca cggcgtcgga tacggcagcg gcggcgtcac cggcttcccc     480
gcctaccacc agggcttcgg cccctccctc ccggacgtcg acttcctgac cccgccgcag     540
ccctaccgcc gggagctgtt cgccggttcc gacgtcaccg acttctgcct cgccgaactg     600
cgcgagacca tcgaccggat cggcccggag cggatcgcgg cgatgatcgg cgagccgatc     660
atgggcgcgg tcggcgccgc ggccccgccc gccgactact ggccccgggt cgccgagctg     720
ctgcactcct acggcatcct gctgatctcc gacgaggtga tcacggggta cgggcgcacc     780
gggcactggt tcgccgccga ccacttcggc gtggtcccgg acatcatggt caccgccaag     840
ggcattcacc tcggggtatg tgccgcacgg cgccgtcctg accaccgagg ccgtcgccga     900
cgaggtcgtc ggcgaccagg gcttcccggc gggcttcacc tacagcggcc atgccacggc     960
ctgcgcggtg gccctggcca acctggacat catcgagcgc gagaatctgc tcgacaacgc    1020
cagcaccgtc ggcgcctacc tgggcaaacg cctggccgag ctgagcgatc tgccgatcgt    1080
cggggacgtc cggcagaccg gtctgatgct cggtgtcgaa ctggtcgccg accgcggaac    1140
ccgggagccg ctgccggggcg ccgccgtcgc cgaggccctg cgcgagcggg cgggcatcct    1200
gctgcgcgcc aacggcaacg ccctcatcgt caaccccccg ctgatcttca cccaggaaga    1260
cgccgacgaa ctcgtggcgg gcctgcgctc cgtactcgcc cgcaccaggc cggacggccg    1320
ggtgctctga                                                           1330
```

<210> SEQ ID NO 6
<211> LENGTH: 3345
<212> TYPE: DNA
<213> ORGANISM: Streptomyces clavuligerus

<400> SEQUENCE: 6

```
atgaagtacg acataacccc accatccggc cttcggttcg acctcctcgg cccgttgacc      60
gtgaccgccg cgagcaacc cgtggacctg ggcgcgccac ggcagcgcgc cctgctcgcc     120
ctgctgctca tcgatgtcgg caacgtggtc ccgctgccgg tcatgaccgc gtcgatctgg     180
```

```
ggggccgacc caccgtcccg ggtccggggg acgctccagg cttatgtgtc ccgactgcgg      240
aaactcctgc accgccatga ccgttccctt cgccttgtcc accagctcca ggggtatctc      300
ctcgaagtgg attcggcgaa ggtggacgcc gtggttttcg agacacgtgt cagggagtgc      360
cgggaattga gcagggcccg gaaccccgag gccacccggg ccgtggcctg gtccgccctg      420
gagatgtgga agggcacacc catgggcgag ctgcatgatt atgaatttgt ggcggcggag      480
gccgaccggc tggaaggaat ccggttacgc gcgctgagaa cctggtccca ggcgtgtctc      540
gatctccagc actatgaaga ggttgcattt cagctcggcg aggagatcca ccgcaatccg      600
gaactggaac ggctgggcgg tctcttcatg cgggcccagt atcattccgg acggtcggcg      660
gaagccctgt tgacgtatga acgtatgcgt accgcggtgg cggagaatct ggggggccgat      720 atcagtccgg agtccaggaa actccatgga aagattctgc ccaggaact cacggagaca      780 cccgccgcgc gatcgacggc ctccctcaca cgggcggcgg gccgcacgg gccccgccc      840 ctggccgaaa ccggcacccc cgccgcaccc gcggacatgg ccgaaaccac ggtggcggag      900
gaaagcgccg cgccccccgc ccggcggcg cccgggaccc cgccccccat gccgtccccc      960
gtaccgctcc cccatccgtc aggggccgtc ccgccggtca ccccggtgcc tcccccggtc     1020
ccccgctcgg ccctccgttc agcggcaccc gccgagaccg aggacccgga accggcgccg     1080
cccccctccc ctccgccggg cggccgactc atcggccgcc cgccgaact gcgcaggctg     1140 cggctgctgc tgacgaagac ccgcgcgggc cacggccatg tcctgctggt ctgcggcgaa     1200
cagggcatcg ggaagacccg gctcctggag cacaccgagc acaccctggc cgcgggcgcg     1260
ttccgggtgg tccgttcgca ctgcgtcgcc accctcccgg caccgggcta ctggccctgg     1320
gagcacctcg tacgccagct cgaccccgac agcggcctcg gtgacgacgg cgacgccgac     1380
cccgtcgccc aggccgagtg gctgccggaa caccacctca cccaccagat gcggatctgc     1440
cggacggtgc tcgccgcggc gcggcggacc ccgctcctgt tgatcctgga ggatctgcac     1500
ctcgcccacg cgccggtcct ggatgtgctc cagctcctgg tcaaacagat cggccaggcc     1560
cccgtcatgg tcgtcgccac cctgcgcgag cacgatctcg cccgggaccc cgccgtccgc     1620
cgggccgtgg gccgcatcct ccaggcgggc aacaccggca ccctccggct ggacgggctc     1680
accgaggagc agagccggga gctgatcgtc tcggtcgcgg gggccccgtt cgcgccccat     1740
gacgcccaac ggctccagcg cgcctcgggc ggcaacccgt ttctgctgct cagcatggtc     1800 acagggagg acggcacccca ggagtgggca cggccgtgcg tcccgttcga ggtgcgcgag     1860
gtgctgcacg agcggctgag cgaatgctcc ccgtccaccc aggacgtgct cacgctctgc     1920
gccgtgctcg gcatgagcgt gcgccgaccg ctgctcaccg acatcatgtc cacgctcgac     1980
atcccgcaca ccgcgctcga cgacgcgctc ggcacggggc tgctgcgcca cgaccggaac     2040
accgacggaa tggtccactt cgcccatggg ctgacccggg acttcctgct cgacgacacc     2100
ccgccggtca cccgcgcccg ctggcaccac cgggtcgccg ccaccctcgc cctgcgcttc     2160
cagcagggcg acgaccacgc cgagatccgc cgccactgtc tggccgcggc ccgtctgctc     2220
ggcgcccgcg cggggtgcg ccccctgctg gcgctggccg accgggagca gtcccgcttc     2280
tcccacgcgg aggcgctgcg ctggctggag agcgcggtcg cggtcgtcgc ggcgctgccc     2340
cgggaccagc cggtgtccgc cgtcgaactc cagttgcgca aacggatgat ggcgctgcac     2400
gcgctgatgg acggctatgg atcggcccgc gtcgagacgt tcctctccca ggtcacccag     2460
tgggaacacg tcttcgacaa cacccagccc accgggctgc tgcacgtcca ggcgctgagc     2520
gcgctcacca cgggccgcca tgagcaggcg gcggagctgg ccgggctgct gcacgagctg     2580
```

```
gccgaccacg gcggcggacc ggaggcccgg tcggcggcct gctatgtgga cggcgtcacc    2640
ctgtatgtgg gcggacgggt cgacgaagcc ctcgccgcgc tcgcccaggg caccgagatc    2700
acggacgccc tcctggccgg acaccgcagg accgccgccc cgcacggcgg cgggcacctc    2760
caggaccggc gtatcgactt ccgcgcctat ctggcgctcg gccactgtct cagcggcgac    2820
cggattcaga cccagcgcta ccggacggaa ctcctccacc tcacccagtc ggaacggtac    2880
gaccggccgt gggaccgggc cttcgcccgc tatgtgacg cgctcatcgc cgtcacggag     2940
tgcgatgtcc aggggtgtg gctggccgcg cgggcggggc tcgacctcgc cgcccgctgc     3000
cagctcccgt tctggcagcg gatgctcgcc gtccccctcg gctgggccga ggtccaccag    3060
ggggcgcacg acaaggggct ggcccggatg cgggaggcgc tgcacgaggc ggcccggcac    3120 cggacccctgc tgcgccgtac gctccacctc ggcctgctcg ccgacgccct ccagtacacg   3180
ggcgcccggg aacaggcccg cgcacgatg tcctccgccg tacgggagat cgagcgccgc     3240
ggcgagtact tctgtctccg gccgcagtgg ccctgggccc ggctcctcca cagccacggc    3300
acctccgccg cggcggagca ccgggtcgtc cacggcaggc actga                    3345

<210> SEQ ID NO 7
<211> LENGTH: 1035
<212> TYPE: DNA
<213> ORGANISM: Streptomyces clavuligerus

<400> SEQUENCE: 7
atgtcccgct ctccgcccga gtccccggcc ggttccgtgt ccgccgcggt tccgcgtccg      60
ccggtccgcg ccctgcggga ccttccggtc agtgcccagg ggctcggctg cctgccgacc     120
accgacttct acggacgccc ggaccgcgcc cgggcgacgg ccaccatccg cgccgccgtc     180
gacgccgggg tcaccctgct ggacaccgcc gacgtccagg ggctcggcgc cggtgaggag    240
ctgctcggac gggcggtcgc gggccgccgg gacgaggtgc tgatcgccac caagttcggc    300
atggtgcgct cgtccgacgg cgcctcccag ggcttgtgcg gcgagccgtc ctacgtccgc    360
gcggcctgcg aacggtccct gcgtcgtctc ggcaccgacc gcatcgacct gtactaccag    420
cactggacgg acccggcggt gccgatcgag gagaccgtgg gtgcggtggc cgagctggtg    480
cgcgagggca aggtccgcag gctcggtctc tccgagccct ccgcggccac gctgcgccgg    540
gcggacgcgg tgcacccggt gacggcggtg cagagcgagt ggagcctgtg gtcgcgcggg    600
atcgaggacg aggtggtgcc cgtctgccgg gagctgggga tcgggatcgt cgcttacgcc    660
cctctgggac ggggttttct caccggcacc atccgcacca ccgacgatct ggggacgag     720 gacttccgcc ggggccagcc ccggttcagc gctccggccc tcgcgcgcaa ccgctcgttg    780
ctgcaccggc tgcgcccggt cgcggacggt ctggggctga ccctggcaca gctcgcgctc    840
gcctggctgc accaccgggg cgaggacgtc gtcccgatcc cgggcaccgc gaacccggcc    900
catctcgcgg acaatctcgc cgccgcctcg atcggctgg acgaccggtc cctcgcggag    960
gtgacgcccg cgatctccca cccggtgtcc ggggagcggt acaccccggc attgctcgcc   1020
atgatcggca actga                                                    1035

<210> SEQ ID NO 8
<211> LENGTH: 456
<212> TYPE: DNA
<213> ORGANISM: Streptomyces clavuligerus
```

```
<400> SEQUENCE: 8
atgtccgtgg catcggccgg tatgacggac gagcagcgca aggcggtcat caccgcgtac    60
ttcaaggcgt tcgacaacgg cggcgtcggc agcgacggca ccccgcgat cgactacttc    120 gccgaggacg cggtcttctt cttccccaag tggggtctgg ccccggggcaa gtccgagatc    180 gcccggctct cgacgacct cggggggcacc atccgctcga tcacccacca tctgtggtcc    240
gtcaactgga ttctgaccgg gaccgaactc ctcgccgcga agggcaccac ccacggtgag    300
caccgggacg ggccgtggcg ggcgggtgac cccgagtggg ccgccgggcg ctggtgcacg    360
gtctacgagg tgcgggactt cctcgtccac cgggccttcg tctatctgga ccccgattac    420
gcgggcaagg acaccgcgcg ttacccgtgg ctgtga                              456

<210> SEQ ID NO 9
<211> LENGTH: 567
<212> TYPE: DNA
<213> ORGANISM: Streptomyces clavuligerus

<400> SEQUENCE: 9
gtgacccggc ctccgggcct ttccgcgcac acccacgggt ccgtgtccgg gagtctgctg    60
cgccgggtgg cgggccacta tcccaccggg gtggtcctgg tcaccggtcc ggccgaggct    120
ccggggcagc cgccgcccgc catggtggtg gggacgttca cctcggtgtc gctcgatccg    180
gtgctggtgg gtttcctccc ggccaggtcg tcgacgacct ggccgcggct ccgggcggcc    240
gggcgtttct gcgtcaatgt gctcggcgcg gatcagggcc cggtctgccg gagtttcgcc    300
gggggcgatc cggggcgctg ggaggtgccg taccggacga cggccaccgg ctcccccgtc    360
ctgctcgacg cgctcgcgtg gttcgactgc gaggtggcgg gggagacgga ggcgggcgac    420
cactggttcg tcaccggggc ggtgcgcgac ctcggggtga tccgcgaggg ttcgcccctg    480
gtcttcctgc ggggcgacta cgggcactgg gccgggggcg gcggctcggg ccgggcgggg    540
cggcggtccg ccgtctgccc ggtctga                                        567

<210> SEQ ID NO 10
<211> LENGTH: 987
<212> TYPE: DNA
<213> ORGANISM: Streptomyces clavuligerus

<400> SEQUENCE: 10
gtggaatgcc gcatattcga gatcgacgaa ctgccgttgc tggacgggga ggtcctgcgg    60
gacgcccgga tcggttacgc catgtacggc acgccgaacg ccgacgggac gaacgtggtg    120
ctctgtccgt cgttcttcgg ccgggaccac accgggtacg actggctgat cggtgcgggg    180
ctgccgctgc acaccggcg gtactgcgtc gtcaccgccg gactcttcgg caacggggtc    240
tccagctcgc ccggcaacca cccgtcgggg tcccgctttc cgctgatcac tccgcaggac    300
aatgtcgcgc gcagcaccg gctgctcacc gaggagctgg gggtacggga actggccctg    360
gtcacgggct ggtcgatggg cgcggcccac gcctaccagt gggccgtgtc gcatccgggg    420
atggtgcgcc ggatcgcccc gatctgcggg gcgccggtga gcagcccgca cagcctggtc    480
ctgctgtccg gtctggccgc ggcgctcagc gccgacgccg gggagcgggg gcggaaggcg    540
gcgggccggg tgttcgccgg gtgggggacc tcgcgttcct tctgggcccg ccgtgcccac    600
cgggagctgg gtttcgccac ccgcgaggag tacctcaccg gcttctggga gcaggtcttc    660
ctctccgggc ccggcgccgc ggatctgctc accatggtgc gcacctggga gaacacggat    720
gtgggggcga caccccgggc cgggggggagc gtcgaggcgg cgctggcctc cgtcacggcg    780
```

-continued

```
cggcccgtgg tgctgccggg cgccctggac gtgtgtttcg ccgtcgagga cgagaagcgg      840
gtggccgatc tgctgccgta tgcctcgctg gaggtgatcc cggagtgtg ggggcatctc       900 gcggggtccg gggggtcggc cgccgaccgg gagttcatcg ggggcgcgct gcggcggctg      960
ctggacagcc cggtggacgg gggctga                                          987
```

<210> SEQ ID NO 11
<211> LENGTH: 1185
<212> TYPE: DNA
<213> ORGANISM: Streptomyces clavuligerus

<400> SEQUENCE: 11

```
gtgaagtcca ttctcttcta tctgccaacg gtcggcagtc atgcgcaggt ccagcggggt        60
atggcggggg tcaatccgca gaactaccag aacatgctcc ggcagctcac ccggcaggcg      120
caggcggccg acgaactcgg ctactgggga ctgtccttca ccgagcacca cttccacacc      180
gagggtttcg aggtctccaa caacccgatc atgctgggc tctacctcgg catgcagacc        240
cggcacatcc gggtcggcca gatggccaac gtcctgccgc tgcacaatcc gctgcggctg      300
gccgaggatc tggcgatgct cgaccacatg cccggggcc gcgccttcgt cgggatcgcg        360
cgcgggttcc agaagcgctg gccgacatc atggggcagg tgtacggggt cggcggcacc       420
ctgtccgacg ccggggagcg ggaccggcgc aatcgtgccc tcttcgagga gcactgggag      480
atcatcaaga aggcgtggac gaccgagacg ttcacccact ccggggagca gtggacgatc      540
ccggtgccgg acctggagtt cccctacgag gcggtgcgcc gctacggccg gggcctcgac      600
gagaacggcg tcatccgcga ggtgggcatc gcgcccaagc cctaccagcg ccccaccccg      660
cccgtcttcc agccgttcag cttcagtgag gacacgttcc ggttctgtgc ccgggagggc      720
gtggtgccga tcctgatgaa caccgacgac cagatcgtcg cccggctgat ggacatctac      780
cgggaggagg ccgaggcggc gggccacggc accctgcggc ggggcgagcg ggtcggggtg      840
atgaaggacg tcctggtctc ccgggactcc ggcgaggccc accactgggc gtcccgcggc      900
ggcggcttca tcttcgagaa ctggttcggc cccatgggct tcaccgaggc gctgcgcgcg      960
accggcgaga cgggtccgat cggctcggac tacaagaccc tggtcgaccg ggggctggag     1020
tgggtcggca ccccgacga catcaaccgc atgatcgaga agctggtgga gcggcacgat     1080
ccggagtatc tgctccagtg ccagtactcc gggctgatcc gcacgatgt ccagctgcgc      1140 agcctggagc tgtgggccac cgagatcgcc cccaactggc tctga                    1185
```

<210> SEQ ID NO 12
<211> LENGTH: 1668
<212> TYPE: DNA
<213> ORGANISM: Streptomyces clavuligerus

<400> SEQUENCE: 12

```
tcagatggcc agggcggcga aaccgccgga ctgaagtcg taggccaccg gtacctcgat        60
caggaacggg cggccgagtc cggcgccctt ggtgagggcg cgagcagcg aggtgcggtc       120 ggtggcgcgg acgcctcgc agccgttggc ctcggcgagc tggacgaagt cgacgcttcc      180
gaagccgacg gcggggcgt gggagcgctg gtgtccgagg ttctggtaca gctcgatcag      240
gccgttgcgg tcgttgttga cgacgaccat gacgatcggc aggcccaggc gcacggccgt      300
ctcgatgtcg gcgctgttgg agtggaagcc ccgtcgccc gcgatgagga agacgggctc      360
gccgggccgg gcgatctggg cggccatggc ggcgggcagt ccgtagccga agctggagca      420
gcccgcggag gtgaggaatc cgtacggctg gtcggacttg gcgaagagca cgccgtagtg      480
```

```
gcggaagaag ccgatgtcgc tgacgaaggt gccgttgtcg aggacggagt tcatgcagtc      540
gatcacctgg tggacccgca tgccgtcctc gtactcggtg gggtcggcga ggaattcggc      600
gacgcgggcg cgcagggcgc tgaggtcgtg ccgggtcttg ggggcgaggc ccgaggtcgc      660
gtcgtcgagc gcggtgacga attcggcgac gttggtgacg atgtcgatgt cggcgcggaa      720
cagctccggg atcgggttga cctcggggc gaccccggacc gtggtcttgg cccggccccg      780
cgtccacatg gagggcgca ggtcctcggc gtagtcgtag ccgatcgcca ggaggaggtc      840
ggcggggccg aagatctcgt cgagggccgg gtggccgaga atgccgtcca tgtagccgct      900 gatgcgccg tagttgagcg gtggtcgtg cggcaggacg cccttggcgg tgtaggtggt      960
gacgacgggg atgttcagcc gctcggcgag gcgcgcagg gcgtcgacgg ccccggcgcg      1020
gatgacggcg ctaccgacga cgaggagggg gttctcggcc tcgcgcacca gctcagcggc      1080
ctcgtcgagg cgggcgcgcc agtcggcgtc cagggcgtgg gtggcggtgg cccggaccag      1140
gggggcgtcg gtggggtgc cgttcagctc ggcgccgagg aggtcgaccg gcaggctgat      1200
gaagctggga cccacgggct cgatccggct gttgaggacg gcgctgtcga cgaggttgac      1260
gatgtcctcg ccgcgttcga gctggacgct gaacttggtc agcgggccca tcacggcggt      1320
gctgtccagg cactggtggg tgacgttggg gtagcagtcg tacgactcgg actgcgcggc      1380
cagcgcgatg accgagctgc ggtccagggc ggaggtggcg acgccggtgg ccaggttggt      1440
catgccgggg cccagggtcg cgaagcacgc ctggggggcgg ttggtgatcc gggcgaggac      1500
gtccgccatc accccggcgg tgaactcgtg ccgggtcagg acgaagtcga gtccttcgac      1560
ctcgtcgaag agaatggcgg acgcctcccg gccgacgacg ccgaatacat ggtcgacacc      1620
gtactggtga agacgttcca gcatggcttt cgcggtcgtg gtggccat                  1668

<210> SEQ ID NO 13
<211> LENGTH: 1584
<212> TYPE: DNA
<213> ORGANISM: Streptomyces clavuligerus

<400> SEQUENCE: 13
tcatacgacc acccggccct ggagcctgag cctgcgcacc gcgtcgacgg agcgccgcac       60
cgtctcgccg aagtccacgt cctccggcgg caccgtgtcg atgaccaccg cgtcgtacag      120
gcgccgtgcc atgcgcccct tgacggccgt cacctcgtcg cgccggatcc cttcggcgag      180
gagcagtccg gtccacgcgc tggtggtgcc ggacccctcg tggatgccca gcttggggcg      240
ggccacggtc tcggcgggca gcaggccgga gagggcctgc cgcaacaccc acttgtcggt      300
gccccgccgg cgtttgagcc cgggttcgag ggagaccagc gcgtccagga ccgcgcggtc      360
ccagtacggg tgggtggtcc acttcccggc gatgcccgcg aggacggggg acatctcgtt      420
gaggccgtcg aagcccgcca tgtcgcccgc gatctcgtcg tcgagggacc agagcgaggc      480
cgtgcgccgg tgcataccgc cgagcgggat gtcggcgccg tacccggtga ggatgcggag      540
cggcccggtg tcgagccgcc ggtagagggc gacgagcggc agcaggtact ccaggaccgt      600
ggggtcggtg atctccgcgg cggcgaccgc ccagggcagt tccctgacga gttcggccga      660
gtggagccgg atctcgctgt gcgcggtgcc caggtggacg gcgaccgagc gggccgcgtc      720
gaactcgtcg gacacctcgg tgcccatcga cacggaccgt gtcccgggtg ccagggccgc      780
cgtgtgggcg gcgactcccc cggagtcgat gccgccggac aggacgacgg tggggccgc      840 ctccccgccg cgcagccggg tcggaccgc cgtggcgagg cgttcgccga ccaggtccac      900
cgcctcccgt tcgccgggca gcgcccggga gagcgggggt gtccaggtgc ggaccgccct      960
```

```
ggcggtgatg tcggagccgc cgactccgtg cagcaggagg gcggtccegg cggggacccg    1020 gcagacgccc gccgcccccg gcgcggtgtg ggtgccggac aggcccagcg gccggcccgg    1080
ctcgtgcgcc agggtcttcg cctcggtggc ggcgctcagc cccgtcacgt cggcgcgcag    1140
ccacagcggt accgaaccgg cgtggtcggt ggccgcgacg gtcgcgccgg tggaggcgtc    1200
ggtgagcagt gcggcgaacc gtccgttcag gagccgaag gccccgggc cccagcgccg      1260 ccaggcggcc agcagcagtt cggcgtcgcc gagggcggca gaggagccgc cgagcgctcc    1320
ggtcagctcg gcgcggttgt acagctcgcc cgccaggagc agccggacct ggccgtcggc    1380
gaccaggacg ggcggacggc ccaggtcac ggccgttccg ctccagagcg ggtacgcggt     1440
gccgtcgtgc acggggacat gggtcccgcg gacggcgaag cggggtgcgc tgccgggttc    1500
ggagtgaccg ccggggccgc cgccggggcg ccctcggtg ccgatgcgca cccggaatcc     1560
gtacacgagg tcggggccgg gcat                                           1584

<210> SEQ ID NO 14
<211> LENGTH: 1056
<212> TYPE: DNA
<213> ORGANISM: Streptomyces  clavuligerus

<400> SEQUENCE: 14 ctaccccac cgctgcccgg cgaagtccac ggcgctctcg gcgtccaccg cgtccaccgc       60
gttctcggcg ttctcggcgt cgtccgccgc cgccccggt ggcagggag agtccaccgg      120 tgccgacgcg ggcgacgtgg tggcgcgggc gtactggtag agcagttcgg ccccgatctc    180
cgccgccagc agggaggtga tccccgacgg gtcgtacgcc ggggacacct cgaccacgtc    240
gaagccgacg ggcctgagct gcccgaccac gtcgagcagg gtcagcacct cgcgcgagga    300
cagcccgccg ggggccggtg tgccggtgcc cggggcgtac gccgggtcga cgacgtcgat    360
gtcgacggag acgtacagcg gcaggccgcc gacggtgcgc cggatctgct cggcgatgcc    420
gcgcggtgag cgccgggtga agtcggcggc ggtgacgatg ctgacgccgt gcccgcgcgc    480
gtagtccagg gagtcgggcc gcggattgtg gccgcggatg ccgacctgga ccaggcgctc    540
cgggtccacc aggccctctt cgatggccca gcggaagggg gtgccgtggt ggtaggtgcc    600
gccgtagacg ggtgggttgg tgtcgctgtg cgcgtccagg tgcaggacgg cgacccggcc    660
gtggcgggcg tgcacggcgc gcagggcggc cagggagagc gagtggtccc cgcccagcat    720
caggaacgcg tcgttgcgtt ccaggagccg ggtcagggcg accgtcgcgg tgtccatcgc    780
caggtccatc gagaagggc tgaggtcgat gtcgcccccg tcgaccacgt cgatccggtc    840
gaagacccct gggccccggt cgatgccgac gccgtggatc aggctggact cgtgccggat    900
ggcgcgcggc gcgaaccgcg cgccgggccg gtagctggtg cctccgtcgt acggggcgcc    960
gacgaccacc acgtcatggc cgatcgggtc gggccggtgg cgcagccgca tgaaggtcgc   1020
cggttgggcg tagcgcgggg agacggcggt ggacac                             1056

<210> SEQ ID NO 15
<211> LENGTH: 1176
<212> TYPE: DNA
<213> ORGANISM: Streptomyces clavuligerus

<400> SEQUENCE: 15
atgcgtgcct cttcgcccag agggttccgc gtgcaccacg gtcacgccgg gatcagggg      60 tcccacgcgg acctgccgt catcgcctcc gacgttcccg cggcggtcgg cgcggtgttc     120 accgttcgc ggttcgccgc gccgagtgtg ctgctcagcc gggacgcggt cgccgacggg     180
```

-continued

```
atcgcccggg gcgtggtggt gctgtccggc aacgccaacg ccgggacggg ccgcgggg      240 tacgaggacg ccgcggaggt gcgccatctg gtggccggga tcgtcgactg cgacgagagg     300
gatgtgctga tcgcctccac gggacccgtc ggcgagcggt atccgatgtc ccgtgtccgg     360
gcccatctgc gggcggtgcg cgggccctta ccgggtgccg acttcgacgg cgcggcggcg     420
gccgtgctgg gcaccgcggg cgcccgtccc acgatccggc gggcgcggtg cggcgacgcg     480
acgctgatcg gtgtcgccaa gggcccgggt acggcccgg cggagcagga cgaccggtcg      540
acgctggcgt tcttctgcac ggacgccag gtgagcccg tcgtcctcga cgacatcttc       600
cgccgggtcg cggaccgcgc cttccacggg ctgggcttcg gcgccgacgc ctccaccggc     660
gacacggcgg ccgttctcgc caacgggctc gcgggccggg tggacctcgt cgcgttcgaa     720
caggtcctgg gcgcgctggc gctggacctg gtcaggacg tcgtccggga cagcggctgc      780
ggcggcgccc tggtcacggt gcgggtcacc ggggcccacg acaccgagca ggccgggcgc     840
gtgggccggg cggtggtcga cgcgccgtcg ctgagggccg cggtgcacgg cccggcaccc     900
gactgggcgc cggtcgccgc cgtggcgggt ggacacgggg acgaaggccc cggccggtct    960
cccgggcgga tcacgatccg ggtcggcggc cgggaggtct tccccgcccc ccgcgaccgg    1020
gcccgcccgg acgccgtcac cgcgtatccg cacggcggcg aggtgaccgt ccatatcgac    1080
ctcggtgtcc cgggccgggc gcccggccgcg ttcacggtcc acggctgcga cctcctggcg  1140
gggtacccgc gcctcggcgc cggccgggcc gtctga                             1176

<210> SEQ ID NO 16
<211> LENGTH: 13313
<212> TYPE: DNA
<213> ORGANISM: Streptomyces clavuligerus

<400> SEQUENCE: 16
ccatgggagc agcatcgcag tgcgcctccc cggccgccat gccgctagct ggtagtcccc      60
ctgccgggtg ccgaccgccg gggcggtccc gggtgcggcg gccggatcta gtcggtgtgc    120
tccgacggtg cctgctgggt gaggggcagt gtcaggcgga tggtggttcc cgcgccgggc    180
gggctgtgca gccgcagttg gccgccgagt gcctccaccc ggtcggtgag gccgacgagg    240
cccgagcccc ggcaggggc ggcgccaccg cggccgtcgt cgcggatgcc gacgtggagc     300
cgtccgtccc gggtggccac atggacgtcg acgacggtgg caccggagtg cttggcggcg    360
ttggtcaggg cctcggagac ggcgtagtac gcgcggtct cgaccggttc ggggtggcgt    420
tccccggtct ggatgtcgag ccggaccggg atggcggagc ccgggccag ggccttgagc    480 gccgggcgga gtccgccctc ggcgagtacc gccgggtgga tgccccgggc gacctcccgg    540
agttcgtcga cggcggcggc cagcccgtcg gtcacctcgt cgagctgccg gatcagctcg    600
tcggcgtcga gcggcaccga cagttgcacg gtgcgcaccc gcagcgccag ggagaccagg    660
cgctgttggg ggccgtcgtg caggtcgcgt tcgatacggc ggcgggcggt gtcggcggcg    720
gcgacgatcc gggccgtga cgcggtgagg gccgcctgcg tctccgcgtt ggcgatggcg     780
gtggccacca gttcggtgaa gccggccagc cgtcctcgg tgtccgacgg catcggcttg     840
tcgttcatcg acgccacgct gagcgcgccc cacagttgtc cgtcgacgtt gatcggcatg    900
cacaccgtgg cgcggaatcc ccactccttg ccgacgacg aggccgggcc cgaggacacg     960
gccgcgtagt cgtcgatccg cgccgggcag cccgactcga acaccagggt gtgcacattc    1020
cggccgccgg gcgtacctg gataccggcg ggaaaatcac ggccggtcct ggtccaggcg     1080
gcgacataca gggcggttcc gttgggctcg taacggccga ggaccgcgaa gtcggccgag    1140
```

```
aggagctgtc cggcctcggc ggcgaccgcg gcgaacacct ccttcggcgg tgccgcccgc   1200
gcgaccaggg tcgccacgcg ccgcagcgcc gcctgctcct cggcggcccc ccgcagctcc   1260
acacgtgcct gggtgttcgc gatggcggtg gccacgaggt cggtgaaacc ggccagccgg   1320
tcctcggtgt cgggcggcag cggttccgcg gtcagcgaga tcgccatcat cacgcccac    1380
agccgtccct cgacgttgat cggcacgccg acgaccgaac cgaagccgcg cgccctggcg   1440
aagtcggcgg gtgccccgga cgactcggcg gcgtcgtcga tccgggccgg ccgccccgtc   1500
tcggacacca gcgtcaccac gttccggccg tcggggtcca cccgggtgcc gatggggaag   1560
agcgggccgt gcagacttct ggaccagccg ccgacgcgc tcgccatgcc gtccggatcg    1620
agcctgatga ttccggtcac atcgttgccg agcagttctc cgacttcggc ggcgaccgtc   1680
gcgaacatct gttccggtgg ggtggccctg gccaccaggg tcgccacccg tcggagtgcc   1740
gcccgctcct cgacgatctg ttcgcacgac acgaccgctg ccaggccccc ctacccgccc   1800
gatgacgccc gcataccggg tatcacggca catcagcatg acgtccgccg tgaacgcccg   1860
tcaacgtggc ccgccggagt cgggaacacg cgtccggaat cagcccccgg aacggcggga   1920
ccgtcttcct ccgtccggcg cggggcactg cgccgcggcg gaatccgccc tgacctcggg   1980
agtttgcagc tagctggaat cagcggttcg ggttggtggg aagggatgtt ggccgctggc   2040
ggcgatgcgg aagccgatcg ttcccagtac ttctgggaag tgcgtcgcgg agagtcggtc   2100
cgcttccccg agtgggccgc gacgacgctg cgggttctcc acggggggaga gatccgcgaa   2160
ccggcgaagg agctgccgtg tcggacgtct tcgcatccga gaagagttcg cccggtgtcc   2220
ggacccgcgc ggcaacgtcc ccaccgcgct ctgtcatcag cgccgtcggc gccgtcagcc   2280
acgcagagaa gatcggatac gcagtgtacg agtgcagcga tgaggttcgt cacgacgtcc   2340
ccggcctgcc gggtccgtca ccgtccatca ccgtcctggg ctgtctgggc gtacgcgccg   2400
acggccggaa actggagctg ggccctccgc gtcagcgggc cgttttcgcc ctgctgctca   2460
tcaacgcggg cagtgtggtg ccggtcgact cgatcgtctt ccgtatctgg ggcaactcac   2520
caccgggcgc ggtcaccgcg acgctccagt cctatgtgtc ccggctgcgg aaactcctgg   2580
ccgagtgtgt gctcccggac ggttcgacac ccgaactgct gcaccagccg ccgggctaca   2640
ccctcgcgct cggcaccgag cacatcgacg cgaaccgttt tgagcaggcc atcaggacag   2700
ggcgccggct ctcgcgcgag gagcagcacc aggaggcgcg ggccgtgctc tgccaggccc   2760
tgctgagctg gggcgggaca ccgtacgagg agctgagcgc gtacgacttc gccgtccagg   2820
aggccaatcg gctggagcag ctccggctgg gcgccgtgga gacatgggcg cactgctgtc   2880
tgcggctggg gcgggacgag gaggtgatgg accagctcaa gccggaggtg cagcgcaatc   2940
cgctgcggga gcggctgatc gggcagctca tgcaggcgca gtaccggctg gggtgccagg   3000
cggacgcgct caggacgtac gaggcgacgc ggcgggccct ggccgaggag ctggggaccg   3060
atccgggcaa ggagctggcg gcgctgcacg cggcgatcct gcgtcaggac aacggtctgg   3120
accgcgtcgt cccggcgtcc gcgccgccgt cggcggggt cggcggggg gccgtgacgg     3180
tgtcggtccc ggcacagcgg tcgaggccgt tgacgcggcc ggtggcgggg cgggcgcggg    3240
tcccgggggc gatgacggtg gcggcgggcg cggggcggc cccgcgtcc gctccggct      3300
ccgtttccgc gtccgtttcc ggctccggct ccggctccgg ctcgctcct gcgtcggttc    3360
ccaccttctt tccggctccg gtttctggct cggcgtccgt tgccgcgtcc gtagccgcgc   3420
ccgtttccgg ccatgtctcc gggcccgggt ccgctttcgg gtccgtggcg ctccaccggc   3480
cgcagaccct ccggggcgag ccggtccacg ggggcgcgca ggggatgcgc accgggcagg   3540
```

```
tgttccccac gctgccgccg ttcgtcgggc gcggcgacga gctgcgcggt ctgctggagt    3600
ccgcgacgtc cgcgttccac acctcggggc gggtggcgtt cgtcgtcggc gaggcgggca    3660
gcggcaagac ccggctcctc tccgagttgg agcgctcggt tccggacagt gtgcgcaccg    3720
tctgggcgtc ctgttcggag agtgaggacc ggcccgacta ctggccgtgg acgaccgtgc    3780
tgcggcatct gtacgcgatg tggccggaac gtatgcacgg attccccggt tggctgcggc    3840
gcgcactcgc ggaactgctt cccgaggtgg gcccggagcc acaggggccg cactcccccg    3900
acggggcga ggagaacagc ggcaacgggg acggtgcggg cgacggggac agcaccccgg     3960
cgcacaccct cacgctcgcg cccgctctcg cgccccgcg ctccagagag gctcgtttca     4020
ccctgcacga cgccgtgtgc caggcgcttc tgcgcacggt ccgcgaaccc gtggtgatca    4080
tgctggagga catggagcgg gccgacgccc cctcgctcgc cctgctgcgc ctcctggtgg    4140
agcaactgcg caccgtcccc ctgctgctcg tggtcaccac gcgcaccttc cggctcgcgc    4200
acgacgccga gctgcgacgg gccgccgccg tgatcctcca gtcgaccggc gcgcgccggg    4260
tcctgctgaa cgccctggac gcacgggcca ccggggaact cgccggaggg atgctgggca    4320
aggccccgga caccctcctc gtacgggccc tgcacgagcg ctccgccggg aacccgtact    4380
tcctcgtcca gctcctccgc tcgctccggc aggggctcgc cgccgcctgg gagacggaga    4440
tcccggacga gctggccggg gtcgtgctgc aacggctgtc gagcgtgccg cccgccgtgc    4500
gccgggtgct cgacatctgc gcggtcgtgg agcgcagttg cgaacggcgt gtgatcgaga    4560
ccgtgctgcg ccatgaggga atcccgctgg agaacgtccg tacggcggtc cgcggcggtc    4620
tgctggagga agaccccgac gaccccgggc ggctgaggtt cgtgcatccg ctggtccggg    4680
aggccgtctg gacgacctg gagaacaccc gtcggcccgt gtcccgttcc tccgcgctcg     4740
gggcgctggc cacggtctga gtcccgggcc ccggggtcct cggcggcggg cggcgcttgc    4800
gcgctccccg acgccgggct tgatccccgg gggcagccgg acgcgcagcc gggtgcaagg    4860
ggcggtgccg acactgggcg ggcggcggcc gtggccggtc gccgccccc acggcccacc     4920
gaggagcccc cattggacac gtacgcagcg gatacgtacc cgcggtccgg cacccacccc    4980
gagccgcgtc ccgacgcacc tccccacgcg cgtcccggga cccgtcccgg cacccgttcc    5040
gagccgcgcc cggacccggg cgccgaggcc gcgtggctgc tcgcggcgga ccgcgcccat    5100
atgttccacc cggtcctgcc ccggggccgc gaggaccgca ccgttctggt ctccggccgc    5160
ggctgcaccg tacgggacac cgaagggcgc acctatctcg acgcctcgtc ggtgctcgga    5220
ctgacccaga tcggccatgg acgtgaggag atcgcgcagg ccgccgccga gcagatgcgg    5280
acactcggtc acttccacac ctggggcacc atcagcaacg acaaggccat ccgactggcc    5340
gcgcgcctca ccgacctggc gccccagggt ctccagcgcg tctacttcac cagcggcggc    5400
ggcgagggcg tcgagatcgc cctgcgcatg gcccgttact ccaccaccg caccggcagc     5460
ccggagcgca cctggatctt gtcgcgccgc accgcctacc acggcatcgg ctacggcagc    5520
ggtacggtgt cgggctcgcc cgcctaccag gacgggttcg gcccggtgct gccccatgtg    5580
caccacctca cgccgcccga cccgtaccac gccgagctgt acgacggcga ggacgtcacg    5640
gagtactgcc tgcgcgaact cgcccgcacc atcgacgaga tcggccccgg gcggatcgcc    5700
gcgatgatcg gggagccggt catgggcgcg ggcggcgccg tcgtcccgcc gccggactac    5760
tggccgcgcg tcgccgcgct gctgcgctcc cacggcatcc tgctgatcct ggacgaggtc    5820
gtcaccgcgt tcgccgcac ggggacctgg ttcgcggccg agcacttcgg ggtgaccccc     5880
gatctgctgg tgaccgcgaa gggcatcacc tccgggtatg tcccgcacgg ggcggtgctc    5940
```

```
ctgaccgagg aggtcgcgga cgccgtgaac ggggagacgg ggttcccgat cggcttcacc    6000
tataccggtc accccacggc gtgcgccgtc gcgctcgcca atctcgacat catcgaacgg    6060
gaagggctgc tggagaacgc ggtgaaggtg ggcgaccacc tcgccggggcg gctggcggcc    6120 ctgcgcgggc tgcccgccgt gggggacgtc cggcaactgg gcatgatgct cgccgtcgag    6180
ctggtgtcgg acaagacggc ccgcaccccg ctgccggggcg gcaccctcgg ggtcgtggac    6240
gcgctgcgcg aggacgcggg cgtcatcgtc cgggccacgc cgcgctccct ggtcctcaat    6300
ccggcgctcg tgatggaccg ggccacggcg gacgaggtgg cggacgggct ggactcggtg    6360
ctgcggcggc tggcacccga cgggcggatc ggcgcggccc ccggcgggg gtgacgagac    6420 cgcgggccgc cacccgcggg gggcgccggg tcggcacagc ggccgacccg cgccttccc    6480 cgtttcccgg cgccttttcc gtgccccggc gccgttcccg tgcccctgc ccctgccccct    6540 gctcgggcgc tcctccctcc gctgtggcgc cgttcccgtt ccagcgcgct gtcgagccgc    6600
cgccaagcgc cccgtgccac ggtgggagac cgccgcccga cggggcgcgc ggagccggc    6660 aagccgaagg gaagtcccgt ccgatgcgtg cctcttcgcc cagagggttc cgcgtgcacc    6720
acggtcacgc cgggatcagg gggtcccacg cggacctcgc cgtcatcgcc tccgacgttc    6780
ccgcggcggt cggcgcggtg ttcacccgtt cgcggttcgc cgcgccgagt gtgctgctca    6840
gccgggacgg ggtcgccgac gggatcgccc ggggcgtggt ggtgctgtcc ggcaacgcca    6900
acgccgggac gggcccgcgg gggtacgagg acgccgcgga ggtgcgccat ctggtggccg    6960
ggatcgtcga ctgcgacgag agggatgtgc tgatcgcctc cacgggaccc gtcggcgagc    7020
ggtatccgat gtcccgtgtc cgggcccatc tgcgggcggt gcgcgggccc ttaccgggtg    7080
ccgacttcga cggcgcggcg gcggccgtgc tgggcaccgc gggcgccgt cccacgatcc    7140 ggcgggcgcg gtgcggcgac gcgacgctga tcggtgtcgc caagggcccg ggtacgggcc    7200
cggcggagca ggacgaccgg tcgacgctgg cgttcttctg cacggacgcc caggtgagcc    7260
ccgtcgtcct cgacgacatc ttccgccggg tcgcggaccg cgccttccac gggctgggct    7320
tcggcgccga cgcctccacc ggcgacacgg cggccgttct cgccaacggg ctcgcgggcc    7380
gggtggacct cgtcgcgttc gaacaggtcc tgggcgcgct ggcgctggac ctggtcaggg    7440
acgtcgtccg ggacagcggc tgcgcggcgc ccctggtcac ggtgcgggtc accggggccc    7500
acgacaccga gcaggccggg cgcgtgggcc gggcggtggt cgacgcgccg tcgctgaggg    7560
ccgcggtgca cggcccggca cccgactggg cgccggtcgc cgccgtggcg ggtggacacg    7620
gggacgaagg ccccggccgg tctcccgggc ggatcacgat ccggtcggc ggccgggagg    7680 tcttccccgc cccccgcgac cgggcccgcc cggacgccgt caccgcgtat ccgcacggcg    7740
gcgaggtgac cgtccatatc gacctcggtg tcccggggccg ggcgcccggc gcgttcacgg    7800
tccacggctg cgacctcctg gcggggtacc cgcgcctcgg cgccggccgg gccgtctgaa    7860
cgggcgctcc cggcggacg cgaccgcga gggcgcggga gcgcagggaa cacgggagcg    7920
ggcccggtgg tcgatcggcc accgggcccg ctcccgtcgt tccgtccgct gtccccggcc    7980
gccctacccc caccgctgcc cggcgaagtc cacggcgctc tcggcgtcca ccgcgtccac    8040
cgcgttctcg gcgttctcgg cgtcgtccgc cgccgcccc ggtggcaggg gagagtccac    8100
cggtgccgac gcgggcgacg tggtggcgcg gcgtactgg tagagcagtt cggccccgat    8160
ctccgccgcc agcagggagg tgatccccga cgggtcgtac gccggggaca cctcgaccac    8220
gtcgaagccg acgggcctga gctgcccgac cacgtcgagc agggtcagca cctcgcgcga    8280
ggacagcccg ccgggggccg gtgtgccggt gcccggggcg tacgccgggt cgacgacgtc    8340
```

```
gatgtcgacg gagacgtaca gcggcaggcc gccgacggtg cgccggatct gctcggcgat   8400
gccgcgcggt gagcgccggg tgaagtcggc ggcggtgacg atgctgacgc cgtgcccgcg   8460
cgcgtagtcc agggagtcgg gccgcggatt gtggccgcgg atgccgacct ggaccaggcg   8520
ctccgggtcc accaggccct cttcgatggc ccagcggaag ggggtgccgt ggtggtaggt   8580
gccgccgtag acgggtgggt tggtgtcgct gtgcgcgtcc aggtgcagga cggcgacccg   8640
gccgtggcgg gcgtgcacgg cgcgcagggc ggccagggag agcgagtggt ccccgcccag   8700
catcaggaac gcgtcgttgc gttccaggag ccgggtcagg gcgaccgtcg cggtgtccat   8760
cgccaggtcc atcgagaagg ggctgaggtc gatgtcgccc ccgtcgacca cgtcgatccg   8820
gtcgaagacc cctgggcccc ggtcgatgcc gacgccgtgg atcaggctgg actcgtgccg   8880
gatggcgcgc ggcgcgaacc gcgcgccggg ccggtagctg gtgcctccgt cgtacggggc   8940
gccgacgacc accacgtcat ggccgatcgg gtcgggccgg tggcgcagcc gcatgaaggt   9000
cgccggttgg gcgtagcgcg gggagacggc ggtggacacc ctggccgttc ccgcgcacc    9060 cggccctgct cccgttcccg taccgacgcc cggccacccc gtgcgggctc ccgttcccgt   9120
gccgaccccg gttcccgaac gggctcccgt tcccgcgtgg aatcccgttc ccgcgcccgc   9180
ggcgccgtcc gggccgcggc tgcccctccc tccgagaccg ctcctgccgt tcctgcggcc   9240
gttgccgctc tgcgggccgg tgccgcgcc cacgcccgct gcaccgtccg cgccgccgcc   9300
ggtgccgttg ccgccgccgg tgccgttctg gccaccggtg ccgttctggc cgctcatacg   9360
accacccggc cctggagcct gagcctgcgc accgcgtcga cggagcgccg caccgtctcg   9420
ccgaagtcca cgtcctccgg cggcaccgtg tcgatgacca ccgcgtcgta caggcgccgt   9480
gccatggcgc ccttgacggc cgtcacctcg tcgcgccgga tcccttcggc gaggagcagt   9540
ccggtccacg cgctggtggt gccggacccc tcgtggatgc ccagcttggg gcgggccacg   9600
gtctcggcgg gcagcaggcc ggagagggcc tgccgcaaca cccacttgtc ggtgccccgc   9660
cggcgtttga gcccgggttc gagggagacc agcgcgtcca ggaccgcgcg gtcccagtac   9720
gggtgggtgg tccacttccc ggcgatgccc gcgaggacgg gggacatctc gttgaggccg   9780
tcgaagcccg ccatgtcgcc cgcgatctcg tcgtcgaggg accagagcga ggccgtgcgc   9840
cggtgcatac cgccgagcgg gatgtcggcc ccgtacccgg tgaggatgcg gagcggcccg   9900
gtgtcgagcc gccggtagag ggcgacgagc ggcagcaggt actccaggac cgtggggtcg   9960
gtgatctccg cggcggcgac cgcccagggc agttccctga cgagttcggc cgagtggagc  10020
cggatctcgc tgtgcgcggt gcccaggtgg acggcgaccg agcgggccgc gtcgaactcg  10080
tcggacacct cggtgcccat cgacacggac cgtgtcccgg gtgccagggc gccgtgtgg   10140 gcggcgactc ccccggagtc gatgccgccg gacaggacga cggtgggggc cgcctccccg  10200
ccgcgcagcc gggtgcggac cgccgtggcg aggcgttcgc cgaccaggtc caccgcctcc  10260
cgttcgccgg gcagcgcccg ggagagcggg ggtgtccagg tgcggaccgc cctggcggtg  10320
atgtcggagc cgccgactcc gtgcagcagg agggcggtcc cggcggggac ccggcagacg  10380
cccgccgccc ccggcgcggt gtgggtgccg gacaggccca gcggccggcc cggctcgtgc  10440
gccagggtct tcgcctcggt ggcggcgctc agcccgtca cgtcggcgcg cagccacagc   10500
ggtaccgaac cggcgtggtc ggtggccgcg acggtcgcgc cggtggaggc gtcggtgagc  10560
agtgcggcga accgtccgtt caggagccgg aaggcccgg ggcccagcg ccgccaggcg    10620 gccagcagca gttcggcgtc gccgagggcg gcagaggagc cgccgagcgc tccggtcagc  10680
tcggcgcggt tgtacagctc gcccgccagg agcagccgga cctggccgtc ggcgaccagg  10740
```

```
acgggcggac ggcccagggt cacggccgtt ccgctccaga gcgggtacgc ggtgccgtcg   10800
tgcacgggga catgggtccc gcggacggcg aagcggggtg cgctgccggg ttcggagtga   10860
ccgccgggc cgccgccggg gcggccctcg gtgccgatgc gcacccggaa tccgtacacg   10920
aggtcgggc cggcatggt gaactcgtcc tccacggtgg tcagatggcc agggcggcga   10980
aaccgccgga ctggaagtcg taggccaccg gtacctcgat caggaacggg cggccgagtc   11040
cggcgcccctt ggtgagggcg gcgagcagcg aggtgcggtc ggtggcgcgg acggcctcgc   11100
agccgttggc ctcggcgagc tggacgaagt cgacgcttcc gaagccgacg gcggggggcgt   11160
gggagcgctg gtgtccgagg ttctggtaca gctcgatcag gccgttgcgg tcgttgttga   11220
cgacgaccat gacgatcggc aggcccaggc gcacggccgt ctcgatgtcg gcgctgttgg   11280
agtggaagcc gccgtcgccc gcgatgagga agacgggctc gccggggccgg gcgatctggg   11340
cggccatggc ggcgggcagt ccgtagccga agctggagca gcccgcggag gtgaggaatc   11400
cgtacgcctg gtcggacttg gcgaagagca cgccgtagtg gcggaagaag ccgatgtcgc   11460
tgacgaaggt gccgttgtcg aggacggagt tcatgcagtc gatcacctgg tggacccgca   11520
tgccgtcctc gtactcggtg gggtcggcga ggaattcggc gacgcgggcg cgcagggcgc   11580
tgaggtcgtg ccgggtcttg ggggcgaggc ccgaggtcgc gtcgtcgagc gcggtgacga   11640
attcggcgac gttggtgacg atgtcgatgt cggcgcggaa cagctccggg atcgggttga   11700
cctcgggggc gacccggacc gtggtcttgg cccggccccg cgtccacatg gagggcgca   11760
ggtcctcggc gtagtcgtag ccgatcgcca ggaggaggtc ggcggggccg aagatctcgt   11820
cgagggccgg gtggccgaga atgccgtcca tgtagccgct gatggcgccg tagttgagcg   11880
ggtggtcgtg cggcaggacg cccttggcgg tgtaggtggt gacgacgggg atgttcagcc   11940
gctcggcgag ggcgcgcagg gcgtcgacgg ccccggcgcg gatgacggcg ctaccgacga   12000
cgaggagggg gttctcggcc tcgcgcacca gctcagcggc ctcgtcgagg cgggcgcgcc   12060
agtcggcgtc cagggcgtgg gtggcggtgg cccggaccag ggggggcgtcg gtgggggtgc   12120
cgttcagctc ggcgccgagg aggtcgaccg gcaggctgat gaagctggga cccacgggct   12180
cgatccggct gttgaggacg gcgctgtcga cgaggttgac gatgtcctcg ccgcgttcga   12240
gctggacgct gaacttggtc agcgggccca tcacggcggt gctgtccagg cactggtggg   12300
tgacgttggg gtagcagtcg tacgactcgg actgcgcggc cagcgcgatg accgagctgc   12360
ggtccagggc ggaggtggcg acgccggtgg ccaggttggt catgccgggg cccagggtcg   12420
cgaagcacgc ctgggggcgg ttggtgatcc gggcgaggac gtccgccatc accccggcgg   12480
tgaactcgtg ccgggtcagg acgaagtcga gtccttcgac ctcgtcgaag agaatggcgg   12540
acgcctcccg gccgacgacg ccgaatacat ggtcgacacc gtactggtga agacgttcca   12600
gcatggcttt cgcggtcgtg gtgggccatgg agatctcctt cgcatcggac gggcgccggg   12660
atggcgcccc ggaaaacgcg gcaccggggcg gtgcgcaccg ggtggcgcac accgtgggtg   12720
gtggcgttgc cactgtgcgg atcgcctctt ggcggcggtc ggacgccgg cttggacaga   12780
atgggcaagg cgcgttcaag gcatggcgtc catcgtcctc gtggcgcttt tcgtgaaatc   12840
cgtccggcgc cgacggtctc catccgattc cgtcccttc cgtccaccga tccgaggaga   12900
atccatggat gtcctggccg cgttggagcg caagcccagc ctgaatcttt tccccatcga   12960
gaaccggctg tcgccgcgcg ccagtgccgc gctggccacc gacgccgtca accgctatcc   13020
gtactccgag accccggtgg ccgtctacgg cgatgtcacg gggctggccg aggtgtacgc   13080
gtactgcgag gacctggcca agcgcttctt cgggggcgcgc cacgccggtg tgcagttcct   13140
```

```
gtccggtctg cacaccatgc acaccgtgct gaccgccctg accccgcccg gcgggcgcgt    13200
cctggtcctc gcgccggagg acggcggcca ctacgccacg gtgacgatct gccggggctt    13260
cggctacgag gtcgagttct taccttcgac cgccggacac ctggagatcg act           13313
```

<210> SEQ ID NO 17
<211> LENGTH: 18070
<212> TYPE: DNA
<213> ORGANISM: Streptomyces clavuligerus

<400> SEQUENCE: 17

```
ggtaccggca tccgacccag gccccgggcg caggacccgg aggcaggcac cggcacaccc      60
cggccgggcg gcccggctcc cggcggtcgg tgtccggcga cccgcaatcg gcagccgccc     120
caggcccggg acaggagccc ggctcaaggc accggccctg cgcacccgct gaggcggcag     180
gttcctgaca gccggcatcc gccagtcggc gcggggcagc cgccccaggc gcccggcccg     240
gcacacccgt gcgagcgccc ggctcccggc ggtcggtgcc ccgaggcggg cgaccggcag     300
ccggacacgg ccccgctcgg ggcgcggccc agggcacagg ccctgggcac ccgctcggac     360
gcccgttcgg acagcaggcc cgtgggaagc cgccggtcag gcccgcaggc agccaccggt     420
cggcgggcgg atcaggtgtt ggcggggggac tcgtccggga agatctttgt gacgacggtc     480
ccgtcctcgg tcagatagcc gtgcagcatc ccggggctgc tgtgcggcgc gtcgaagtcg     540 ccccggggt cgagggcgat cacgccgccc tgcccgccga gccggggcag gcgcttgacg     600
atcacctcgt aagcggcgga cgccacgccg agcccctgga actcgatcag atgggagagg     660
gtcgaggtcg ccgcgccccg gatgaacacc tcaccggcgc cggtggcgct cgcggcgacg     720
gtccggttgt cggcgtaggt cccggccccg atcagcgggg agtcgccgat ccggccgggg     780
agcttgttgg tgagcccgcc ggtggaggtg gccgccgcga gatcgccgcg ccggtcgagg     840
gccaccgcgc ccaccgtccc cgtcgactgc gcgtcggcca gtgcctccgg ggccctccgg     900
gcggcgggat cgcccgcctc ggtctccttc gcgcgcagca gcgcgtccca gcgggcctgg     960
gtccagtagt agtcctgggt gacggtgcgc agcccgtgcc gggcgccgaa gtcgtcggcg    1020
ccctcgccgg agaggaggac gtgcttcgac ttctccagca ccagccgggc gccctcgacc    1080
gggttgcgca gggaggtgac cccggcgacc gctcccgcct tcagatcgga gccccgcatc    1140
acggaggcgt ccagctcatg cccggcgtcg gcggtgaaga cggcgccctt gcccgcgttg    1200
aacagcgggt tgtcctccag ttcgcggacg gcggcctcga ccgcgtccag gctgtccccg    1260
ccgcgcgcga gcacccgctg tccggcgcgg agcgctgcgg cgagcccgtc ccggtacgcc    1320
ttctcccgtt ccgggccggt cgtctcccgg tccagggcgg ctccggcccc gccgtggacg    1380
gcgatgacca cgtcacgggc gtccggccgg ggcttccccg gcgcgctccc ccgttccttc    1440
ttctcctccc gcgcctgctg ctcctgcttc tgttgcgtcg tgtgggccgc gcggtgggt    1500 ccatggccgc ccgaggcccc gggtacgacg atgagcgtgt cgtcagcac gcggcggcg    1560 agcaggagg acgccagcca ggcggtggcg gggcggtggg gcatcgggca ctcctcggga    1620 cggggtgag agacgctccg gccgactgta ctgacatgcc catgccccct ctagtgcccc    1680
ggagccgcct tccgccctcc ccgccgcccg gcggcgcccg cccggcgcgc tcagtccagg    1740
gccaggtcct ccggggcgga gcgggcgagt ccggcgagtg tgccgagcgc ccgggtcagt    1800
tcgtccgccg acggcgacgc caggcccagc cggaccgcgt gcggtgtacg gccctgcccg    1860
gcgcagaacg cggcggcggg cgtcaccccg atcccgtgcc gcgcggcggc ggcgacgaag    1920
gtgtcggcgc gccaggggcg gggcagcacc caccagcagt ggtacgagcc ggggtcgccc    1980
```

```
gacacggcga agccgtcgag cgcgcgccgg gcgatctcct gccgtacgcc cgcgtcccgc    2040
cgcttggcgc gtaccagcgc gtcgaccgtg ccgtcggtct gccagcggac cgccgcctcc    2100
agcgcgaacc gcgcggggcc gagaccgccg gagcgcagcg cggcgccgac cgctccgtcg    2160
agccccgggg gcaccaccgc gaaccccagg gtcagcccgg gggcgagccg cttggagagg    2220
ctgtcgacga gcaccgtccg cccgggggcg accgccgcga gcggagccgt gccctcccgc    2280
aggaagcccc agacggcgtc ctcgaccgcg ggaaggtcca gccgctccag gaccgcggcg    2340
agctgggcga gacgcccgtc cgacagggtg agggagagcg ggttgtgcag ggtgggctgg    2400
acatagaccg cccggagcgg agcgctccgg ttggcctcgt ccagcgcctc cggaatcacc    2460
ccgtccgcgt ccatggcgag ggggacgagc gtgatgccga gccgggccgc gatcgccttg    2520
accacggggt aggtcagctc ctcgaccccc agtcggcccc ccggcggcac cagcgcgccg    2580
agcacggcgg agagtgcctg ccgaccgttg cccgcgaaca gcacccgccg ggggtccggc    2640
cgccagccgc cccgggcgag cagcccgccg gcggcctcgc gcgcctcggg ggtcccggcg    2700
gcaccggccg gccggagcac ggactccagg acatcgggcc gcagcagccc gccgagcccg    2760
gtggccagca gcgcggcctg ctcggggacg acggggtggt tcagctccag gtcgatccgg    2820
cttccggcgg gctcggagag cgcggggccg acgcccgccc gcgccgcgcg gacataggtg    2880
ccgcgcccca cctcgccgac ggtgagccct ctgcgggcca gctcccggta gacccgggcg    2940
gcggtggagt cggcgatgcc gcacccgcgg gcgaactccc gctgcggcgg aagccggtcc    3000
ccggggcgca gcccgcccgt cctgatctcc tcggcgaccg cgtcggccac ctgccggtag    3060
tccttcatct cccgtacctc ccctgtccgg tggaccgctt cccgcccggc ccgccgacc    3120
gtgaaacgga agcaccccgt tccggagctc gagctccccg tccggaagct ccccgtccgg    3180
aagctccccg ttccagaatt gcaccgagag caatattccc tattgcaccg atcaaaacac    3240
cgatctacgc tcggaattgc ctcacacaga ccgtcgacgc atctgccgca caccggtact    3300
gacgccccgt cggaccgcac ccgcgcggag ccgtcgcccc gcccgccccg ttcgcgcaca    3360
ggagagagaa ggagatggtg gagaccagcg cactcgccgg tgtggtgatg gtcgccctcg    3420
gaatggtcct caccccggga ccgaacatga tctatctcgt ctcccgcagc atcacccagg    3480
gccgacgtgc ggggatcatc tcgctgggcg gtgtggccct cggttttctg gtctatctgc    3540
tcgccgcgaa tctcggcctg tcggtgatct tcgtcgccgt gccggagttg tatgtcgcgg    3600
tcaaactggc cggtgcggcc tatctggcat atctcgcctg gaacgccctg cggcccggtg    3660
gcgtgaatgt gttctccccc gaggaggttc cgcacgactc cccgagcagg ctgttcacca    3720
tggggctgat gacgaacatc ctcaaccccca agatcgccgt catgtatctc gcactcatcc    3780
cgcagttcgt cgacccgaac gcggaccgtg tcctgttcca ggggctgatt ctcggcggtc    3840
tccagatcgc ggtgagcgtc gcggtcaatc tcgcgatcgt gctggcggcc ggagccatcg    3900
ccgcctttct cggccgccac cccttctggc tcagggttca gcgccgcgtg atgggcgcgg    3960
cgctcggtac gctcgcggtc tccctggccc tcgacacctc cgcccccgcc gcacccgtct    4020
cctgaggccg ccgaccggg agccgacgcg aaggcacccc tgggcaaccg ttcggagagc    4080
ttatccgtta ccccatgaat cccgatataa gtgcattggc cacttaccca tgcatggaac    4140
aggccaacct gaccaaaaaa tgagccctcc ccacccggaa tagatgcttc ccagtgtgaa    4200
gaaatttcat agcgggagcg tctgccgaac aggacggccc atacgccgca aggcagaacg    4260
gacatcgccg cccgcccggg tccagaaaat tcggaggaca catcggacga ccgtctccgc    4320
atcggcgtca actcccgatt acagagaata ttgagtacgt atcaaccggg ccttgatcta    4380
```

```
ctcagcctcc attgttctct ccagtcggga tgtgcaatga agtacgacat aaccccacca    4440
tccggccttc ggttcgacct cctcggcccg ttgaccgtga ccgccggcga gcaacccgtg    4500
gacctgggcg cgccacggca gcgcgccctg ctcgccctgc tgctcatcga tgtcggcaac    4560
gtggtcccgc tgccggtcat gaccgcgtcg atctggggg ccgacccacc gtcccgggtc    4620 cggggacgc tccaggctta tgtgtcccga ctgcggaaac tcctgcaccg ccatgaccgt    4680
tcccttcgcc ttgtccacca gctccagggg tatctcctcg aagtggattc ggcgaaggtg    4740
gacgccgtgg ttttcgagac acgtgtcagg gagtgccggg aattgagcag ggcccggaac    4800
cccgaggcca cccgggccgt ggcctggtcc gccctggaga tgtggaaggg cacacccatg    4860
ggcgagctgc atgattatga atttgtggcg gcggaggccg accggctgga aggaatccgg    4920
ttacgcgcgc tggagacctg gtcccaggcg tgtctcgatc tccagcacta tgaagaggtt    4980
gcatttcagc tcggcgagga gatccaccgc aatccggaac tggaacggct gggcggtctc    5040
ttcatgcggg cccagtatca ttccggacgg tcggcggaag ccctgttgac gtatgaacgt    5100
atgcgtaccg cggtggcgga gaatctgggg gccgatatca gtccggagct ccaggaactc    5160
catggaaaga ttctgcgcca ggaactcacg gagacacccg ccgcgcgatc gacgcctcc    5220 ctcacacggg cggcgggccc gcacgggccc ccgcccctgg ccgaaaccgg cacccccgcc    5280 gcacccgcg acatggccga aaccacggtg gcggaggaaa gcgccgcgcc cccgccccg    5340 gcggcgcccg ggaccccgcc ccccatgccg tcccccgtac cgctccccca tccgtcaggg    5400
gccgtcccgc cggtcacccc ggtgcctccc ccggtccccc gctcggccct ccgttcagcg    5460
gcacccgccg agaccgagga cccggaaccg gcgccgcccc ctccccctcc gccgggcggc    5520
cgactcatcg gccgccgcgc cgaactgcgc aggctgcggc tgctgctgac gaagacccgc    5580
gcgggccacg gccatgtcct gctggtctgc ggcgaacagg gcatcgggaa gacccggctc    5640
ctggagcaca ccgagcacac cctggccgcg ggcgcgttcc gggtggtccg ttcgcactgc    5700
gtcgccaccc tcccggcacc gggctactgg ccctgggagc acctcgtacg ccagctcgac    5760
ccggacagcg gcctcggtga cgacggcgac gccgaccccg tcgcccaggc cgagtggctg    5820
ccggaacacc acctcaccca ccagatgcgg atctgccgga cggtgctcgc cgcggcgcgg    5880
cggaccccgc tcctgttgat cctggaggat ctgcacctcg cccacgcgcc ggtcctggat    5940
gtgctccagc tcctggtcaa acagatcggc caggcccccg tcatggtcgt cgccacccrg    6000
cgcgagcacg atctcgcccg ggaccccgcc gtccgccggg ccgtgggccg catcctccag    6060
gcgggcaaca ccggcaccct ccggctggac gggctcaccg aggagcagag ccgggagctg    6120
atcgtctcgg tcgcggggc cccgttcgcg ccccatgacg cccaacggct ccagcgcgcc    6180
tcgggcggca acccgtttct gctgctcagc atggtcacag gggaggacgg cacccaggag    6240
tgggcacggc cgtgcgtccc gttcgaggtg cgcgaggtgc tgcacgagcg gctgagcgaa    6300
tgctccccgt ccaccaggga cgtgctcacg ctctgcgccg tgctcggcat gagcgtgcgc    6360
cgaccgctgc tcaccgacat catgtccacg ctcgacatcc gcacaccgc gctcgacgac    6420 gcgctcggca cggggctgct gcgccacgac cggaacaccg acggaatggt ccacttcgcc    6480
catgggctga cccgggactt cctgctcgac gacacccgc cggtcacccg cgcccgctgg    6540
caccaccggg tcgccgccac cctcgccctg cgcttccagc agggcgacga ccacgccgag    6600
atccgccgcc actgtctggc cgcggcccgt ctgctcggcg cccgcgcggg ggtgcgcccc    6660
ctgctggcgc tggccgaccg ggagcagtcc cgcttctccc acgcggaggc gctgcgctgg    6720
ctggagagcg cggtcgcggt cgtcgcggcg ctgccccggg accagccggt gtccgccgtc    6780
```

```
gaactccagt tgcgcaaacg gatgatggcg ctgcacgcgc tgatggacgg ctatggatcg    6840
gcccgcgtcg agacgttcct ctcccaggtc acccagtggg aacacgtctt cgacaacacc    6900
cagcccaccg ggctgctgca cgtccaggcg ctgagcgcgc tcaccacggg ccgccatgag    6960
caggcggcgg agctggccgg gctgctgcac gagctggccg accacggcgg cggaccggag    7020
gcccggtcgg cggcctgcta tgtggacggc gtcaccctgt atgtgggcgg acgggtcgac    7080
gaagccctcg ccgcgctcgc ccagggcacc gagatcacgg acgccctcct ggccggacac    7140
cgcaggaccg ccgccccgca cggcggcggg cacctccagg accggcgtat cgacttccgc    7200
gcctatctgg cgctcggcca ctgtctcagc ggcgaccgga ttcagaccca cgctaccgg     7260 acggaactcc tccacctcac ccagtcggaa cggtacgacc ggccgtggga ccgggccttc    7320
gcccgctatg tggacgcgct catcgccgtc acggagtgcg atgtccaggg ggtgtggctg    7380
gccgcgcggg cggggctcga cctcgccgcc cgctgccagc tcccgttctg cagcggatg     7440 ctcgccgtcc ccctcggctg ggccgaggtc accaggggg cgcacgacaa ggggctggcc     7500
cggatgcggg aggcgctgca cgaggcggcc cggcaccgga ccctgctgcg ccgtacgctc    7560
cacctcggcc tgctcgccga cgccctccag tacacgggcg cccgggaaca ggcccggcgc    7620
acgatgtcct ccgccgtacg ggagatcgag cgccgcggcg agtacttctg tctccggccg    7680
cagtggccct gggccggct cctccacagc cacggcacct ccgccgcggc ggagcaccgg     7740
gtcgtccacg gcaggcactg acccgggggcc ggccggagcc gggcccgtac ggtacgggtc   7800
cggctccgga cccggcggcc cggagccggg cggggcgggg cggcccgacg gttccggggc    7860
cggcggttgt gggaggggggc ggccccccgat cgctcagacc gggcagacgg cggaccgccg  7920 ccccgccccgg cccgagccgc cgcccccggc ccagtgcccg tagtcgcccc gcaggaagac   7980
caggggcgaa ccctcgcgga tcaccccgag gtcgcgcacc gccccggtga cgaaccagtg    8040
gtcgcccgcc tccgtctccc ccgccacctc gcagtcgaac cacgcgagcg cgtcgagcag    8100
gacgggggag ccggtggccg tcgtccggta cggcacctcc cagcgccccg gatcgccccc    8160
ggcgaaactc cggcagaccg ggccctgatc cgcgccgagc acattgacgc agaaacgccc    8220
ggccgcccgg agccgcggcc aggtcgtcga cgacctggcc gggaggaaac ccaccagcac    8280
cggatcgagc gacaccgagg tgaacgtccc caccaccatg gcgggcggcg gctgccccgg    8340
agcctcggcc ggaccggtga ccaggaccac cccggtggga tagtggcccg ccacccggcg    8400
cagcagactc ccggacacgg acccgtgggt gtgcgcggaa aggcccggag gccgggtcac    8460
agccacgggt aacgcgcggt gtccttgccc gcgtaatcgg ggtccagata gacgaaggcc    8520
cggtggacga ggaagtcccg cacctcgtag accgtgcacc agcgcccggc ggcccactcg    8580
gggtcacccg cccgccacgg cccgtccggg tgctcaccgt gggtggtgcc ctccgcggcg    8640
aggagttcgg tcccggtcag aatccagttg acgaccaca gatggtgggt gatcgagcgg     8700
atggtgcccc cgaggtcgtc gaagagccgg gcgatctcgg acttgccccg ggccagaccc    8760
cacttgggga agaagaagac cgcgtcctcg gcgaagtagt cgatcgcggg ggtgccgtcg    8820
ctgccgacgc cgccgttgtc gaacgccttg aagtacgcgg tgatgaccgc cttgcgctgc    8880
tcgtccgtca taccggccga tgccacggac atgaaacgac ctccagagat tccgggtggc    8940
tgtgctgggc ctgcggaagg ggtgtccccc gcgaaggacg gcggacgccg cggacgccgc    9000
ggccgtctcc ccggcggacg ggtcccagcg tcctggagag ggcttggcgg cggcttgacg    9060
ccgtgctgtc ccgcggcttg cggaacgcga agtaccggcc agcgtacggg cgttgcaccg    9120
gacgtgtacg ccggtcggga ccccctcgtac ccccggagcc ggccgacccc ggcggctccg   9180
```

```
ggggtacgga cgcgccggac cggcccgagc gagccggacg ggtcggacgg tgcgcgtggt   9240
tccggtgtgt cggacagctc ggacggaccg gacggtgcgc gtggttccgg tgtgtcggac   9300
agctcggacg ggtcggacgg tgcgcgtggt tccggcacgc cggacgggtc agttgccgat   9360
catggcgagc aatgccgggg tgtaccgctc cccggacacc gggtgggaga tcgcggccgt   9420
cacctccgcg agggaccggt cgtccagccg gatcgaggcg gcggcgagat tgtccgcgag   9480
atgggccggg ttcgcggtgc ccgggatcgg gacgacgtcc tcgccccggt ggtgcagcca   9540
ggcgagcgcg agctgtgcca gggtcagccc cagaccgtcc gcgaccgggc gcagccggtg   9600
cagcaacgag cggttgcgcg cgagggccgg agcgctgaac cggggctggc cccggcggaa   9660
gtcctcgtcc cccagatcgt cggtggtgcg gatggtgccg gtgagaaaac cccgtcccag   9720
aggggcgtaa gcgacgatcc cgatcccag ctcccggcag acgggcacca cctcgtcctc   9780
gatcccgcgc gaccacaggc tccactcgct ctgcaccgcc gtcaccgggt gcaccgcgtc   9840
cgcccggcgc agcgtggccg cggagggctc ggagagaccg agcctgcgga ccttgccctc   9900
gcgcaccagc tcggccaccg cacccacggt ctcctcgatc ggcaccgccg ggtccgtcca   9960
gtgctggtag tacaggtcga tgcggtcggt gccgagacga cgcagggacc gttcgcaggc  10020
cgcgcggacg taggacggct cgccgcacaa gccctgggag gcgccgtcgg acgagcgcac  10080
catgccgaac ttggtggcga tcagcacctc gtcccggcgg cccgcgaccg cccgtccgag  10140
cagctcctca ccggcgccga gccctggac gtcggcggtg tccagcaggg tgaccccggc  10200
gtcgacggcg gcgcggatgg tggccgtcgc ccgggcgcgg tccgggcgtc cgtagaagtc  10260
ggtggtcggc aggcagccga gccctgggc actgaccgga aggtcccgca gggcgcggac  10320
cggcggacgc ggaaccgcgg cggacacgga accggccggg gactcgggcg gagagcggga  10380
catacggaac ctccacaggc ggagccggga acgggacgag ggcgaggacg ggacggaacg  10440
aaggagagga cgggacggac agcacggacg ggacggacgg aacggagtcg ggaaccgggg  10500
ggggtgaccg gaaccgggcc gtccttggcc ctcccccgtc ctccccgcca tccgccgttc  10560 tccccgttc cctctcccgt cctccagcca acaccgccgc cctttccaag cgcttgacac  10620
ggcaccgaca gccgccgccg ggcgcccgat ggggacccgt gcccgccggt gagcggcggt  10680
gagcgccggt acgggacccc acgcgccgcc gcccgggcgc ccgccagggc ccgcgcggcc  10740
accccggccc gccccggccg gagcggcgat ccgggccgct cgctgcaaga ggaacatcca  10800
cagccgcaca aggagcgctc cgcacagtgg gcaccacgtc cgccccgtcc cccacaccgt  10860
ggccggtccc caccggacag cacagcaccg cacagcacca catcgcacgg cacagcacag  10920
caccaccggc acgaggaacc aaggaaagga accacaccac catgacctca gtggactgca  10980
ccgcgtacgg ccccgagctg cgcgcgctcg ccgcccggct gccccggacc cccgggccg   11040 acctgtacgc cttcctggac gccgcgcaca cagccgccgc ctcgctcccc ggcgccctcg  11100
ccaccgcgct ggacaccttc aacgccgagg cagcgagga cggccatctg ctgctgcgcg  11160 gcctccggt ggaggccgac gccgacctcc ccaccacccc gagcagcacc cggcgcccg   11220 aggaccgctc cctgctgacc atggaggcca tgctcggact ggtgggccgc cggctcggtc  11280
tgcacacggg gtaccgggag ctgcgctcgg gcacggtcta ccacgacgtg taccgtcgc   11340 ccggcgcgca ccacctgtcc tcggagacct ccgagacgct gctggagttc acacggaga   11400 tggcctacca ccggctccag ccgaactacg tcatgctggc ctgctcccgg gccgaccacg  11460
agcgcacggc ggccacactc gtcgcctcgg tccgcaaggc gctgccctg ctggacgaga  11520 ggacccgggc ccggctcctc gaccggagga tgccctgctg cgtggatgtg gccttccgcg  11580
```

-continued

```
gcggggtgga cgacccgggc gccatcgccc aggtcaaacc gctctacggg gacgcggacg   11640
atcccttcct cgggtacgac cgcgagctgc tggcgccgga ggaccccgcg gacaaggagg   11700
ccgtcgccgc cctgtccaag gcgctcgacg aggtcacgga ggcggtgtat ctggagcccg   11760
gcgatctgct gatcgtcgac aacttccgca ccacgcacgc gcggacgccg ttctcgcccc   11820
gctgggacgg gaaggaccgc tggctgcacc gcgtctacat ccgcaccgac cgcaatggac   11880
agctctccgg cggcgagcgc gcgggcgacg tcgtcgcctt cacaccgcgc ggctgagctc   11940
ccgggtccga caccgcgcgg ctgaacccac ggtccggggc ccacggtccg gcaccgcgcg   12000
gctgagcccc cgggtccggc agcgggcggc tgaacccccg ccccgggcca ccgcccgacc   12060
gcccccgcgc accggacgcg cccgcctgta cggcggtccc gcccgggccc gtacacctga   12120
agcgccggc ggaccgccgc cccgccgggg gacggacaga gccgggtgcg ggaggacgtc   12180
ctcccgcacc cggctcccac cgttccgcac cgaccgcacc cgaccgtgcc gcaggcgcca   12240
ccggcaccgc accgcccgcg ccggcagcca ccacaggcgc cacgccgccc gcacggtgcc   12300
cgcgctgctc agccccgtc caccgggctg tccagcagcc gccgcagcgc gccccgatg   12360
aactcccggt cggcggccga ccccccgac cccgcgagat gccccacac tcccgggatc   12420
acctccagcg aggcatacgg cagcagatcg gccacccgct tctcgtcctc gacggcgaaa   12480
cacacgtcca gggcgcccgg cagcaccacg gcccgcgccg tgacgaggc cagcgccgcc   12540
tcgacgctcc ccccggcccc gggtgtcgcc cccacatccg tgttctccca ggtgcgcacc   12600
atggtgagca gatccgcggc gccgggcccg gagaggaaga cctgctccca gaagccggtg   12660
aggtactcct cgcgggtggc gaaacccagc tcccgtgggg cacggcgggc ccagaaggaa   12720
cgcgaggtcc cccacccggc gaacaccgg cccgccgcct tccgccccg ctccccggcg   12780
tcggcgctga gcgccgcggc cagaccggac agcaggacca ggctgtgcgg gctgctcacc   12840
ggcgccccgc agatcggggc gatcggcgc accatccccg gatgcgacac ggcccactgg   12900
taggcgtggg ccgcgcccat cgaccagccc gtgaccaggg ccagttcccg taccccagc   12960
tcctcggtga gcagccggtg ctgcgccgcg acattgtcct gcggagtgat cagcggaaag   13020
cgggaccccg acgggtggtt gccgggcgag ctggagaccc cgttgccgaa gagtccggcg   13080
gtgacgacgc agtaccgccg ggtgtccagc ggcagccccg caccgatcag ccagtcgtac   13140
ccggtgtggt cccggccgaa gaacgacgga cagagcacca cgttcgtccc gtcggcgttc   13200
ggcgtgccgt acatggcgta accgatccgg gcgtcccgca ggacctcccc gtccagcaac   13260
ggcagttcgt cgatctcgaa tatgcggcat tccaccgctg acctccttgt tcgatccccc   13320
cggacaacag gtcggtcgtg gccggagact cagagccagt tgggggcgat ctcggtggcc   13380
cacagctcca ggctgcgcag ctggacatcg tgcgggatca gccggagta ctggcactgg   13440
agcagatact ccggatcgtg ccgctccacc agcttctcga tcatgcggtt gatgtcgtcc   13500
ggggtgccga cccactccag cccccggtcg accagggtct tgtagtccga gccgatcgga   13560
cccgtctcgc cggtcgcgcg cagcgcctcg gtgaagccca tggggccgaa ccagttctcg   13620
aagatgaagc cgccgccgcg ggacgcccag tggtgggcct cgccggagtc ccgggagacc   13680
aggacgtcct tcatcacccc gaccgctcg cccgccgca gggtgccgtg gcccgccgcc   13740
tcggcctcct cccggtagat gtccatcagc cgggcgacga tctggtcgtc ggtgttcatc   13800
aggatcggca ccacgccctc ccgggcacag aaccggaacg tgtcctcact gaagctgaac   13860
ggctggaaga cggcggtg ggggcgctgg tagggcttgg gcgcgatgcc cacctcgcgg   13920
atgacgccgt tctcgtcgag gccccggccg tagcggcgca ccgcctcgta ggggaactcc   13980
```

```
aggtccggca ccgggatcgt ccactgctcc ccggagtggg tgaacgtctc ggtcgtccac   14040
gccttcttga tgatctccca gtgctcctcg aagagggcac gattgcgccg gtcccgctcc   14100
ccggcgtcgg acagggtgcc gccgaccccg tacacctgcc ccatgatgtc ggcccagcgc   14160
ttctggaacc cgcgcgcgat cccgacgaag gcgcggcccc gggtcatgtg gtcgagcatc   14220
gccagatcct cggccagccg cagcggattg tgcagcggca ggacgttggc catctggccg   14280
acccggatgt gccgggtctg catgccgagg tagagcccca gcatgatcgg gttgttggag   14340
acctcgaaac cctcggtgtg gaagtggtgc tcggtgaagg acagtcccca gtagccgagt   14400
tcgtcggccg cctgcgcctg ccgggtgagc tgccggagca tgttctggta gttctgcgga   14460 ttgaccccg ccatacccg ctggacctgc gcatgactgc cgaccgttgg cagatagaag   14520
agaatggact tcaccctggc tcctccggtt cgcggcgccc tccattgacg tgcgccgaaa   14580
gcggctcgac cgtcccactc cgcccttgag ttccgtctga cgccgcgcca gtcggcgggc   14640
cgtccgccgg ggtgccgcc ggggtccgca cccgccggac ggcacggcgc gcaccgcgcg   14700
cgcggcgctt cggggcaccg ggctcgacgg ggtgctcagc gggacgtcca acggaaggca   14760
agcccccgta cccagcctgg tcaaggcgct catcgccatt ccctgaggag gtcccgcctt   14820
gaccacagca atctccgcgc tcccgaccgt gcccggctcc ggactcgaag cactggaccg   14880
tgccaccctc atccacccca ccctctccgg aaacaccgcg gaacggatcg tgctgacctc   14940
ggggtccggc agccgggtcc gcgacaccga cggccgggag tacctggacg cgagcgccgt   15000
cctcggggtg acccaggtgg gccacggccg ggccgagctg gccgggtcg cggccgagca   15060 gatggcccgg ctggagtact tccacacctg ggggacgatc agcaacgacc gggcggtgga   15120
gctggcggca cggctggtgg ggctgagccc ggagccgctg accgcgtct acttcaccag   15180 cggcggggcc gagggcaacg agatcgccct gcggatggcc cggctctacc accaccggcg   15240
cggggagtcc gcccgtacct ggatactctc ccgccggtcg gcctaccacg gcgtcggata   15300
cggcagcggc ggcgtcaccg gcttccccgc ctaccaccag ggcttcggcc cctcccctccc   15360 ggacgtcgac ttcctgaccc cgccgcagcc ctacgccgg gagctgttcg ccggttccga   15420
cgtcaccgac ttctgcctcg ccgaactgcg cgagaccatc gaccggatcg gcccggagcg   15480
gatcgcggcg atgatcggcg agccgatcat gggcgcggtc ggcgccgcgg ccccgcccgc   15540
cgactactgg ccccgggtcg ccgagctgct gcactcctac ggcatcctgc tgatctccga   15600
cgaggtgatc acggggtacg ggcgcaccgg gcactggttc gccgccgacc acttcggcgt   15660
ggtcccggac atcatggtca ccgccaaggg catcacctcg gggtatgtgc cgcacggcgc   15720
cgtcctgacc accgaggccg tcgccgacga ggtcgtcggc gaccagggct tcccggcggg   15780
cttcacctac agcggccatg ccacggcctg cgcggtggcc ctggccaacc tggacatcat   15840
cgagcgcgag aatctgctcg acaacgccag caccgtcggc gcctacctgg gcaaacgcct   15900
ggccgagctg agcgatctgc cgatcgtcgg ggacgtccgg cagaccggtc tgatgctcgg   15960
tgtcgaactg gtcgccgacc gcggaacccg ggagccgctg ccgggcgccg ccgtcgccga   16020
ggccctgcgc gagcgggcgg gcatcctgct gcgcgccaac ggcaacgccc tcatcgtcaa   16080
ccccccgctg atcttcaccc aggaagacgc cgacgaactc gtggcgggcc tgcgctccgt   16140
actcgcccgc accaggccgg acggccgggt gctctgaccc ctttggccct ccccggcccc   16200
accggggcac caccccgccg caccccgagc gcaaaaagac ccctctgcct gcgtttccgc   16260
aggtcagagg ggtctggtgc agtggagcct agggagtcg aaccccctgac atctgccatg   16320 caaagacagc gctctaccaa ctgagctaag gccccgaagc gacagaacgg ccctggactg   16380
```

-continued

```
ctccgtcccg gccactgccg cagaccagag taccgggtgt tcccggtgat cctccaaaac    16440
attgaggtct cccggtgggc gaccactctc cgtaagatgc tcgacgtggt tcgcagcagc    16500
gaagcccgct tggggaagcg atggggagac gcgcatggac gccgctcagc aggagacgac    16560
cgcaagagcc cgggagctac agcgaagctg gtacggggag ccctgggggg ccctgttccg    16620
caggctgata gacgatctgg ggctgaacca ggcgcgtctc gcggcggtgc tgggcctctc    16680
cgcccccatg ctctcccagc tcatgagcgg ccagcgggcc aagatcggca acccggccgt    16740
ggtccaacgg gtccaggcgc tccaggagtt ggccggacag gtggccgacg gcagcgtcag    16800
cgcggtggag gccaccgacc gcatggagga gatcaagaag tcgcagggag gctccgtcct    16860
gaccgcgaac agccagacca ccaacagctc ggggcgccg accgtccgcc gggtcgtccg     16920
ggagatccag tcgctgctgc ggtccgtgtc cgccgcgggg gacatcatcg acgcggcgaa    16980
ctccctcgcc ccgacccatc cggagctggc agagttcctg cgggtgtacg ggccgggcg    17040
caccgcggac gccgtggcgc actacgagtc ccaccagagc tgacgaccga ggccggcccc    17100
ggaacggacc agagcctcat gagggacggg gagcggacgc ggcaccatgg gtgaggtctt    17160
cgccggccgt tacgagctgg tcgacccgat cggacgcgga ggggtcggcg cggtctggcg    17220
cgcctgggac caccggcgcc gccgctatgt ggcggccaag gtgctccagc agagcgacgc    17280
gcacaccctg ctgcgcttcg tccgcgagca ggccctgcgg atcgaccatc ccatgtcct    17340
ggccccggcg agctgggccg cggacgacga caaagtcctc ttcaccatgg atctcgtggg    17400
cggcggatca ctcgcgcacg tgatcggcga ctacggcccg ctcccgccgc gctatgtgtg    17460
cgccctgctg gaccaactcc tctccgggct cgccgcggtg cacgccgagg gcgtggtgca    17520
ccgcgacatc aaaccggcga acatcctgat ggaggccacc gggacgggcc gcccccatct    17580
gcgcctgtcc gacttcggca tctccatgcg caagggcgag ccccggctga ccgagaccaa    17640
ctatgtcgtg ggtacgcccg gttacttcgc ccccgagcag gtcgagggcg cggagccgga    17700
cttccccgcc gatctcttcg ccgtcggcct ggtcgccctc tatctgctgg agggtcagaa    17760
acccgacacc aaggccctgg tggacttctt caccgcccat ggcaccccg gtgctccccg     17820
ggggataccg gagccgctgt ggcaggtgct cgcggggctg atccagcccg accccgccgc    17880
ccggttccgt acggcgacgg ggcccggaa ggccctcgcc gccgccgtgg aactgcttcc     17940
cgagagcggc cccgacgacg aaccggtgga gatattcgac caactgggcc cgctgccgcc    18000
ggggttcggc cccggcggcc ccgagaacac gccgccctcc ggtctgctgc gctcggcggc    18060
ctccggtacc                                                           18070
```

<210> SEQ ID NO 18
<211> LENGTH: 1668
<212> TYPE: DNA
<213> ORGANISM: Streptomyces clavuligerus

<400> SEQUENCE: 18

```
atggccacca cgaccgcgaa agccatgctg gaacgtcttc accagtacgg tgtcgaccat      60
gtattcggcg tcgtcggccg ggaggcgtcc gccattctct tcgacgaggt cgaaggactc     120
gacttcgtcc tgacccggca cgagttcacc gccggggtga tggcggacgt cctcgcccgg     180
atcaccaacc gccccaggc gtgcttcgcg accctgggcc ccggcatgac caacctggcc      240
accgcgtcg ccacctccgc cctggaccgc agctcggtca tcgcgctggc cgcgcagtcc      300
gagtcgtacg actgctaccc caacgtcacc caccagtgcc tggacagcac cgccgtgatg     360
ggcccgctga ccaagttcag cgtccagctc gaacgcggcg aggacatcgt caacctcgtc     420
```

-continued

```
gacagcgccg tcctcaacag ccggatcgag cccgtgggtc ccagcttcat cagcctgccg      480
gtcgacctcc tcggcgccga gctgaacggc accccccaccg acgcccccct ggtccgggcc    540
accgccaccc acgccctgga cgccgactgg cgcgcccgcc tcgacgaggc cgctgagctg     600
gtgcgcgagg ccgagaaccc cctcctcgtc gtcggtagcg ccgtcatccg cgccggggcc     660
gtcgacgccc tgcgcgccct cgccgagcgg ctgaacatcc ccgtcgtcac cacctacacc     720
gccaagggcg tcctgccgca cgaccacccg ctcaactacg cgccatcag cggctacatg      780 gacggcattc tcggccaccc ggccctcgac gagatcttcg ccccgccga cctcctcctg      840 gcgatcggct acgactacgc cgaggacctg cgcccctcca tgtggacgcg gggccgggcc     900
aagaccacgg tccgggtcgc ccccgaggtc aacccgatcc cggagctgtt ccgcgccgac     960
atcgacatcg tcaccaacgt cgccgaattc gtcaccgcgc tcgacgacgc gacctcgggc   1020
ctcgccccca agacccggca cgacctcagc gccctgcgcg cccgcgtcgc cgaattcctc    1080
gccgacccca ccgagtacga ggacggcatg cgggtccacc aggtgatcga ctgcatgaac   1140
tccgtcctcg acaacggcac cttcgtcagc gacatcggct tcttccgcca ctacggcgtg   1200
ctcttcgcca agtccgacca gccgtacgga ttcctcacct ccgcgggctg ctccagcttc   1260
ggctacggac tgcccgccgc catggccgcc cagatcgccc ggcccggcga gccgtcttc    1320 ctcatcgcgg gcgacggcgg cttccactcc aacagcgccg acatcgagac ggccgtgcgc   1380
ctgggcctgc cgatcgtcat ggtcgtcgtc aacaacgacc gcaacggcct gatcgagctg    1440
taccagaacc tcgacacca cgctcccac gccccccgcg tcggcttcgg aagcgtcgac      1500
ttcgtccagc tcgccgaggc caacggctgc gaggccgtcc gcgccaccga ccgcacctcg    1560
ctgctcgccg ccctcaccaa gggcgccgga ctcggccgcc cgttcctgat cgaggtaccg   1620
gtggcctacg acttccagtc cggcggtttc gccgccctgg ccatctga                1668
```

<210> SEQ ID NO 19
<211> LENGTH: 1583
<212> TYPE: DNA
<213> ORGANISM: Streptomyces clavuligerus

<400> SEQUENCE: 19

```
atgcccggcc ccgacctcgt gtacggattc cgggtgcgca tcggcaccga gggccgcccc    60
ggcggcggcc ccggcggtca ctccgaaccc ggcagcgcac cccgcttcgc cgtccgcggg   120
acccatgtcc ccgtgcacga cggcaccgcg tacccgctct ggagcggaac ggccgtgacc   180
ctgggccgtc cgcccgtcct ggtcgccgac ggccaggtcc ggctgctcct ggcgggcgag   240
ctgtacaacc cgccgagct gaccgagcg ctcggcggct cctctgccgc cctcggcgac    300
gccgaactgc tgctggccgc ctggcggcgc tggggccccg ggccttccg gctcctgaac   360 ggacggttcg ccgcactgct caccgacgcc tccaccggcg cgaccgtcgc ggccaccgac   420
cacgccggtt cggtaccgct gtggctgcgc gccgacgtga cggggctgag cgccgccacc   480
gaggcgaaga ccctggcgca cgagccgggc cggccgctgg gcctgtccgg cacccacacc    540 cgccggggc ggcgggcgtc tgccgggtcc ccgccgggac cgcccctcctg ctgcacggag   600 tcggcggctc cgacatcacc gccagggcgg tccgcacctg gacaccccccg ctctcccggg   660 cgctgcccgg cgaacgggag gcggtggacc tggtcggcga acgcctcgcc acggcggtcc   720
gcacccggct gcgcggcggg gaggcggccc ccaccgtcgt cctgtccggc ggcatcgact   780 ccggggggagt cgccgcccac acggcggccc tggcaccgg gacacggtcc gtgtcgatgg    840
```

-continued

```
gcaccgaggt gtccgacgag ttcgacgcgg cccgctcggt cgccgtccac ctgggcaccg    900
cgcacagcga gatccggctc cactcggccg aactcgtcag ggaactgccc tgggcggtcg    960
ccgccgcgga gatcaccgac cccacggtcc tggagtacct gctgccgctc gtcgccctct   1020
accggcggct cgacaccggg ccgctccgca tcctcaccgg gtacggcgcc gacatcccgc   1080
tcggcggtat gcaccggcgc acggcctcgc tctggtccct cgacgacgag atcgcgggcg   1140
acatggcggg cttcgacggc ctcaacgaga tgtccccgt cctcgcggc atcgccggga    1200
agtggaccac ccaccgtac tgggaccgcg cggtcctgga cgcgctggtc tccctcgaac    1260
ccgggctcaa cgccggcgg ggcaccgaca agtgggtgtt gcggcaggcc ctctccggcc    1320
tgctgcccgc cgagaccgtg gcccgcccca gctgggcat ccacgagggg tccggcacca    1380
ccagcgcgtg gaccggactg ctcctcgccg aagggatccg gcgcgacgag gtgacggccg    1440
tcaagggcgc catggcacgg cgcctgtacg acgcggtggt catcgacacg gtgccgccgg    1500
aggacgtgga cttcggcgag acggtgcggc gctccgtcga cgcggtgcgc aggctcaggc    1560
tccagggccg ggtggtcgta tga                                           1583
```

<210> SEQ ID NO 20
<211> LENGTH: 1056
<212> TYPE: DNA
<213> ORGANISM: Streptomyces clavuligerus

<400> SEQUENCE: 20

```
gtgtccaccg ccgtctcccc gcgctacgcc caaccggcga ccttcatgcg gctgcgccac     60
cggcccgacc cgatcggcca tgacgtggtg gtcgtcggcg ccccgtacga cggaggcacc    120
agctaccggc ccggcgcgcg gttcgcgccg cgcgccatcc ggcacgagtc cagcctgatc    180
cacggcgtcg gcatcgaccg ggggcccaggg gtcttcgacc ggatcgacgt ggtcgacggg    240
ggcgacatcg acctcagccc cttctcgatg gacctggcga tggacaccgc gacggtcgcc    300
ctgacccggc tcctggaacg caacgacgcg ttcctgatgc tgggcgggga ccactcgctc    360
tccctggccg ccctgcgcgc cgtgcacgcc cgccacggcc gggtcgccgt cctgcacctg    420
gacgcgcaca gcgacaccaa cccacccgtc tacggcggca cctaccacca cggcaccccc    480
ttccgctggg ccatcgaaga gggcctggtg gaccccgagc gcctggtcca ggtcggcatc    540
cgcggccaca atccgcggcc cgactccctg gactacgcgc gcgggcacgg cgtcagcatc    600
gtcaccgccg ccgacttcac ccggcgctca ccgcgcggca tcgccgagca gatccggcgc    660
accgtcggcg gcctgccgct gtacgtctcc gtcgacatcg acgtcgtcga cccggcgtac    720
gccccgggca ccggcacacc ggccccggc gggctgtcct cgcgcgaggt gctgaccctg    780
ctcgacgtgg tcgggcagct caggcccgtc ggcttcgacg tggtcgaggt gtccccggcg    840
tacgacccgt cggggatcac ctccctgctg gcggcggaga tcggggccga actgctctac    900
cagtacgccc gcgccaccac gtcgcccgcg tcggcaccgg tggactctcc cctgccaccg    960
ggggcggcgc cggacgacgc cgagaacgcc gagaacgcgg tggacgcggt ggacgccgag   1020
agcgccgtgg acttcgccgg gcagcggtgg gggtag                             1056
```

<210> SEQ ID NO 21
<211> LENGTH: 441
<212> TYPE: PRT
<213> ORGANISM: Streptomyces clavulgerus -continued

<400> SEQUENCE: 21

```
Val Pro Gly Ser Gly Leu Glu Ala Leu Asp Arg Ala Thr Leu Ile His
 1               5                  10                  15

Pro Thr Leu Ser Gly Asn Thr Ala Glu Arg Ile Val Leu Thr Ser Gly
            20                  25                  30

Ser Gly Ser Arg Val Arg Asp Thr Asp Gly Arg Glu Tyr Leu Asp Ala
        35                  40                  45

Ser Ala Val Leu Gly Val Thr Gln Val Gly His Gly Arg Ala Glu Leu
50                  55                  60

Ala Arg Val Ala Ala Glu Gln Met Ala Arg Leu Glu Tyr Phe His Thr
65                  70                  75                  80

Trp Gly Thr Ile Ser Asn Asp Arg Ala Val Glu Leu Ala Ala Arg Leu
                85                  90                  95

Val Gly Leu Ser Pro Glu Pro Leu Thr Arg Val Tyr Phe Thr Ser Gly
            100                 105                 110

Gly Ala Glu Gly Asn Glu Ile Ala Leu Arg Met Ala Arg Leu Tyr His
        115                 120                 125

His Arg Gly Glu Ser Ala Arg Thr Trp Ile Leu Ser Arg Arg Ser
130                 135                 140

Ala Tyr His Gly Val Gly Tyr Gly Ser Gly Gly Val Thr Gly Phe Pro
145                 150                 155                 160

Ala Tyr His Gln Gly Phe Gly Pro Ser Leu Pro Asp Val Asp Phe Leu
                165                 170                 175

Thr Pro Pro Gln Pro Tyr Arg Arg Glu Leu Phe Ala Gly Ser Asp Val
            180                 185                 190

Thr Asp Phe Cys Leu Ala Glu Leu Arg Glu Thr Ile Asp Arg Ile Gly
        195                 200                 205

Pro Glu Arg Ile Ala Ala Met Ile Gly Glu Pro Ile Met Gly Ala Val
210                 215                 220

Gly Ala Ala Ala Pro Ala Asp Tyr Trp Pro Arg Val Ala Glu Leu
225                 230                 235                 240

Leu His Ser Tyr Gly Ile Leu Leu Ile Ser Asp Glu Val Ile Thr Gly
                245                 250                 255

Tyr Gly Arg Thr Gly His Trp Phe Ala Ala Asp His Phe Gly Val Val
            260                 265                 270

Pro Asp Ile Met Val Thr Ala Lys Gly Ile Thr Ser Gly Tyr Val Pro
        275                 280                 285

His Gly Ala Val Leu Thr Thr Glu Ala Val Ala Asp Glu Val Val Gly
290                 295                 300

Asp Gln Gly Phe Pro Ala Gly Phe Thr Tyr Ser Gly His Ala Thr Ala
305                 310                 315                 320

Cys Ala Val Ala Leu Ala Asn Leu Asp Ile Ile Glu Arg Glu Asn Leu
                325                 330                 335

Leu Asp Asn Ala Ser Thr Val Gly Ala Tyr Leu Gly Lys Arg Leu Ala
            340                 345                 350

Glu Leu Ser Asp Leu Pro Ile Val Gly Asp Val Arg Gln Thr Gly Leu
        355                 360                 365

Met Leu Gly Val Glu Leu Val Ala Arg Gly Thr Arg Glu Pro Leu Pro
370                 375                 380

Gly Ala Ala Val Ala Glu Ala Leu Arg Glu Arg Ala Gly Ile Leu Leu
385                 390                 395                 400

Arg Ala Asn Gly Asn Ala Leu Ile Val Asn Pro Pro Leu Ile Phe Thr
                405                 410                 415
```

```
Gln Glu Asp Ala Asp Glu Leu Val Ala Gly Leu Arg Ser Val Leu Ala
            420                 425                 430

Arg Thr Arg Pro Asp Gly Arg Val Leu
            435                 440

<210> SEQ ID NO 22
<211> LENGTH: 188
<212> TYPE: PRT
<213> ORGANISM: Streptomyces Clavuligerus

<400> SEQUENCE: 22

Val Thr Arg Pro Pro Gly Leu Ser Ala His Thr His Gly Ser Val Ser
  1               5                  10                  15

Gly Ser Leu Leu Arg Arg Val Ala Gly His Tyr Pro Thr Gly Val Val
             20                  25                  30

Leu Val Thr Gly Pro Ala Glu Ala Pro Gly Gln Pro Pro Ala Met
             35                  40                  45

Val Val Gly Thr Phe Thr Ser Val Ser Leu Asp Pro Val Leu Val Gly
         50                  55                  60

Phe Leu Pro Ala Arg Ser Ser Thr Thr Trp Pro Arg Leu Arg Ala Ala
 65                  70                  75                  80

Gly Arg Phe Cys Val Asn Val Leu Gly Ala Asp Gln Gly Pro Val Cys
                 85                  90                  95

Arg Ser Phe Ala Gly Gly Asp Pro Gly Arg Trp Glu Val Pro Tyr Arg
            100                 105                 110

Thr Thr Ala Thr Gly Ser Pro Val Leu Leu Asp Ala Leu Ala Trp Phe
            115                 120                 125

Asp Cys Glu Val Ala Gly Glu Thr Glu Ala Gly Asp His Trp Phe Val
        130                 135                 140

Thr Gly Ala Val Arg Asp Leu Gly Val Ile Arg Glu Gly Ser Pro Leu
145                 150                 155                 160

Val Phe Leu Arg Gly Asp Tyr Gly His Trp Ala Gly Gly Gly Ser
                165                 170                 175

Gly Arg Ala Gly Arg Arg Ser Ala Val Cys Pro Val
            180                 185

<210> SEQ ID NO 23
<211> LENGTH: 391
<212> TYPE: PRT
<213> ORGANISM: Streptomyces clavuligerus

<400> SEQUENCE: 23

Met Arg Ala Ser Ser Pro Arg Gly Phe Arg Val His His Gly His Ala
  1               5                  10                  15

Gly Ile Arg Gly Ser His Ala Asp Leu Ala Val Ile Ala Ser Asp Val
             20                  25                  30

Pro Ala Ala Val Gly Ala Val Phe Thr Arg Ser Arg Phe Ala Ala Pro
             35                  40                  45

Ser Val Leu Leu Ser Arg Asp Ala Val Ala Asp Gly Ile Ala Arg Gly
         50                  55                  60

Val Val Val Leu Ser Gly Asn Ala Asn Ala Gly Thr Gly Pro Arg Gly
 65                  70                  75                  80

Tyr Glu Asp Ala Ala Glu Val Arg His Leu Val Ala Gly Ile Val Asp
                 85                  90                  95

Cys Asp Glu Arg Asp Val Leu Ile Ala Ser Thr Gly Pro Val Gly Glu
            100                 105                 110
```

```
Arg Tyr Pro Met Ser Arg Val Arg Ala His Leu Arg Ala Val Arg Gly
            115                 120                 125

Pro Leu Pro Gly Ala Asp Phe Asp Gly Ala Ala Ala Val Leu Gly
        130                 135                 140

Thr Ala Gly Ala Arg Pro Thr Ile Arg Arg Ala Arg Cys Gly Asp Ala
145                 150                 155                 160

Thr Leu Ile Gly Val Ala Lys Gly Pro Gly Thr Gly Pro Ala Glu Gln
                165                 170                 175

Asp Asp Arg Ser Thr Leu Ala Phe Phe Cys Thr Asp Ala Gln Val Ser
            180                 185                 190

Pro Val Val Leu Asp Asp Ile Phe Arg Arg Val Ala Asp Arg Ala Phe
        195                 200                 205

His Gly Leu Gly Phe Gly Ala Asp Ala Ser Thr Gly Asp Thr Ala Ala
    210                 215                 220

Val Leu Ala Asn Gly Leu Ala Gly Arg Val Asp Leu Val Ala Phe Glu
225                 230                 235                 240

Gln Val Leu Gly Ala Leu Ala Leu Asp Leu Val Arg Asp Val Val Arg
                245                 250                 255

Asp Ser Gly Cys Gly Gly Ala Leu Val Thr Val Arg Val Thr Gly Ala
            260                 265                 270

His Asp Thr Glu Gln Ala Gly Arg Val Gly Arg Ala Val Val Asp Ala
        275                 280                 285

Pro Ser Leu Arg Ala Ala Val His Gly Pro Ala Pro Asp Trp Ala Pro
    290                 295                 300

Val Ala Ala Val Ala Gly His Gly Asp Glu Gly Pro Gly Arg Ser
305                 310                 315                 320

Pro Gly Arg Ile Thr Ile Arg Val Gly Gly Arg Glu Val Phe Pro Ala
                325                 330                 335

Pro Arg Asp Arg Ala Arg Pro Asp Ala Val Thr Ala Tyr Pro His Gly
            340                 345                 350

Gly Glu Val Thr Val His Ile Asp Leu Gly Val Pro Gly Arg Ala Pro
        355                 360                 365

Gly Ala Phe Thr Val His Gly Cys Asp Leu Leu Ala Gly Tyr Pro Arg
    370                 375                 380

Leu Gly Ala Gly Arg Ala Val
385                 390

<210> SEQ ID NO 24
<211> LENGTH: 351
<212> TYPE: PRT
<213> ORGANISM: Streptomyces clavuligerus

<400> SEQUENCE: 24

Val Ser Thr Ala Val Ser Pro Arg Tyr Ala Gln Pro Ala Thr Phe Met
1               5                   10                  15

Arg Leu Arg His Arg Pro Asp Pro Ile Gly His Asp Val Val Val
            20                  25                  30

Gly Ala Pro Tyr Asp Gly Gly Thr Ser Tyr Arg Pro Gly Ala Arg Phe
        35                  40                  45

Ala Pro Arg Ala Ile Arg His Glu Ser Ser Leu Ile His Gly Val Gly
    50                  55                  60

Ile Asp Arg Gly Pro Gly Val Phe Asp Arg Ile Asp Val Val Asp Gly
65                  70                  75                  80

Gly Asp Ile Asp Leu Ser Pro Phe Ser Met Asp Leu Ala Met Asp Thr
                85                  90                  95
```

```
Ala Thr Val Ala Leu Thr Arg Leu Leu Glu Arg Asn Asp Ala Phe Leu
            100                 105                 110

Met Leu Gly Gly Asp His Ser Leu Ser Leu Ala Ala Leu Arg Ala Val
            115                 120                 125

His Ala Arg His Gly Arg Val Ala Val Leu His Leu Asp Ala His Ser
        130                 135                 140

Asp Thr Asn Pro Pro Val Tyr Gly Gly Thr Tyr His His Gly Thr Pro
145                 150                 155                 160

Phe Arg Trp Ala Ile Glu Glu Gly Leu Val Asp Pro Glu Arg Leu Val
                165                 170                 175

Gln Val Gly Ile Arg Gly His Asn Pro Arg Pro Asp Ser Leu Asp Tyr
                180                 185                 190

Ala Arg Gly His Gly Val Ser Ile Val Thr Ala Ala Asp Phe Thr Arg
                195                 200                 205

Arg Ser Pro Arg Gly Ile Ala Glu Gln Ile Arg Arg Thr Val Gly Gly
    210                 215                 220

Leu Pro Leu Tyr Val Ser Val Asp Ile Asp Val Val Asp Pro Ala Tyr
225                 230                 235                 240

Ala Pro Gly Thr Gly Thr Pro Ala Pro Gly Gly Leu Ser Ser Arg Glu
                245                 250                 255

Val Leu Thr Leu Leu Asp Val Val Gly Gln Leu Arg Pro Val Gly Phe
                260                 265                 270

Asp Val Val Glu Val Ser Pro Ala Tyr Asp Pro Ser Gly Ile Thr Ser
                275                 280                 285

Leu Leu Ala Ala Glu Ile Gly Ala Glu Leu Leu Tyr Gln Tyr Ala Arg
            290                 295                 300

Ala Thr Thr Ser Pro Ala Ser Ala Pro Val Asp Ser Pro Leu Pro Pro
305                 310                 315                 320

Gly Ala Ala Ala Asp Asp Ala Glu Asn Ala Glu Asn Ala Val Asp Ala
                325                 330                 335

Val Asp Ala Glu Ser Ala Val Asp Phe Ala Gly Gln Arg Trp Gly
            340                 345                 350

<210> SEQ ID NO 25
<211> LENGTH: 527
<212> TYPE: PRT
<213> ORGANISM: Streptomyces   clavuligerus

<400> SEQUENCE: 25

Met Pro Gly Pro Asp Leu Val Tyr Gly Phe Arg Val Arg Ile Gly Thr
1               5                   10                  15

Glu Gly Arg Pro Gly Gly Pro Gly His Ser Glu Pro Gly Ser
            20                  25                  30

Ala Pro Arg Phe Ala Val Arg Gly Thr His Val Pro Val His Asp Gly
            35                  40                  45

Thr Ala Tyr Pro Leu Trp Ser Gly Thr Ala Val Thr Leu Gly Arg Pro
    50                  55                  60

Pro Val Leu Val Ala Asp Gly Gln Val Arg Leu Leu Ala Gly Glu
65                  70                  75                  80

Leu Tyr Asn Arg Ala Glu Leu Thr Gly Ala Leu Gly Gly Ser Ser Ala
                85                  90                  95

Ala Leu Gly Asp Ala Glu Leu Leu Leu Ala Ala Trp Arg Arg Trp Gly
            100                 105                 110
```

-continued

```
Pro Gly Ala Phe Arg Leu Leu Asn Gly Arg Phe Ala Ala Leu Leu Thr
        115                 120                 125

Asp Ala Ser Thr Gly Ala Thr Val Ala Ala Thr Asp His Ala Gly Ser
    130                 135                 140

Val Pro Leu Trp Leu Arg Ala Asp Val Thr Gly Leu Ser Ala Ala Thr
145                 150                 155                 160

Glu Ala Lys Thr Leu Ala His Glu Pro Gly Arg Pro Leu Gly Leu Ser
                165                 170                 175

Gly Thr His Thr Ala Pro Gly Ala Ala Gly Val Cys Arg Val Pro Ala
            180                 185                 190

Gly Thr Ala Leu Leu His Gly Val Gly Gly Ser Asp Ile Thr Ala
        195                 200                 205

Arg Ala Val Arg Thr Trp Thr Pro Pro Leu Ser Arg Ala Leu Pro Gly
    210                 215                 220

Glu Arg Glu Ala Val Asp Leu Val Gly Glu Arg Leu Ala Thr Ala Val
225                 230                 235                 240

Arg Thr Arg Leu Arg Gly Gly Glu Ala Ala Pro Thr Val Val Leu Ser
                245                 250                 255

Gly Gly Ile Asp Ser Gly Gly Val Ala Ala His Thr Ala Ala Leu Ala
            260                 265                 270

Pro Gly Thr Arg Ser Val Ser Met Gly Thr Glu Val Ser Asp Glu Phe
        275                 280                 285

Asp Ala Ala Arg Ser Val Ala Val His Leu Gly Thr Ala His Ser Glu
    290                 295                 300

Ile Arg Leu His Ser Ala Glu Leu Val Arg Glu Leu Pro Trp Ala Val
305                 310                 315                 320

Ala Ala Ala Glu Ile Thr Asp Pro Thr Val Leu Glu Tyr Leu Leu Pro
                325                 330                 335

Leu Val Ala Leu Tyr Arg Arg Leu Asp Thr Gly Pro Leu Arg Ile Leu
            340                 345                 350

Thr Gly Tyr Gly Ala Asp Ile Pro Leu Gly Gly Met His Arg Arg Thr
        355                 360                 365

Ala Ser Leu Trp Ser Leu Asp Asp Glu Ile Ala Gly Asp Met Ala Gly
    370                 375                 380

Phe Asp Gly Leu Asn Glu Met Ser Pro Val Leu Ala Gly Ile Ala Gly
385                 390                 395                 400

Lys Trp Thr Thr His Pro Tyr Trp Asp Arg Ala Val Leu Asp Ala Leu
                405                 410                 415

Val Ser Leu Glu Pro Gly Leu Lys Arg Arg Gly Thr Asp Lys Trp
            420                 425                 430

Val Leu Arg Gln Ala Leu Ser Gly Leu Leu Pro Ala Glu Thr Val Ala
        435                 440                 445

Arg Pro Lys Leu Gly Ile His Glu Gly Ser Gly Thr Thr Ser Ala Trp
    450                 455                 460

Thr Gly Leu Leu Leu Ala Glu Gly Ile Arg Arg Asp Glu Val Thr Ala
465                 470                 475                 480

Val Lys Gly Ala Met Ala Arg Arg Leu Tyr Asp Ala Val Ile Asp
                485                 490                 495

Thr Val Pro Pro Glu Asp Val Asp Phe Gly Glu Thr Val Arg Arg Ser
            500                 505                 510

Val Asp Ala Val Arg Arg Leu Arg Leu Gln Gly Arg Val Val Val
        515                 520                 525
```

<210> SEQ ID NO 26
<211> LENGTH: 555
<212> TYPE: PRT
<213> ORGANISM: Streptomyces clavuligerus

<400> SEQUENCE: 26

```
Met Ala Thr Thr Thr Ala Lys Ala Met Leu Glu Arg Leu His Gln Tyr
 1               5                  10                  15

Gly Val Asp His Val Phe Gly Val Val Gly Arg Glu Ala Ser Ala Ile
            20                  25                  30

Leu Phe Asp Glu Val Glu Gly Leu Asp Phe Val Leu Thr Arg His Glu
        35                  40                  45

Phe Thr Ala Gly Val Met Ala Asp Val Leu Ala Arg Ile Thr Asn Arg
    50                  55                  60

Pro Gln Ala Cys Phe Ala Thr Leu Gly Pro Gly Met Thr Asn Leu Ala
65                  70                  75                  80

Thr Gly Val Ala Thr Ser Ala Leu Asp Arg Ser Ser Val Ile Ala Leu
                85                  90                  95

Ala Ala Gln Ser Glu Ser Tyr Asp Cys Tyr Pro Asn Val Thr His Gln
            100                 105                 110

Cys Leu Asp Ser Thr Ala Val Met Gly Pro Leu Thr Lys Phe Ser Val
        115                 120                 125

Gln Leu Glu Arg Gly Glu Asp Ile Val Asn Leu Val Asp Ser Ala Val
    130                 135                 140

Leu Asn Ser Arg Ile Glu Pro Val Gly Pro Ser Phe Ile Ser Leu Pro
145                 150                 155                 160

Val Asp Leu Leu Gly Ala Glu Leu Asn Gly Thr Pro Thr Asp Ala Pro
                165                 170                 175

Leu Val Arg Ala Thr Ala Thr His Ala Leu Asp Ala Asp Trp Arg Ala
            180                 185                 190

Arg Leu Asp Glu Ala Ala Glu Leu Val Arg Glu Ala Glu Asn Pro Leu
        195                 200                 205

Leu Val Val Gly Ser Ala Val Ile Arg Ala Gly Ala Val Asp Ala Leu
    210                 215                 220

Arg Ala Leu Ala Glu Arg Leu Asn Ile Pro Val Val Thr Thr Tyr Thr
225                 230                 235                 240

Ala Lys Gly Val Leu Pro His Asp His Pro Leu Asn Tyr Gly Ala Ile
                245                 250                 255

Ser Gly Tyr Met Asp Gly Ile Leu Gly His Pro Ala Leu Asp Glu Ile
            260                 265                 270

Phe Gly Pro Ala Asp Leu Leu Leu Ala Ile Gly Tyr Asp Tyr Ala Glu
        275                 280                 285

Asp Leu Arg Pro Ser Met Trp Thr Arg Gly Arg Ala Lys Thr Thr Val
    290                 295                 300

Arg Val Ala Pro Glu Val Asn Pro Ile Pro Glu Leu Phe Arg Ala Asp
305                 310                 315                 320

Ile Asp Ile Val Thr Asn Val Ala Glu Phe Val Thr Ala Leu Asp Asp
                325                 330                 335

Ala Thr Ser Gly Leu Ala Pro Lys Thr Arg His Asp Leu Ser Ala Leu
            340                 345                 350

Arg Ala Arg Val Ala Glu Phe Leu Ala Asp Pro Thr Glu Tyr Glu Asp
        355                 360                 365

Gly Met Arg Val His Gln Val Ile Asp Cys Met Asn Ser Val Leu Asp
    370                 375                 380
```

```
-continued

Asn Gly Thr Phe Val Ser Asp Ile Gly Phe Phe Arg His Tyr Gly Val
385                 390                 395                 400

Leu Phe Ala Lys Ser Asp Gln Pro Tyr Gly Phe Leu Thr Ser Ala Gly
            405                 410                 415

Cys Ser Ser Phe Gly Tyr Gly Leu Pro Ala Ala Met Ala Ala Gln Ile
            420                 425                 430

Ala Arg Pro Gly Glu Pro Val Phe Leu Ile Ala Gly Asp Gly Gly Phe
            435                 440                 445

His Ser Asn Ser Ala Asp Ile Glu Thr Ala Val Arg Leu Gly Leu Pro
            450                 455                 460

Ile Val Met Val Val Asn Asn Asp Arg Asn Gly Leu Ile Glu Leu
465                 470                 475                 480

Tyr Gln Asn Leu Gly His Gln Arg Ser His Ala Pro Ala Val Gly Phe
            485                 490                 495

Gly Ser Val Asp Phe Val Gln Leu Ala Glu Ala Asn Gly Cys Glu Ala
            500                 505                 510

Val Arg Ala Thr Asp Arg Thr Ser Leu Leu Ala Leu Thr Lys Gly
            515                 520                 525

Ala Gly Leu Gly Arg Pro Phe Leu Ile Glu Val Pro Val Ala Tyr Asp
            530                 535                 540

Phe Gln Ser Gly Gly Phe Ala Ala Leu Ala Ile
545                 550                 555

<210> SEQ ID NO 27
<211> LENGTH: 59
<212> TYPE: DNA
<213> ORGANISM: Artificial Sequence
<220> FEATURE:
<223> OTHER INFORMATION: PCR Primer

<400> SEQUENCE: 27
ccatcccggc gcccgtccga tgcgaaggag atctccatga ttccggggat ccgtcgacc         59

<210> SEQ ID NO 28
<211> LENGTH: 57
<212> TYPE: DNA
<213> ORGANISM: Artificial Sequence
<220> FEATURE:
<223> OTHER INFORMATION: PCR Primer

<400> SEQUENCE: 28
cggggccggg catggtgaac tcgtcctcca cggtggtcat gtaggctgga gctgctt          57
```

PROCESS FOR IMPROVING THE MANUFACTURE OF CLAVAMS E.G. CLAVULANIC ACID

This application is a 371 National Phase entry of international application PCT/EP04/04001 filed Apr. 13, 2004, which claims priority to international application GB0308696.4 filed Apr. 15, 2003.

The present invention relates to new processes for improving the manufacture of clavams e.g. clavulanic acid. The present invention also provides novel DNA sequences and new microorganisms capable of producing increased amounts of clavulanic acid.

Microorganisms, in particular Streptomyces sp. produce a number of antibiotics including clavulanic acid and other clavams, cephalosporins, polyketides, cephamycins, tunicamycin, holomycin and penicillins. There is considerable interest in being able to manipulate the absolute and relative amounts of these antibiotics produced by the microorganism and accordingly there have been a large number of studies investigating the metabolic and genetic mechanisms of the biosynthetic pathways (Demain, A. L. (1990) "Biosynthesis and regulation of β-lactam antibiotics." in "50 years of Penicillin applications, history and trends").

*Streptomyces clavuligerus* produces two major groups of antibiotics; one being the cephamycins, cephalosporins and penicillins (Demain, A. L. (1990) supra) and the other comprising clavams. Clavams can be arbitrarily divided into two groups, 5S and 5R clavams, dependent on their ring stereochemistry. The commercially important clavam clavulanic acid, a component of the antibiotic Augmentin (trade mark of GlaxoSmithKline), is a 5R clavam. Examples of 5S clavams are clavam-2-carboxylate (C-2-C), 2-hydroxymethyl clavam (2HMC) and alanylclavam (Brown et al. (1979) J. Chem. Soc. Chem. pp282-283).

Genes encoding biosynthetic enzymes and regulatory proteins for clavulanic acid production have been located in a cluster next to the genes involved in cephamycin C production and make up a supercluster of antibiotic related genes within the *S. clavuligerus* genome (Alexander et al. (1998) J. Bacteriol. 180:4068-79). For example the genes encoding the enzymes involved in clavaminic acid production, a clavulanic acid precursor, which include orf2 (ceaS) (Khaleeli et al. (1999) J. Am. Chem. Soc. 121:9223-9224), orf3 (bls) (Bachmann and Townsend (1998) Chem. Commun.:2325-2326), orf4 (pah) (Wu et al. (1995) J. Bacteriol. 177:3714-3720), orf5 (cas2) (Marsh et al. (1992) Biochemistry. 31:12648-57) and perhaps orf6 (Kershaw et al. (2002) Eur. J. Biochem. 269,2052-2059) are all located within the clavulanic acid cluster. Disruptions in orfs2-6 cause a complete loss of clavulanic acid production when mutant cultures are grown on starch asparagine medium (Aidoo, K. A. et al. (1993) p219-236 In. V. P. Gullo, J. C. Hunter-Cevera, R. Cooper and R. K. Johnson (ed.), Developments in Industrial Microbiology series, vol.33 Society for Industrial Microbiology, Fredericksburg, Va.). However this loss is conditional upon the growth media used for when mutants are grown on Soy medium (Salowe et al. (1990) Biochemistry 29: 6499-6508) clavulanic acid production is partially restored (Jensen et al. (2002) Antimicrob. Agents and Chemother. 44: 720-726). This phenomenon could suggest that other genes present in the *S. clavuligerus* genome could compensate in some way for the loss of the activity of these genes under certain conditions. Alternatively it could be that the Soy media contains very small amounts one or more of the metabolites produced by the orfs 2-6 allowing strains disrupted in these genes to make small amounts of clavulanic acid.

Marsh et al. (1992) supra has reported that *S. clavuligerus* contains two copies of the cas gene (cas1 and cas2). cas1 is not associated with the clavulanic acid gene cluster and has a high homology to cas2. Disruption of cas2 decreases clavulanic acid production by 35% when cultures are grown on Soy medium and eliminates production entirely when cultures are grown on starch asparagine (SA) medium (Paradkar and Jensen 1995 J. Bact 177: 1307-1314). The disruption of the cas1 gene results in mutants which produce near wild type levels of clavulanic acid on SA medium, but produce 31-73% less clavulanic acid when grown on Soy medium than the wild type (Mosher et al. (1999) Antimicrob. Agents and Chemother. 43: 1215-1224). It is also reported that in mutant strains where both the cas1 and cas2 genes have been disrupted no clavulanic acid is produced under any of the fermentation conditions tested. Interestingly when the genes surrounding cas1 were sequenced, no additional genes involved in clavulanic acid production were found but instead six novel genes involved in 5S clavam biosynthesis (named cvm1 to 6) were identified. (Mosher et al. (1999) supra). Further work on these 5S clavam-specific genes showed that disruption of the genes, using genetic engineering methodologies, leads to improvements in the levels of clavulanic acid made by the mutant strains and also dramatic reductions in the levels of 5S clavam production (WO98/33896). This reduction in 5S clavam production, in particular the 5S clavam clavam-2-carboxylate, is especially important in the commerical production of clavulanic acid because some 5S clavams are known to be toxic and for this reason the levels are tightly controlled within the British and U.S. Pharmacopoeias.

Despite these advances in the understanding of clavulanic acid biosynthesis it is still a highly desirable goal in the pharmceutical industry to continue to improve production methods for clavulanic acid, both for reasons of cost and for reasons of safety.

The following definitions are provided to facilitate understanding of certain terms used frequently herein:

"Gene" as used herein also includes any regulatory region required for gene function or expression.

"cvm" genes as used herein refers to any of the genes cvm1, cvm2, cvm 3, cvm4, cvm5, cvm6 or cvm7 as defined hereinabove.

"cvmpara" genes as used herein refers to any of the genes cvm6para or cvm7para as defined hereinabove.

"orf" genes as used herein refers to any of the genes orf2, orf3, orf4, orf5, orf6, orf7, orf8, orf9, orf10, orf11, orf12, orf13, orf14, orf15, orf16, orf17, or orf18 as defined hereinabove.

"orfpara" genes as used herein refers to any of the genes orf2para, orf3para, orf4para or orf6para as defined hereinabove.

"Disrupted" as used herein means that that the activity of the gene (with regard 5S clavam production) has been reduced or eliminated by, for example, insertional inactivation using an antibiotic resistance gene, preferably apromycin (Paradkar, A. S. and Jensen, S. E. (1995) supra), or other mutagenesis technique (for example those disclosed in Sambrook et al. (1989) supra). Other mutagenesis techniques include insertion of other DNAs (not antibiotic resistance genes), site-directed mutagenesis to either change one or more bases in the gene sequence or insert one or more bases into the sequence of the gene.

"Deleted" as used herein means that the gene, or a segment thereof, has been deleted (removed) from a larger polynucleotide which, before the deletion was performed, included said gene or segment thereof. When the polynucleotide bearing the deletion is introduced into the genome of the microorganism by means of gene replacement technology (Paradkar and Jensen (1995) supra) the activity of the gene or protein encoded thereby is eliminated or reduced such that the levels of 5S clavam produced by the microorganism are reduced. The deletion may be large (for example the complete open reading frame with or without regulatory control regions) or small (for example a single base pair resulting in a frameshift mutation).

"Reduced" as used herein means that the levels of 5S clavam produced by the microorganism of the invention are lower than the levels produced in the corresponding *S. clavuligerus* strain which has not had the relevant open reading frames disrupted or deleted. The corresponding *S. clavuligerus* is therefore the "parent" strain into which the disrupted or deleted open reading frames were subsequently introduced to generate the microorganism of the invention.

"At least maintained" as used herein means that the level of clavulanic acid produced in the microorganism of the invention is the same or greater than that produced in the corresponding *S. clavuligerus* strain which has not had the relevant open reading frames disrupted or deleted. The corresponding *S. clavuligerus* is therefore the "parent" strain into which the disrupted or deleted open reading frames were subsequently introduced to generate the microorganism of the invention.

The present invention concerns new processes for making clavulanic acid using newly identified *S. clavuligerus* genes. Using a probe derived from orf4 a fragment of the *S. clavuligerus* genome has been isolated and has been shown to comprise a number of genes that when disrupted are shown to affect 5S and 5R clavam biosynthesis in *S. clavuligerus*. Sequence analysis of the fragment has indicated the presence of a gene showing high similarity to orf4 (hereinafter called orf4par). However surprisingly further sequence analysis of the regions flanking the orf4par gene has revealed a new cluster of genes comprising paralogues of genes previously identified in both the clavulanic acid (cas2 cluster) and 5S clavam (cas1 cluster) gene clusters.

Accordingly the invention provides a *S. clavuligerus* microorganism comprising DNA corresponding to one or more open reading frames essential for 5S clavam biosynthesis, wherein said open reading frames are disrupted or deleted such that the production of 5S clavams by said *S. clavuligerus* is reduced and clavulanic acid production is at least maintained, wherein the open reading frames are selected from:
a) cvm6para (SEQ ID NO: 1);
b) cvm7para (SEQ ID NO:2);
c) cvm6para and cvm6 (SEQ ID NO:5); or
d) cvm7para and cvm7 (SEQ ID NO:6).

In a second aspect the invention provides a *S. clavuligerus* microorganism comprising DNA corresponding to one or more open reading frames essential for 5S clavam biosynthesis, wherein said open reading frames are disrupted or deleted such that the production of 5S clavams by said *S. clavuligerus* is reduced and clavulanic acid production is at least maintained, wherein the open reading frames are selected from:
a) cvm6para and one or more of cvm1 (SEQ ID NO:7), cvm2 (SEQ ID NO:8), cvm3 (SEQ ID NO:9), cvm4 (SEQ ID NO: 10), cvm5 (SEQ ID NO: 11), cvm6, cvm7 or cvm7para; or
b) cvm7para and one or more of cvm1, cvm2, cvm3, cvm4, cvm5, cvm6, cvm7 or cvm6para.

The genes cvm1, cvm2, cvm3, cvm4, cvm5 and cvm6 are disclosed in Mosher et al. (1999) supra and WO98/33896 (cvm1 is orfup1, cvm2 is orfup2, cvm3 is orfup3, cvm4 is ordwn1, cvm5 is orfdwn2 and cvm6 is orfdwn3. The cvm7 gene, found to be a further 5S clavam specific gene of the 5S clavam (cas1) cluster, has been identified during work leading to the present invention and is disclosed hereinbelow.

In a further aspect the invention provides isolated polynucleotides comprising the cvm6para and cvm7para open reading frames which are used in the preparation of the *S. clavuligerus* microorganism of the invention. Preferably said polynucleotides comprise open reading frames selected from the group consisting of:
a) cvm6para;
b) cvm7para;
c) cvm6para and cvm6;
d) cvm7para and cvm7;
e) cvm6para and one or more of cvm1, cvm2, cvm3, cvm4, cvm5, cvm6, cvm7 or cvm7para; or
f) cvm7para and one or more of cvm1, cvm2, cvm3, cvm4, cvm5, cvm6, cvm7 or cvm6para.

In another aspect the present invention provides vectors for cloning and manipulating the cvm polynucleotides disclosed herein and which can be used in the preparation of the *S. clavuligerus* microorganism of the invention. Processes for using these vectors to make the *S. clavuligerus* microorganism of the invention are also provided.

The encoded polypeptides from cvm6para and cvm7para are also provided by the invention (SEQ ID NO:3 and SEQ ID NO:4 respectively).

The invention further provides a polynucleotide comprising one or more open reading frames encoding one or more enzymes involved in clavulanic acid biosynthesis wherein said open reading frames are selected from the group consisting of:
a) orf2para (SEQ ID NO: 12),
b) orf3para (SEQ ID NO: 13),
c) orf4para (SEQ ID NO: 14), and
d) orf6para (SEQ ID NO:15).

In a further aspect the invention provides a polynucleotide comprising one or more open reading frames encoding one or more enzymes involved in clavulanic acid biosynthesis wherein said open reading frames comprise one or more of:
a) orf2para,
b) orf3para,
c) orf4para,
d) orf6para in combination with one or more genes involved in clavulanic acid biosynthesis selected from orf2, orf3, orf4, orf5, orf6, orf7, orf8, orf9, orf10 (Canadian patent application CA2108113 and Jensen, S. E. et al. (2000) Antimicrob. Agents Chemother 44:720-6) orf11, orf12 (Li, R. N. et al (2000) J. Bacteriol 182:4087-95), orf13, orf14, orf15, orf16, orf17, or orf18 (patent application PCT/GB02/04989).

Vectors comprising such polynucleotides are also provided by the present invention together with processes for the use of such vectors to prepare strains of *Streptomyces clavuligerus* which can be used to produce elevated levels of clavulanic acid.

Strains of *Streptomyces clavuligerus* so produced and methods for using them to produce clavulanic acid by fermentation are also provided.

Thus the invention further provides a *Streptomyces clavuligerus* microorganism comprising a vector comprising a polynucleotide comprising one or more open reading frames encoding one or more enzymes involved in clavulanic acid biosynthesis wherein said open reading frames are selected from the group consisting of:
a) orf2para,
b) orf3para,
c) orf4para, and
d) orf6para.

In a further aspect the invention provides a *Streptomyces clavuligerus* microorganism comprising a vector comprising a polynucleotide comprising one or more open reading frames encoding one or more enzymes involved in clavulanic acid biosynthesis wherein said open reading frames are selected from the group consisting of:
a) orf2para,
b) orf3para,
c) orf4para,
d) orf6para in combination with one or more genes involved in clavulanic acid biosynthesis selected from orf2, orf3, orf4, orf5, orf6, orf7, orf8, orf9, orf10 (Canadian patent application CA2108113 and Jensen, S. E. et al. (2000) Antimicrob. Agents Chemother 44:7206) orf11, orf12 (Li, R. N. et al (2000) J. Bacteriol 182:4087-95), orf13, orf14, orf15, orf16, orf17, or orf18 (patent application PCT/GB02/04989).

The present invention also contemplates a *S. clavuligerus* micoroganism comprising a combination of one or more disrupted or deleted cvm6para or cvm7para genes, optionally in combination with other disrupted or deleted 5S genes previously disclosed, together with vectors comprising orf2para, orf3para, orf4para or orf6para genes, optionally in combination with other clavulanic acid biosynthetic genes (selected from the genes orf2 to orf18) previously disclosed.

Polynucleotides of the invention can be isolated by conventional cloning methods, such as PCR or library screening methods, using the sequences disclosed herein and in Mosher et al (1999) supra, WO98/33896, Canadian patent application CA2108113, Jensen, S. E. et al. (2000) supra), Li, R. N. et al. (2000) supra and patent application PCT/GB02/04989, as indicated hereinabove. Examples of such cloning methods are described in, for example, Sambrook, J. et al (1989) Molecular cloning, a laboratory manual (2nd Ed) Cold Spring Harbor Laboratory, Cold Spring Harbor, N.Y.

Polynucleotides comprising individual open reading frames can be isolated and ligated together into vectors in a variety of combinations as defined hereinabove using techniques well know in the art. The choice of vector will depend on the function being carried out, for example cloning, expression, gene inactivation or transfer into *S. clavuligerus* eg. for gene replacement. In all cases a variety of vectors are available to the skilled person and are well known in the art. For example such vectors are known from Sambrook, J. et al. (1989) supra for general cloning vectors Hopwood, D. A. et al. (1985) supra for Streptomyces vectors, Paradkar and Jensen (1995) supra, Mosher et al. (1999) supra and WO98/33896 supra for gene disruption and gene replacement vectors and CA2108113 supra for vectors suitable for expression of genes in *Streptomyces clavuligerus*. However the choice of vector is not limited to just those disclosed in these sources.

Further, in the case of the gene combinations involving the orf2para, orf3para, orf4para, orf5para and orf6para genes the skilled artisan would be able to design suitable DNA constructs to ensure that each open reading frame is suitably positioned relative to a transcriptional promoter, whether this be the native promoter or a heterologous promoter that also functions in the *Streptomyces clavuligerus* background, or indeed other regulatiry sequence, in such a manner that expression of each open reading frame is optimally achieved.

Subsequent manipulation of the polynucleotides, in particular with respect their introduction into the *Streptomyces clavuligerus* background, can be carried out according to standard methods as disclosed in, for example, Hopwood, D. A. et al. (1985) supra. Disruption of gene sequences, and subsequent gene replacement, can be carried out according to the method of Paradkar, A. S. and Jensen, S. E. (1995) supra. Deletion of gene sequences can be carried out using well established techniques, for example that disclosed in WO98/33896.

Microorganisms of the invention can be prepared from *Streptomyces clavuligerus* strains including, but not limited to, *Streptomyces clavuligerus* ATCC 27064 (American Type Culture Collection, Manassas, Va., USA), alternatively available as NRRL 3585 (Northern Regional Research Laboratory, Peoria, Ill., USA). For example mutant strains of *Streptomyces clavuligerus* can also be used including those prepared by genetic engineering techniques, or those prepared by strain improvement methods. Examples of such strains include *Streptomyces clavuligerus* strains 56-1A, 56-3A, 57-2B, 57-1C, 60-1A, 60-2A, 60-3A, 61-1A, 61-2A, 61-3A or 61-4A as disclosed in WO98/33896.

Thus in another aspect the invention relates to a process for improving clavulanic acid production in a suitable microorganism comprising isolating a polynucleotide as described hereinabove, manipulating said polynucleotide, introducing the manipulated polynucleotide into a said suitable microorganism, fermenting said suitable microorganism under conditions whereby clavulanic acid is produced, isolating and purifying clavulanic acid so produced. Manipulation of said polynucleotide may be by means of disrupting or deleting gene sequences in the case of cvmpara genes, optionally together with cvm genes, or by inserting into vectors suitable for expression in the case of orfpara genes, optionally together with orf genes.

Preferably the suitable microorganism is *Streptomyces clavuligerus*.

Such fermentation, isolation and purification methods are well known in the art, for example the fermentation methods disclosed in UK Patent Specification No. 1,508,977. Methods for using clavulanic acid in the preparation of antibiotic formulations are similarly well known in the art.

EXAMPLES

Example 1

Materials and Methods

In the examples all methods are as described in Sambrook, J. et al. supra, Hopwood, D. A. et al. (1985) supra and Kieser, T. et al. (2000) Practical *Streptomyces* Genetics, unless otherwise stated. Transformation methods can also be found in Paradkar, A. S. and Jensen, S. E. (1995) supra.

1.1 Bacterial strains, media and culture conditions.

*Streptomyces clavuligerus* NRRL 3585 was obtained from the Northern Regional Research Laboratory (Peoria, Ill.). *S. clavuligerus* was maintained on either MYM agar (Stuttard, C. (1982) J. Gen. Microbiol. 128:115-121) or ISP Medium #4 agar plates (Difco, Detroit, Mich.).

Cultures for the isolation of chromosomal DNA were grown on a 2:3 mixture of trypticase soy broth and YEME as described by Alexander et al.(1998) J. Bact. 180:4068-79. Cultures for analysis of the production of clavulanic acid and other clavam metabolites were grown on Soy medium (European Patent 0349 121) unless otherwise stated. All liquid cultures were grown at 26° C. on a rotary shaker at 250 rpm.

Manipulation of DNA in *Escherichia coli* was done using strain XL-1 Blue (Stratagene, La Jolla, Calif.). *E. coli* cultures were maintained on LB agar medium and grown in liquid culture in LB medium at 37° C. (Sambrook, J. et al. (1989) supra). Plasmid-containing cultures were supplemented with appropriate levels of antibiotic.

1.2 DNA manipulations.

Standard DNA manipulations such as plasmid isolation, restriction endonuclease digestion, generation of blunt-ended fragments, ligation, $^{32}$P labelling of DNA probes by nick translation and *E. coli* transformation were carried out as described in Sambrook J. et al. (1989) supra. Plasmid and genomic DNA isolation from *Streptomyces* spp. was conducted as described in Kieser, T. et al. (2000) supra. Construction of a library of *S. clavuligerus* genomic DNA fragments in the cosmid pWE15 was carried out according to the manufacturer's instructions (Stratagene).

Southern analysis of *S. clavuligerus* DNA fragments was conducted at high stringency as described by Sambrook, J. et al. (1989) supra. Hybridization membranes were washed twice for 30 min at 2×SSC/0.1% SDS and once for 30 min at 0.1×SSC/0.1% SDS, all at 65° C.

Example 2

Preparation of the paralogue cluster DNA fragment 2.1 Cloning and nucleotide sequencing of the orf4 paralogue A strong and a very weak hybridization signal was consistently observed on Southern blots of NcoI-digested *S. clavuligerus* chromosomal DNA when probed with the orf4 gene (CA2108113). The strong signal corresponded to the orf4 gene, but the identity of the gene that gave rise to the very weak signal was unknown. Therefore it was decided to clone this gene. To this end, NcoI fragments from *S. clavuligerus* DNA of approximately 4-5kb in size were ligated into NcoI digested pUC120 (Vieira, J. and J. Messing (1987) Methods Enzymol. 153, 3-11) and screened using a colony blot hybridisation method and employing the orf4 gene as a probe. Plasmid DNA was isolated from potential positive clones and confirmed to carry a 4.3 kb NcoI fragment. A representative clone, pO4H-4, was chosen for further study. The sequencing of the 4.3 kb NcoI fragment was carried out. Analysis of the sequence generated identified three genes, one which had homology to orf4 and was called orf4par. The two other genes present were found to have homology with orf6 and cvm6 and were therefore called orf6par and cvm6par. This result suggested that this region of DNA may contain a cluster of genes with paralogues in either the clavulanic acid biosynthetic gene cluster or the cvm clavam biosynthetic gene cluster.

2.2 Sequencing of DNA flanking the 4.3 kb NcoI fragment containing orf4par

Sequence analysis of DNA flanking the 4.3 kb NcoI fragment containing orf4par was achieved by identifying 2 cosmid clones containing the orf4par gene. The two cosmid clones containing orf4par, 14E10 and 6G9, were isolated from a *S. clavuligerus* pWE15 (Promega, Madison, Wis.) cosmid bank that had been probed with a 0.46Kb SalI fragment that is internal to the orf4par gene. These cosmids have been partially mapped using a series of digestions and Southern hybridization experiments (In. Nucleic acid techniques in bacterial systematics. Ed. Stackebrandt, E. and Goodfellow, M. (1991) John Wiley and Sons, p205-248). Digestion of both cosmids with EcoRI, KpnI and NruI suggest that the insert size of 14E10 is approximately 45 kb and 6G9 is approximately 40 kb. These two cosmid inserts have about 20 kb of overlapping DNA and provided DNA for sequence analysis of regions upstream and downstream of the 4.3 kb NcoI fragment containing orf4par.

DNA sequence information was generated essentially as described in CA2108113. The DYEnamic ET Terminator Cycle Sequencing Kit (Amersham Pharmacia, Baie d'Urfe, Quebec, Canada) was used. Approximately 13.3 kilobases of contiguous DNA sequence was generated. The nucleotide sequence of the *S. clavuligerus* chromosomal DNA generated in these experiments is shown in SEQ ID No: 16.

A number of open reading frames were identified which displayed significant homology with the previously described orf2, orf3, orf4, and orf6 (CA2108 113). These genes have been located within the genome in relation to each other, and are found to be nearly in the same organisation as that of the genes within the clavulanic acid cluster. The genes orf2par, orf3par and orf4par are adjacent to each other and in the same orientation as their counterparts orf2, orf3 and orf4. However cas1 is not downstream of orf4par as cas2 is to orf4 in the clavulanic acid pathway but is instead within the clavam cluster (Mosher et al (1999) supra). Another difference between the clavulanic acid cluster and the paralogue arrangement is that orf6par is end-on-end to orf4par, and so is not in the same orientation as orf2par4par, whereas orf6 is in the same orientation as orfs2-4 in the clavulanic acid cluster. Suprisingly the gene immediately upstream of orf6par, was found to be a gene that had a paralogue in the clavam and not the clavulanic acid cluster. This gene was called cvm6par, as it is a paralogue of the cvm6 gene found clustered with cas1 (Mosher et al. (1999) supra). The cvm6 gene encodes an enzyme that is involved in clavam production (orfdwn3 in WO98/33896).

Located adjacent to cvm6par is a new gene called cvm7par. This gene shows homology to cvm7, a gene that is located upstream of cvm3 in the clavam cluster (further described hereinbelow). Upstream of cvm7 is a new open reading frame, believed to encode a sensor kinase. It encodes an polypeptide of 555 amino acids and shows good similarity to sensor kinase domains of two component response regulator genes.

2.3 Functional analysis of the open reading frames

Computer analysis of the DNA sequence shown in SEQ ID No.16 predicts the presence of 7 open reading frames. A description of each gene is shown in Table 1.

TABLE 1

| Orf Designation | Homology (blast P) |
| --- | --- |
| orf2par | acetolactate synthase (67% identity to orf2 carboxyethyl arginine synthase CEAS) |
| orf3par | asparagine synthetase (49% identity with orf3 β-lactam synthase BLS) |
| orf4par | amidinohydrolase (71% identity with orf4 amidinohydrolase PAH) |
| orf6par | ornithine acetyltransferase (47% identity with orf6 ornithine acetyl transferase OAT) |
| cvm6par | aminotransferase (66% identity with cvm6 acetylornithine aminotransferase) |
| cvm7par | Transcriptional regulator (33% identity with cvm7homologue) |
| Sensor Kinase | Sensor Kinase 47% identity with 2 component system from *S.coelicolor* A3 (2) |

To assess the possible roles of these ORFs in the biosynthesis of clavulanic acid and/or clavams produced by *S. clavuligerus*, insertional inactivation mutants were created by gene replacement essentially as described by Paradkar and Jensen (1995) supra. However, in order to definitively define the phenotype of these disruptions, it was considered important to disrupt orf3par, orf4par, orf6par and cvm6par not only in wild type *S. clavuligerus*, but also in strains of *S. clavuligerus* that were already defective in the expression of orf3, orf4, orf6, and cvm6 respectively. The orf3,4 and 6 mutants were made as described in U.S. Pat. No. 6,332,106 and the cvm6 mutant made as described in WO98/33896.

Example 3

Analysis orf4, and orf4par 3.1 Construction of orf4 mutants

Mutants disrupted in orf4 (pah) were made as described in U.S. Pat. No. 6,332,106.

3.2 Construction of orf4 par mutants pO4H-4 (4.3kb NcoI fragment cloned into the NcoI site of pUC120 (Vieira and Messing 1987 supra) was digested with KpnI (one site in the cloned fragment and one site in the vector) and religated to reduce the size of the orf4par-bearing DNA insert to 1.7 kb thereby generating the plasmid p4K-1. The orf4par gene within p4K-1 was disrupted by digestion at its centrally located EcoNI site and insertion of the apramycin (apr) resistance gene cassette from pUC120apr (Trepanier et al. (2002) Microbiology 148: 643-656) after both fragments had been made blunt by treatment with the Klenow fragment of DNA polymerase I. The KpnI/NcoI insert carrying the disrupted orf4par gene was then inserted into the EcoRI site of pDA501 after blunting the ends of both insert and vector. pDA501 is a shuttle vector prepared by fusing the Streptomyces plasmid pIJ486 (Kieser, T. et al. (2000) supra) to the *E. coli* plasmid pTZ18R (Stratagene) by means of their EcoRI and BamHI sites. The resulting construct, 6pDAB, was used to transform *S. lividans* TK24, and finally wild-type *S. clavuligerus* to thiostrepton (thio at 5 µg/ml) and apramycin (apr at 20 µg/ml) resistance.

Gene replacement mutants were generated as described by Paradkar and Jensen (1995) supra.

3.3 Construction of orf4/orf4par mutants

An approach was undertaken to generate the double mutant by transforming protoplasts of the orf4par (apr$^r$) mutant with the orf4 (thio$^r$) disruption construct (Aidoo et al. (1994) Gene. 147:41-6). Protoplast preparations from orf4par mutants, were transformed with the orf4 disruption construct isolated from *S. lividans*. Transformants were selected on thiostrepton at 5 µg/ml and hygromycin (hyg) at 50 µg/ml. Primary transformants were put through two rounds of sporulation under non-selective conditions in order to generate gene replacement mutants as described by Paradkar and Jensen (1995) supra.

3.4 Fermentation analysis of orf4, orf4par and orf4/orf4 par mutants

To test the effect of disrupting orf4, orf4par and orf4/4par on clavulanic acid biosynthesis, spores from each isolate were inoculated into 20 ml of seed medium (European patent 0 349 121) and grown for 2 days at 26° C. with shaking. 1 ml of the seed culture was then inoculated into a final stage Soy medium (European Patent 0349 121) and grown at 26° C. for up to 3 days with shaking. Samples of final stage broth were withdrawn after three days growth and assayed for clavulanic acid productivity by HPLC (Mosher et al. (1999) supra) and/ or using an imidazole derivatised calorimetric assay (Bird, A. E. et al. (1982) Analyst, 107:1241-1245 and Foulston, M. and Reading, C. (1982) Antimicrob. Agents Chemother., 22:753-762).

Fermentation analysis of orf4 disruptant

The orf4 disruptant was fermented in Soy medium and compared to wild type *S. clavuligerus* for production of clavulanic acid. After 72 hrs growth, accumulation of clavulanic acid was reduced by 71%.

From these results it can be concluded that orf4 is required for efficient production of clavulanic acid as elimination of this gene by disruption causes a reduction in clavulanic acid levels.

Fermentation analysis of orf4par disruptant

Mutant 5pDA defective in the orf4par gene was fermented in Soy medium and compared to wild type *S. clavuligerus* for production of clavulanic acid. After 72 hrs growth, accumulation of clavulanic acid was reduced by 12%.

From these results it can be concluded that, like orf4, orf4par contributes to clavulanic acid biosynthesis as elimination of this gene by disruption causes a reduction in clavulanic acid levels.

Fermentation analysis of orf4/orf4par disruptants

When mutants A4-A1 and 3A3-A3, defective in both copies of the orf4 genes were grown in Soy medium production of clavulanic acid could not be detected.

From these results it can be concluded that under the conditions tested, both genes, orf4 and orf4par, contribute to clavulanic acid biosynthesis as the double disruption, results in a mutant unable to make clavulanic acid.

3.5 Southern Analysis

The orf4 orf4par and orf4/4par mutants were further characterised by Southern analysis. The results confirmed that in these mutants the chromosomal copies of the relevant genes had been disrupted as expected.

Example 4

Analysis of orf6 and orf6par 4.1 Construction of orf6 mutants orf6 mutants were made as described in U.S. Pat. No. 6,332,106.

4.2 Construction of orf6 par mutants

The orf6par gene was disrupted by introduction of a neomycin resistance gene (neo$^r$) into the RsrII site, approximately midway through the coding region. In order to achieve this pO4H-4 was digested with KpnI to remove orf4par and self ligated to give p5K-6. p5K-6 was digested with RsrII and the neomycin resistance gene, released from pFDNeo-S (Denis and Brzezinski (1992) Gene 111:115-118.) as a PstI/EcoRI fragment, was inserted after both fragments had been made blunt by treatment with the Klenow fragment of DNA polymerase I. The construct pNeo5K-6A was obtained which has the neo$^R$ gene in the same orientation as the orf6par gene.

A shuttle vector called pNeo5K-6Atsr#14 was constructed by inserting pIJ486 as a 6.2 Kb fragment linearised with BglII, into the BamHI polylinker site of pNeo5K-6A. The shuttle vector was used to transform *S. lividans* TK24 and finally *S. clavuligerus* WT to thiostrepton (5 µg/ml) and neomycin (50 µg/ml) resistance. Primary transformants were subjected to two rounds of sporulation under non-selective conditions in order to generate gene replacement mutants as described by Paradkar and Jensen (1995) supra.

4.3 Construction of orf6/orf6par mutants orf6/orf6par double mutants were generated by transforming protoplasts of the orf6par (neo$^r$) mutant with the orf6 (apr$^r$) disruption construct (Mosher et al. (1999) supra). Protoplast preparations from orf6par mutants, were transformed with the orf6 disruption construct isolated from *S. lividans*. Transformants were selected on apramycin (apr) at 50 µg/ml.

Primary transformants were put through two rounds of sporulation under non-selective conditions in order to generate gene replacement mutants as described by Paradkar and Jensen (1995) supra.

4.4 Fermentation of orf6, orf6 par and orf6/orf6par mutants

To test the effect of disrupting orf6, orf6par and orf6/orf6par on clavulanic acid biosynthesis, spores from each isolate were tested as previously described in section 3.4.

Fermentation Analysis of orf6 mutants

Mutant 6-1A defective in the orf6 gene was fermented in Soy medium and compared to wild type *S. clavuligerus* for production of clavulanic acid. After 72 hrs growth, accumulation of clavulanic acid was reduced by 57%. From these results it can be concluded that orf6 is required for efficient production of clavulanic acid as elimination of this gene by disruption causes a reduction in clavulanic acid levels.

Fermentation Analysis of orf6par mutants

Mutant 14-2B(2) defective in the orf6par gene was fermented in Soy medium and compared to wild type *S. clavuligerus* for production of clavulanic acid. After 72 hrs growth, accumulation of clavulanic acid was reduced by 27%. From these results it can be concluded that, like orf6, orf6par contributes to clavulanic acid biosynthesis as elimination of this gene by disruption causes a reduction in clavulanic acid levels.

Fermentation Analysis of orf6/orf6par mutants

Two separate mutants defective in both orf6 and orf6par were fermented in Soy medium and compared to wild type *S. clavuligerus* for production of clavulanic acid. After 72 hrs growth, accumulation of clavulanic acid was reduced by an average of 65%.

From these results it can be concluded that both orf6 and orf6par are necessary for efficient production of clavulanic acid since disruption of either copy of the gene causes a reduction in clavulanic acid production. Inactivation of both copies of the gene caused a further decrease, but not a complete loss of clavulanic acid producing ability.

4.5 Southern Analysis

The orf6, orf6par and orf6/or6par mutants were further characterised by Southern analysis. The results confirmed that in these mutants the chromosomal copy of the relevant gene had been disrupted as expected.

Example 5

Analysis of cvm6 and cvm6par 5.1 Construction of cvm6 mutants

Construction of mutants disrupted in cvm6 has already been described in WO98/33896 (cvm6 is orfdwn3).

5.2 Construction of cvm6par mutants

A 1.7 Kb SalI fragment containing cvm6par was released from pO4H-4 and ligated into pUC118 at the SalI site. The resulting plasmid was digested with EcoNI to release a 140 bp fragment internal to cvm6par. In place of this fragment, the neomycin resistance gene from pFDNeo-S, released as an EcoRI/PstI fragment, was ligated into cvm6par after both fragments had been made blunt by treatment with the Klenow fragment of DNA polymerase I. The neo$^R$ marker was inserted in the same orientation as cvm6par. The neomycin containing SalI fragment was released with EcoRI and inserted into the shuttle vector pUWL-KS (Weimeier, U. F. (1995) Gene 165:149-150.) at the EcoRI site. The construct was named pNeoSal1.7U.

The plasmid pNeoSal1.7U was used to transform *S. lividans* TK24, and finally *S. clavuligerus* wild type. The resulting cvm6par::neo transformants were selected on MYM medium with 50 µg/ml neomycin and 5 µg/ml thiostrepton and then subjected to two rounds of sporulation under non-selective conditions to give double cross-over mutants.

5.3 Construction of cvm6/cvm6par mutants

The construct pNeoSal1.7U isolated from *S. lividans* TK24 was also used to transform the cvm6 mutant 56-3A, where the apr$^R$ cassette was inserted into cvm6 in the same orientation as the gene. Transformants were grown on MYM medium with 50 µg/ml neomycin and 5 µg/ml thiostrepton. The mutants were put through two rounds of sporulation under non-selective conditions as described above and double cross-over mutants were isolated.

5.4 Fermentation of cvm6, cvm6par and cvm6/cvm6par mutants

To test the effect of disrupting cvm6, cvm6par and cvm6/cvm6par on β-lactam biosynthesis, spores from each isolate were tested as previously described in section 3.4.

Fermentation Analysis of cvm6 mutants

It was reported in WO98/33896 that mutants 56-1A, 56-3A, 57-1C and 57-2B defective in the cvm6 gene produced elevated levels of clavulanic acid (125-141% of the control strain) and greatly reduced levels of clavam-2-carboxylate and 2-hydroxymethylclavam when cultured in Soy medium.

These results suggest that the cvm6 gene is required for efficient production of the 5S clavans. Disruption of cvm6 not only results in a reduction in clavams but also a simultaneous increase in clavulanic acid.

Fermentation Analysis of cym6par mutants Mutants 3A1, 3A2, 2A-6, 2B-1 and 2B-2 defective in the cvm6par gene were fermented in Soy medium and compared to wild type *S. clavuligerus* for production of β-lactam metabolites. After 72 hrs growth, accumulations in clavulanic acid were increased by 6-11%. Production of clavam-2-carboxylate and alanyl clavam was abolished and levels of 2-hydroxymethyl clavam reduced by 50-85%.

These results suggest that like cvm6 the cvm6par gene is required for efficient production of the 5S clavams. Disruption of cvm6par not only results in a reduction in clavams but also a simultaneous increase in clavulanic acid.

Fermentation Analysis of cvm6/cvm6par double mutants

Mutants A-1, A-2, B-1, B-2, C-1 and C-2 defective in both the cvm6 and cvm6par genes were grown in Soy medium and compared to wild type *S. clavuligerus* for their production of β-lactam metabolites. Production of clavulanic acid was increased by 12-27%, production of alanyl clavam and clavam-2-carboxylate eliminated and levels of 2-hydroxymethyl clavam reduced by 70-83%.

These results indicate that, like the cvm6 and cvm6par single mutants, the cvm6/cvm6par double mutants produced elevated levels of clavulanic acid and both genes are required for the efficient production of 5S clavams.

5.5 Southern Analysis

The cvm6, cvm6par and cvm6/cvm6par mutants were further characterised by Southern analysis. The results confirmed that in these mutants the chromosomal copies of the relevant genes had been disrupted as expected.

Example 6

Analysis of orf3 and orf3par 6.1 Construction of orf3 mutants

Mutants disrupted in orf3 were made as described in U.S. Pat. No. 6,332,106.

6.2 Construction of orf3par mutants

The plasmid p5.7EcoRI ref (pJOE based hyg) was used as the disruption template for orf3par. The insert in this plasmid is approximately 5.7kb and includes part of cvm6par, all of orf6par, orf4par, orf3par and part of orf2par all carried within the plasmid pJOE829 (Kieser, T. et al. (2000); Aidoo et al. (1994) Gene, 147:41-6). The disruption vector was constructed by ligation of a thiostrepton resistance cassette (Aidoo et al. supra) into FseI digested p5.7EcoRI. A unique FseI site is located within the insert 507 bp from the start of orf3par. The correct construct was obtained and used to sequentially transform *S. lividans* TK24 and then *S. clavuligerus* wild type. Primary transformants were selected on thiostrepton (5 µg/ml) and hygromycin (25 µg/ml). The mutants were put through two rounds of sporulation under non-selective conditions as described above and putative double cross-over mutants were isolated.

6.3 Construction of orf3/orf3par mutants

The orf3par disruption cassette described in section 6.2 was isolated from *S. lividans* TK24 and used to transform orf3::apra mutants. Transformants were selected on MYM medium containing thiostrepton (5 µg/ml) and hygromycin (25 µg/ml). The mutants were put through two rounds of sporulation without selection and double crossover mutants isolated as previously described.

6.4 Fermentation Analysis of orf3, orf3par and orf3/orf3par mutants

To test the effect of disrupting orf3, orf3par and orf3/orf3par on clavulanic acid biosynthesis, spores from each isolate were tested as previously described in section 3.4.

Fermentation Analysis of orf3 mutants

Mutants Ap3-1, Ap3-2 and Ap3-3 were fermented in Soy medium and compared to wild type *S. clavuligerus* for production of clavulanic acid. After 72 hrs growth, accumulations in clavulanic acid were reduced by 31-71%.

From these results it can be concluded that orf3 is required for efficient production of clavulanic acid as elimination of this gene by disruption causes a reduction in clavulanic acid levels.

Fermentation of orf3par mutants

Mutants 3A-1 and 3A-2 were fermented in Soy medium and compared to wild type *S. clavuligerus* for production of clavulanic acid. After 72 hrs growth, accumulations in clavulanic acid were reduced by 9%.

From these results it can be concluded that orf3par is required for efficient production of clavulanic acid as elimination of this gene by disruption causes a reduction in clavulanic acid levels.

Fermentation of orf3/orf3par mutants

Clavulanic acid biosynthesis was completely abolished when mutants 11-1, 11-2, 2-1 and 2-2 defective in both copies of the orf3 gene were grown in Soy medium and compared to wild type *S. clavuligerus*.

These results demonstrate that under the conditions tested, both genes, orf3 and orf3par, contribute to clavulanic acid biosynthesis as the double disruption results in a mutant unable to make any clavulanic acid.

6.5 Southern Analysis

The orf3, orf3par and orf3/orf3par mutants were further characterised by Southern analysis. The results confirmed that in these mutants the chromosomal copies of the relevant genes had been disrupted as expected.

Example 7

Analysis of orf2 and orf2par 7.1 Construction of orf2 mutants

Mutants disrupted in orf2 were originally made as described in U.S. Pat. No. 6,332,106. These original orf2 mutants were subjected to a second round of gene replacement to remove the apramycin resistance gene and replace it with a simple frameshift mutation. The plasmid construct used to create the original orf2 mutant consisted of a 2.1 kb EcoRI/BglII fragment of *S. clavuligerus* DNA carried on a pUC119/pIJ486 shuttle vector, with the orf2 gene disrupted by insertion of an apramycin resistance gene cassette into a centrally located NotI site (U.S. Pat. No. 6,332,106). The disruption plasmid construct used in the second round of mutation was derived from the original disruption plasmid by digestion with NotI to release the apramycin resistance gene cassette, treatment with the Klenow fragment of DNA polymerase I to fill in the overhanging ends, and then re-ligation to circularize the plasmid. The resulting plasmid construct carries the entire orf2 gene but with a frameshift introduced at the location of the destroyed NcoI site. The construct was used to sequentially transform *S. lividans* TK24 and then the original *S. clavuligerus* orf2 mutant. Primary transformants were selected on thiostrepton (5 µg/ml) and then subjected to two rounds of sporulation under non-selective conditions. Putative double cross-over mutants were identified based on their loss of apramycin resistance.

7.2 Construction of orf2par mutants orf2par mutants were generated using a PCR-based targeting kit known as REDIRECT (trade Mark of Plant Bioscience Limited, Norwich, U.K). The plasmids pIJ1790 and pIJ773, and the host strain *E. coli* BW25113 were supplied as part of the kit. For this particular application, a pair of oligonucleotide primers, KTA14: 5'-CCATCCCGGCGCCCGTC-CGATGCGAAGGAGATCTCCATGATTC-CGGGGATCCGTCGACC-3' (SEQ ID NO:27) and KTA15: 5'-CGGGGCCGGGCATGGTGAACTCGTCCTC-CACGGTGGTCATGTAGGCTGGAGCTGCTT-3' (SEQ ID NO: 28), designed to disrupt the orf2par gene by insertion of an paramecia resistance gene, were synthesized. The orf2par disruption cassette was generated by PCR using these two primers with the plasmid pIJ773 as template. PCR conditions used wereas described in the user instructions except that no dimethylsulfoxide was used. The orf2par disruption cassette was then introduced by electrotransformation into *E. coli* BW25113/pIJ790 which had been previously transformed with the orf2par bearing cosmid 14E10 (described hereinabove). Cosmid DNA was isolated from transformants after overnight growth at 37° C. to promote loss of the pIJ790 plasmid and analyzed to confirm that the orf2par gene had been disrupted. orf2par disrupted cosmid DNA was then transferred into wild type *S. clavuligerus* by conjugation. Conjugation was carried out as described by Kieser, T. et al. (2000) supra except that AS-1 medium (Baltz, R. H. Genetic recombination by protoplast fusion in *Streptomyces*. Dev. Ind. Microbiol 21 (1980) 43-54) supplemented with apramycin at 50 µg/ml was used for recovery of transconjugants. Apramycin resistant *S. clavuligerus* transconjugants were subjected to one round of sporulation under non-selective conditions in order to generate gene replacement mutants as described by Paradkar and Jensen (1995) supra.

7.3 Construction of orf2/orf2par mutants

The PCR-based targeting procedure used to generate the orf2par mutants (section 7.2) was also used to generate orf2/orf2par double mutants. In this case the orf2par disrupted cosmid DNA was conjugated into the orf2 mutants described above (section 7.1) rather than into the wild type strain. Apramycin resistant *S. clavuligerus* transconjugants were subjected to one round of sporulation under non-selective conditions in order to obtain unigenomic mutant spores that had undergone gene replacement as previously described.

7.4 Fermentation analysis of orf2, orf2par and orf2/orf2par mutants

To test the effect of disrupting orf2, orf2par and orf2/2par on clavulanic acid biosynthesis, spores from each isolate were tested as previously described in section 3.4.

Fermentation Analysis of orf2 mutants

Mutants defective in the orf2 gene were fermented in Soy medium and compared to wild type *S. clavuligerus* for production of clavulanic acid. After 72 hrs growth, accumulations in clavulanic acid were reduced by 95-98% (Jensen et al. (2000) supra.

From these results it can be concluded that orf2 is required for efficient production of clavulanic acid as elimination of this gene by disruption causes a severe reduction in clavulanic acid production.

Fermentation analysis of orf2par disruptant

Mutants defective in the orf2par gene were fermented in Soy medium and compared to wild type *S. clavuligerus* for production of clavulanic acid. After 72 hrs growth, accumulation of clavulanic acid was reduced by 10-30%.

From these results it can be concluded that, like orf2, orf2par contributes to clavulanic acid biosynthesis as elimination of this gene by disruption causes a reduction in clavulanic acid levels.

Fermentation analysis of orf2/orf2par disruptants

Mutants defective in both orf2 and orf2par were fermented in Soy medium and compared to wild type *S. clavuligerus* for production of clavulanic acid. After 72 hrs growth, no clavulanic acid production could be detected from the strains contain the orf2 and orf2par mutations. These results demonstrate that under the conditions tested, both genes, orf2 and orf2par, contribute to clavulanic acid biosynthesis as the double disruption results in a mutant unable to make clavulanic acid.

5. Southern Analysis

The orf2, orf2par and orf2/2par mutants were further characterised by Southern analysis. The results confirmed that in these mutants the chromosomal copies of the relevant genes had been disrupted as expected.

Example 8

Analysis of cvm7 and cvm7/par

Sequence analysis had identified two additional genes in the paralogue cluster that did not have obvious paralogues in either the clavulanic acid or cvm gene clusters. It was of interest to determine if either of these genes was a paralogue to an as yet unidentified cvm gene. Therefore the sequence of the cvm cluster (WO98/33896) was extended downstream of cvm3 (orfup3 in WO98/33896).

8.1 Extension of cvm cluster sequence

The cosmid 10D7 (described in WO98/33896) was digested with the restriction endonuclease SacI. From this digestion a 6.8 kilobase DNA fragment containing cas1 and cvm1 was isolated and cloned into a pUC119 based plasmid. The resultant plasmid pCEC019 was used as a template to generate sequence information which allowed completion of the partial cvm3 gene reported in WO98/33896. In addition, the sequence information showed the presence of another open reading frame, cvm7, which was incomplete in this fragment. In order to complete the cvm7 gene sequence, the next adjacent SacI fragment from cosmid 10D7, a 1.9 kb fragment, was subcloned. Sequence information was obtained from the end of the clone which contained the remainder of the cvm7 gene, up to the point where the start codon for the cvm7 gene could be identified. In total, this resulted in the generation of a further approximately 3.9 kb of new DNA sequence which is described in Sequence ID No.17.

8.2 Sequence analysis

The size of cvm7 and its orientation relative to the rest of the cvm cluster is showed diagrammatically in FIG. 2. Sequence homology searches demonstrated that this gene shares homology with transcriptional regulator genes. In addition cvm7 also shared 33% identity with one of the two genes identified in the paralogue cluster that did not have any obvious paralogues within the known clavulanic acid or clavam biosynthetic genes. Therefore since cvm6 and cvm6par have been shown to be paralogues, from this sequence data it can be concluded that cvm7 and cvm7par are paralogues of genes involved in 5S clavam biosynthesis.

BRIEF DESCRIPTION OF THE FIGURES

FIG. 1. Diagram of the paralogue cluster. The orientation of transcription is shown for each gene (direction of arrow)

FIG. 2. Orientation of cvm7 in relation to published cvm cluster (WO98/33896).

BRIEF DESCRIPTION OF THE SEQUENCES

Figure 3A:
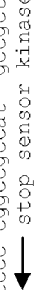
FIG. 3. Annotated seqence of the paralogue cluster

SEQ ID NO:1 cvm6para open reading frame
SEQ ID NO:2 cvm7para open reading fame
SEQ ID NO:3 cvm6para polypeptide
SEQ ID NO:4 cvm7para polypeptide
SEQ ID NO:5 cvm6 open reading frame
SEQ ID NO:6 cvm7 open reading frame
SEQ ID NO:7 cvm1 open reading frame
SEQ ID NO:8 cvm2 open reading frame
SEQ ID NO:9 cvm3 open reading frame
SEQ ID NO:10 cvm4 open reading frame
SEQ ID NO:11 cvm5 open reading frame
SEQ ID NO:12 orf2para open reading frame
SEQ ID NO:13 orf3para open reading frame
SEQ ID NO:14 orf4para open reading frame
SEQ ID NO:15 orf6para open reading frame
SEQ ID NO:16 paralogue cluster
SEQ ID NO:17 extended cvm cluster (underlined sequence denotes new sequence over that disclosed in WO98/33896
SEQ ID NO:18 orf2para open reading frame (reverse complement)
SEQ ID NO:19 orf3para open reading frame (reverse complement)
SEQ ID NO:20 orf4para open reading frame (reverse complement)
SEQ ID NO:21 cvm6 polypeptide
SEQ ID NO:22 cvm3 polypeptide
SEQ ID NO:23 orf6para polypeptide
SEQ ID NO:24 orf4para polypeptide
SEQ ID NO:25 orf3para polypeptide
SEQ ID NO:26 orf2para polypeptide Sequences SEQ ID NO: 1 cvm6para

ATGTTCCACCCGGTGCCGCCCCGGGGCCGCGAGGACCGCACCGTTCTGGTCTCCGGCCGCGGCTGCACCGTACGGGACAC

CGAAGGGCGCACCTATCTCGACGCCTCGTCGGTGCTCGGACTGACCCAGATCGGCCATGGACGTGAGGAGATCGCGCAGG

CCGCCGCCGAGCAGATGCGGACACTCGGTCACTTCCACACCTGGGGCACCATCAGCAACGACAAGGCCATCCGACTGGCC

GCGCGCCTCACCGACCTGGCGCCCCAGGGTCTCCAGCGCGTCTACTTCACCAGCGGCGGCGGCGAGGGCGTCGAGATCGC

CCTGCGCATGGCCCGTTACTTCCACCACCGCACCGGCAGCCCGGAGCGCACCTGGATCTTGTCGCGCCGCACCGCCTACC

ACGGCATCGGCTACGGCAGCGGTACGGTGTCGGGCTCGCCCGCCTACCAGGACGGGTTCGGCCCGGTGCTGCCCCATGTG

CACCACCTCACGCCGCCCGACCCGTACCACGCCGAGCTGTACGACGGCGAGGACGTCACGGAGTACTGCCTGCGCGAACT

CGCCCGCACCATCGACGAGATCGGCCCCGGGCGGATCGCCGCGATGATCGGGGAGCCGGTCATGGGCGCGGGCGGCGCCG

TCGTCCCGCCGCCGGACTACTGGCCGCGCGTCGCCGCGCTGCTGCGCTCCCACGGCATCCTGCTGATCCTGGACGAGGTC

GTCACCGCGTTCGGCCGCACGGGGACCTGGTTCGCGCGCCGAGCACTTCGGGGTGACCCCGATCTGCTGGTGACCGCGAA

GGGCATCACCTCCGGGTATGTCCCGCACGGGCGGTGCTCCTGACCGAGGAGGTCGCGGACGCCGTGAACGGGGAGACGG

GGTTCCCGATCGGCTTCACCTATACCGGTCACCCCACGGCGTGCGCCGTCGCGCTCGCCAATCTCGACATCATCGAACGG

GAAGGGCTGCTGGAGAACGCGGTGAAGGTGGGCGACCACCTCGCCGGGCGGCTGGCGGCCCTGCGCGGGCTGCCCGCCGT

GGGGGACGTCCGGCAACTGGGCATGATGCTCGCCGTCGAGCTGGTGTCGGACAAGACGGCCCGCACCCCGCTGCCGGGCG

GCACCCTCGGGGTCGTGGACGCGCTGCGCGAGGACGCGGGCGTCATCGTCCGGGCCACGCCGCGCTCCCTGGTCCTCAAT

CCGGCGCTCGTGATGGACCGGGCCACGGCGGACGAGGTGGCGGACGGGCTGGACTCGGTGCTGCGGCGGCTGGCACCCGA

CGGGCGGATCGGCGCGGCCCCCCGGCGGGGGTGA

SEQ ID NO: 2 cvm7para

GTGTACGAGTGCAGCGATGAGGTTCGTCACGACGTCCCCGGCCTGCCGGGTCCGTCACCGTCCATCACCGTCCTGGGCTG

TCTGGGCGTACGCGCCGACGGCCGGAAACTGGAGCTGGGCCCTCCGCGTCAGCGGGCCGTTTTCGCCCTGCTGCTCATCA

ACGCGGGCAGTGTGGTGCCGGTCGACTCGATCGTCTTCCGTATCTGGGGCAACTCACCACCGGGCGCGGTCACCGCGACG

CTCCAGTCCTATGTGTCCCGGCTGCGGAAACTCCTGGCCGAGTGTGTGCTCCCGGACGGTTCGACACCCGAACTGCTGCA

CCAGCCGCCGGGCTACACCCTCGCGCTCGGCACCGAGCACATCGACGCGAACCGTTTTGAGCAGGCCATCAGGACAGGGC

GCCGGCTCTCGCGCGAGGAGCAGCACCAGGAGGCGCGGGCCGTGCTCTGCCAGGCCCTGCTGAGCTGGGGCGGGACACCG

TACGAGGAGCTGAGCGCGTACGACTTCGCCGTCCAGGAGGCCAATCGGCTGGAGCAGCTCCGGCTGGGCGCCGTGGAGAC

ATGGGCGCACTGCTGTCTGCGGCTGGGGCGGGACGAGGAGGTGATGGACCAGCTCAAGCCGGAGGTGCAGCGCAATCCGC

TGCGGGAGCGGCTGATCGGCAGCTCATGCAGGCGCAGTACCGGCTGGGGTGCCAGGCGGACGCGCTCAGGACGTACGAG

GCGACGCGGCGGGCCCTGGCCGAGGAGCTGGGGACCGATCCGGGCAAGGAGCTGGCGGCGCTGCACGCGGCGATCCTGCG

TCAGGACAACGGTCTGGACCGCGTCGTCCCGGCGTCCGCGCCGCCGTCGGCGGGGGTCGGGCGGGGGCCGTGACGGTGT

CGGTCcCGGCACAGCGGTCGAGGCCGTTGACGCGGCCGGTGGCGGGCGGGCGCGGGTCCCGGGGGCGATGACGGTGGCG

GCGGGCGCGGGGCGGCCCCCGCGTCCGCCTCCGGCTCCGTTTCCGCGTCCGTTTCCGGCTCCGGCTCCGGCTC

CGCTCCTGCGTCGGTTCCCACCTTCTTTCCCGGCTCCGTTTCTGGCTCGGCGTCCGTTGCCGCGTCCGTAGCCGCGCCCG

TTTCCGGCCATGTCTCCGGGCCCGGGTCCGCTTTCGGGTCCGTGGCGCTCCACCGGCCGCAGACCCTCCGGGGCGAGCCG

GTCCACGGGGGCGCGCAGGGGATGCGCACCGGGCAGGTGTTCCCCACGCTGCCGCCGTTCGTCGGGCGCGGCGACGAGCT

GCGCGGTCTGCTGGAGTCCGCGACGTCCGCGTTCCACACCTCGGGGCGGGTGGCGTTCGTCGTCGGCGAGGCGGGCAGCG

GCAAGACCCGGCTCCTCTCCGAGTTGGAGCGCTCGGTTCCGGACAGTGTGCGCACCGTCTGGGCGTCCTGTTCGGAGAGT

GAGGACCGGCCCGACTACTGGCCGTGGACGACCGTGCTGCGGCATCTGTACGCGATGTGCCGGAACGTATGCACGGATT

CCCCGGTTGGCTGCGGCGCGCACTCGCGGAACTGCTTCCCGAGGTGGGCCCGGAGCCACAGGGGCCGCACTCCCCCGACG

-continued

```
GGGGCGAGGAGAACAGCGGCAACGGGACGGTGCGGGCGACGGGACAGCACCCCGGCGCACACCCTCACGCTCGCGCCC
GCTCTCGCGCCCCCGCGCTCCAGAGAGGCTCGTTTCACCCTGCACGACGCCGTGTGCCAGGCGCTTCTGCGCACGGTCCG
CGAACCCGTGGTGATCATGCTGGAGGACATGGAGCGGGCCGACGCCCCTCGCTCGCCCTGCTGCGCCTCCTGGTGGAGC
AACTGCGCACCGTCCCCCTGCTGCTCGTGGTCACCACGCGCACCTTCCGGCTCGCGCACGACGCCGAGCTGCGACGGGCC
GCCGCCGTGATCCTCCAGTCGACCGGCGCGCGCCGGGTCCTGCTGAACGCCCTGGACGCACGGGCCACCGGGGAACTCGC
CGGAGGGATGCTGGGCAAGGCCCCGGACACCCTCCTCGTACGGGCCCTGCACGAGCGCTCCGCCGGGAACCCGTACTTCC
TCGTCCAGCTCCTCCGCTCGCTCCGGCAGGGGCTCGCCGCCGCCTGGGAGACGGAGATCCCGGACGAGCTGGCCGGGGTC
GTGCTGCAACGGCTGTCGAGCGTGCCGCCCGCCGTGCGCCGGGTGCTCGACATCTGCGCGGTCGTGGAGCGCAGTTGCGA
ACGGCGTGTGATCGAGACCGTGCTGCGCCATGAGGGAATCCCGCTGGAGAACGTCCGTACGGCGGTCCGCGGCGGTCTGC
TGGAGGAAGACCCCGACGACCCCGGGCGGCTGAGGTTCGTGCATCCGCTGGTCCGGGAGGCCGTCTGGGACGACCTGGAG
AACACCCGTCGGCCCGTSTCVMARGTCCCGTTCCTCCGCGCTCGGGGCGCTGGCCACGGTCTGA
```

SEQ ID NO: 3 cvm6para polypeptide

```
MFHPVLPRGPEDRTVLVSGRGCTVRDTEGRTYLDASSVLGLTQIGHGREEIAQAAAEQMRTLGHFHTWGTISNDKAIRLA
ARLTDLAPQGLQRVYFTSGGGEGVEIALRMARYFHHRTGSPERTWILSRRTAYHGIGYGSGTVSGSPAYQDGFGPVLPHV
HHLTPPDPYHABLYDGEDVTEYCLRELARTIDEIGPGRIAAHIGEPVMGAGGAVVPPPDYWPRVAALLRSHGILLILDEV
VTAFGRTGTWFAAEHFGVTPDLLVTAKGITSGYVPHGAVLLTEEVADAVNGETGFPIGFTYTGHPTACAVALANLDIIER
EGLLENAVKVGDHLAGRLAALRGLPAVGDVRQLGMMLAVELVSDKTARTPLPGGTLGVVDALREDAGVIVRATPRSLVLN
PALVMDRATADEVADGLDSVLRRLAPDGRIGAAPRRG
```

SEQ ID NO: 4 cvm7para polypeptide

```
VYECSDEVRHDVPGLPGPSPSITVLGCLGVRADGRKLELGPPRQRAVFALLLINAGSVVPVDSIVFRIWGNSPPGAVTAT
LQSYVSRLRKLLAECVLPDGSTPELLHQPPGYTLALGTEHIDANRFEQAIRTGRRLSREEQHQEARAVLCQALLSWGGTP
YEELSAYDFAVQEANRLEQLRLGAVETWAHCCLRLGRDEEVMDQLKPEVQRNPLRERLIGQLMQAYRLGCQADALRTYE
ATRRALAEELGTDPGKELAALHAAILRQDNGLDRVVPASAPPSAGVGRGAVTVSVPAQRSRPLTRPVAGRARVPGAMTVA
AGAGAAPASASGSVSASVSGSGSGSGSAPASVPTFFPGSVSGSASVAASVAAPVSGHVSGPGSAFGSVALHRPQTLRGEP
VRGGAQGMRTGQVFPTLPPFVGRGDELRGLLESATSAFHTSGRVAFVVGEAGSGKTRLLSELERSVPDSVRTVWASCSES
EDRPDYWPWTTVLRHLYAMWPERMHGFPGWLRRALAELLPEVGPEPQGPHSPDGGEENSGNGDGAGDGDSTPAHTLTLAP
ALAPPRSREARFTLHDAVCQALLRTVREPVVIMLEDMERADAPSLALLRLLVEQLRTVPLLLVVTTRTFRLAHDAELRRA
AAVILQSTGARRVLLNALDARATGELAGGMLGKAPDTLLVRALHERSAGNPYFLVQLLRSLRQGLAAAWETEIPDELAGV
VLQRLSSVPPAVRRVLDICAVVERSCERRVIETVLRHEGIPLENVRTAVRGGLLEEDPDDPGRLRFVHPLVREAVWDDLE
NTRRPVSRSSALGALATV
```

SEQ ID NO: 5 cvm6

```
GTGCCCGGCTCCGGACTCGAAGCACTGGACCGTGCCACCCTCATCCACCCCACCCTCTCCGGAAACACCGCGGAACGGAT
CGTGCTGACCTCGGGGTCCGGCAGCCGGGTCCGCGACACCGACGGCCGGGAGTACCTGGACGCGAGCGCCGTCCTCGGGG
TGACCCAGGTGGGCCACGGCCGGGCCGAGCTGGCCCGGGTCGCGGCCGAGCAGATGGCCCGGCTGGAGTACTTCCACACC
TGGGGGACGATCAGCAACGACCGGGCGGTGGAGCTGGCGGCACGGCTGGTGGGGCTGAGCCCGGAGCCGCTGACCCGCGT
CTACTTCACCAGCGGCGGGGCCGAGGGCAACGAGATCGCCCTGCGGATGGCCCGGCTCTACCACCACCGGCGCGGGGAGT
CCGCCCGTACCTGGATACTCTCCCGCCGGTCGGCCTACCACGGCGTCGGATACGGCAGCGGCGGCGTCACCGGCTTCCCC
GCCTACCACCAGGGCTTCGGCCCCTCCCTCCCGGACGTCGACTTCCTGACCCCGCCGCAGCCCTACCGCCGGGGAGCTGTT
CGCCGGTTCCGACGTCACCGACTTCTGCCTCGCCGAACTGCGCGAGACCATCGACCGGATCGGCCCGGAGCGGATCGCGG
CGATGATCGGCGAGCCGATCATGGGCGCGGTCGGCGCCGCGGCCCCGCCCGCCGACTACTGGCCCCGGGTCGCCGAGCTG
```

-continued

```
CTGCACTCCTACGGCATCCTGCTGATCTCCGACGAGGTGATCACGGGGTACGGGCGCACCGGGCACTGGTTCGCCGCCGA
CCACTTCGGCGTGGTCCCGGACATCATGGTCACCGCCAAGGGCATTCACCTCGGGGTATGTGCCGCACGGCGCCGTCCTG
ACCACCGAGGCCGTCGCCGACGAGGTCGTCGGCGACCAGGGCTTCCCGGCGGGCTTCACCTACAGCGGCCATGCCACGGC
CTGCGCGGTGGCCCTGGCCAACCTGGACATCATCGAGCGCGAGAATCTGCTCGACAACGCCAGCACCGTCGGCGCCTACC
TGGGCAAACGCCTGGCCGAGCTGAGCGATCTGCCGATCGTCGGGGACGTCCGGCAGACCGGTCTGATGCTCGGTGTCGAA
CTGGTCGCCGACCGCGGAACCCGGGAGCCGCTGCCGGGCGCCGCCGTCGCCGAGGCCCTGCGCGAGCGGGCGGGCATCCT
GCTGCGCGCCAACGGCAACGCCCTCATCGTCAACCCCCCGCTGATCTTCACCCAGGAAGACGCCGACGAACTCGTGGCGG
GCCTGCGCTCCGTACTCGCCCGCACCAGGCCGGACGGCCGGGTGCTCTGA
```

SEQ ID NO: 6 cvm7

```
ATGAAGTACGACATAACCCCACCATCCGGCCTTCGGTTCGACCTCCTCGGCCCGTTGACCGTGACCGCCGGCGAGCAACC
CGTGGACCTGGGCGCGCCACGGCAGCGCGCCCTGCTCGCCCTGCTGCTCATCGATGTCGGCAACGTGGTCCCGCTGCCGG
TCATGACCGCGTCGATCTGGGGGGCCGACCCACCGTCCCGGGTCCGGGGACGCTCCAGGCTTATGTGTCCCGACTGCGG
AAACTCCTGCACCGCCATGACCGTTCCCTTCGCCTTGTCCACCAGCTCCAGGGGTATCTCCTCGAAGTGGATTCGGCGAA
GGTGGACGCCGTGGTTTTCGAGACACGTGTCAGGGAGTGCCGGGAATTGAGCAGGGCCCGGAACCCCGAGGCCACCCGGG
CCGTGGCCTGGTCCGCCCTGGAGATGTGGAAGGGCACACCCATGGGCGAGCTGCATGATTATGAATTTGTGGCGGCGGAG
GCCGACCGGCTGGAAGGAATCCGGTTACGCGCGCTGGAGACCTGGTCCCAGGCGTGTCTCGATCTCCAGCACTATGAAGA
GGTTGCATTTCAGCTCGGCGAGGAGATCCACCGCAATCCGGAACTGGAACGGCTGGGCGGTCTCTTCATGCGGGCCCAGT
ATCATTCCGGACGGTCGGCGGAAGCCCTGTTGACGTATGAACGTATGCGTACCGCGGTGGCGGAGAATCTGGGGGCCGAT
ATCAGTCCGGAGCTCCAGGAACTCCATGGAAAGATTCTGCGCCAGGAACTCACGGAGACACCCGCCGCGCGATCGACGGC
CTCCCTCACACGGGCGGCGGGCCCGCACGGGCCCCCGCCCCTGGCCGAAACCGGCACCCCCGCCGCACCCGCGGACATGG
CCGAAACCACGGTGGCGGAGGAAAGCGCCGCGCCCCCCGCCCCGGCGGCGCCCGGGACCCCGCCCCCCATGCCGTCCCCC
GTACCGCTCCCCCATCCGTCAGGGGCCGTCCCGCCGGTCACCCCGGTGCCTCCCCCGGTCCCCCGCTCGGCCCTCCGTTC
AGCGGCACCCGCCGAGACCGAGGACCCGGAACCGGCGCCGCCCCCTCCCCCTCCGCCGGGCGGCCGACTCATCGGCCGCC
GCGCCGAACTGCGCAGGCTGCGGCTGCTGCTGACGAAGACCCGCGCGGGCCACGGCCATGTCCTGCTGGTCTGCGGCGAA
CAGGGCATCGGGAAGACCCGGCTCCTGGAGCACACCGAGCACACCCTGGCCGCGGGCGCGTTCCGGGTGGTCCGTTCGCA
CTGCGTCGCCACCCTCCCGGCACCGGGCTACTGGCCCTGGGAGCACCTCGTACGCCAGCTCGACCCGGACAGCGGCCTCG
GTGACGACGGCGACGCCGACCCCGTCGCCCAGGCCGAGTGGCTGCCGGAACACCACCTCACCCACCAGATGCGGATCTGC
CGGACGGTGCTCGCCGCGGCGCGGCGGACCCCGCTCCTGTTGATCCTGGAGGATCTGCACCTCGCCCACGCGCCGGTCCT
GGATGTGCTCCAGCTCCTGGTCAAACAGATCGGCCAGGCCCCCGTCATGGTCGTCGCCACCCTGCGCGAGCACGATCTCG
CCCGGGACCCCGCCGTCCGCCGGGCCGTGGGCCGCATCCTCCAGGCGGGCAACACCGGCACCCTCCGGCTGGACGGGCTC
ACCGAGGAGCAGAGCCGGGAGCTGATCGTCTCGGTCGCGGGGCCCCGTTCGCGCCCCATGACGCCCAACGGCTCCAGCG
CGCCTCGGGCGGCAACCCGTTTCTGCTGCTCAGCATGGTCACAGGGGAGGACGGCACCCAGGAGTGGGCACGGCCGTGCG
TCCCGTTCGAGGTGCGCGAGGTGCTGCACGAGCGGCTGAGCGAATGCTCCCCGTCCACCCAGGACGTGCTCACGCTCTGC
GCCGTGCTCGGCATGAGCGTGCGCCGACCGCTGCTCACCGACATCATGTCCACGCTCGACATCCCGCACACCGCGCTCGA
CGACGCGCTCGGCACGGGGCTGCTGCGCCACGACCGGAACACCGACGGAATGGTCCACTTCGCCCATGGGCTGACCCGGG
ACTTCCTGCTCGACGACACCCCGCCGGTCACCCGCGCCCGCTGGCACCACCGGGTCGCCGCCACCCTCGCCCTGCGCTTC
CAGCAGGGCGACGACCACGCCGAGATCCGCCGCCACTGTCTGGCCGCGGCCCGTCTGCTCGGCGCCCGCGCGGGGGTGCG
CCCCCTGCTGGCGCTGGCCGACCGGGAGCAGTCCCGCTTCTCCCACGCGGAGGCGCTGCGCTGGCTGGAGAGCGCGGTCG
CGGTCGTCGCGCGCGCTGCCCCGGGACCAGCCGGTGTCCGCCGTCGAACTCCAGTTGCGCAAACGGATGATGGCGCTGCAC
GCGCTGATGGACGGCTATGGATCGGCCCGCGTCGAGACGTTCCTCTCCCAGGTCACCCAGTGGGAACACGTCTTCGACAA
```

CACCCAGCCCACCGGGCTGCTGCACGTCCAGGCGCTGAGCGCGCTCACCACGGGCCGCCATGAGCAGGCGGCGGAGCTGG

CCCGGGCTGCTGCACGAGCTGGCCGACCACGGCGGCGGACCGGAGGCCCGGTCGGCGGCCTGCTATGTGGACGGCGTCACC

CTGTATGTGGGCGGACGGGTCGACGAAGCCCTCGCCGCGCTCGCCCAGGGCACCGAGATCACGGACGCCCTCCTGGCCGG

ACACCGCAGGACCGCCGCCCCGCACGGCGGCGGGCACCTCCAGGACCGGCGTATCGACTTCCGCGCCTATCTGGCGCTCG

GCCACTGTCTCAGCGGCGACCGGATTCAGACCCAGCGCTACCGACGGAACTCCTCCACCTCACCCAGTCGGAACGGTAC

GACCGGCCGTGGGACCGGGCCTTCGCCCGCTATGTGGACGCGCTCATCGCCGTCACGGAGTGCGATGTCCAGGGGGTGTG

GCTGGCCGCGCGGGCGGGGCTCGACCTCGCCGCCCGCTGCCAGCTCCCGTTCTGGCAGCGGATGCTCGCCGTCCCCCTCG

GCTGGGCCGAGGTCCACCAGGGGGCGCACGACAAGGGGCTGGCCCGGATGCGGGAGGCGCTGCACGAGGCGGCCCGGCAC

CGGACCCTGCTGCGCCGTACGCTCCACCTCGGCCTGCTCGCCGACGCCCTCCAGTACACGGGCGCCCGGGAACAGGCCCG

GCGCACGATGTCCTCCGCCGTACGGGAGATCGAGCGCCGCGGCGAGTACTTCTGTCTCCGGCCGCAGTGGCCCTGGGCCC

GGCTCCTCCACAGCCACGGCACCTCCGCCGCGGCGGAGCACCGGGTCGTCCACGGCAGGCACTGA

SEQ ID NO: 7 cvm1

ATGTCCCGCTCTCCGCCCGAGTCCCCGGCCGGTTCCGTGTCCGCCGCGGTTCCGCGTCCGCCGGTCCGCGCCCTGCGGGA

CCTTCCGGTCAGTGCCCAGGGGCTCGGCTGCCTGCCGACCACCGACTTCTACGGACGCCCGGACCGCGCCCGGGCGACGG

CCACCATCCGCGCCGCCGTCGACGCCGGGGTCACCCTGCTGGACACCGCCGACGTCCAGGGGCTCGGCGCCGGTGAGGAG

CTGCTCGGACGGGCGGTCGCGGGCCGCCGGGACGAGGTGCTGATCGCCACCAAGTTCGGCATGGTGCGcTCGTCCGACGG

CGCCTCCCAGGGCTTGTGCGGCGAGCCGTCcTACGTCCGCGCGGCCTGCGAACGGTCCCTGCGTCGTCTCGGCACCGACC

GCATCGACCTGTACTACCAGCACTGGACGGACCCGGCGGTGCCGATCGAGGAGACCGTGGGTGCGGTGGCCGAGCTGGTG

CGCGAGGGCAAGGTCCGCAGGCTCGGTCTCTCCGAGCCCTCCGCGGCCACGCTGCGCCGGGCGGACGCGGTGCACCCGGT

GACGGCGGTGCAGAGCGAGTGGAGCCTGTGGTCGCGCGGGATCGAGGACGAGGTGGTGCCCGTCTGCCGGGAGCTGGGGA

TCGGGATCGTCGCTTACGCCCCTCTGGGACGGGGTTTTCTCACCGGCACCATCCGCACCACCGACGATCTGGGGGACGAG

GACTTCCGCCGGGGCCAGCCCCGGTTCAGCGCTCCGGCCCTCGCGCGCAACCGCTCGTTGCTGCACCGGCTGCGCCCGGT

CGCGGACGGTCTGGGGCTGACCCTGGCACAGCTCGCGCTCGCCTGGCTGCACCACCGGGGCGAGGACGTCGTCCCGATCC

CGGGCACCGCGAACCCGGCCCATCTCGCGGACAATCTCGCCGCCGCCTCGATCCGGCTGGACGACCGGTCCCTCGCGGAG

GTGACGGCCGCGATCTCCCACCCGGTGTCCGGGGAGCGGTACACCCCGGCATTGCTCGCCATGATCGGCAACTGA

SEQ ID NO: 8 cvm2

ATGTCCGTGGCATCGGCCGGTATGACGGACGAGCAGCGCAAGGCGGTCATCACCGCGTACTTCAAGGCGTTCGACAACGG

CGGCGTCGGCAGCGACGGCACCCCCGCGATCGACTACTTCGCCGAGGACGCGGTCTTCTTCTTCCCCAAGTGGGGTCTGG

CCCGGGGCAAGTCCGAGATCGCCCGGCTCTTCGACGACCTCGGGGGCACCATCCGCTCGATCACCCACCATCTGTGGTCC

GTCAACTGGATTCTGACCGGGACCGAACTCCTCGCCGCGAGGGCACCACCCACGGTGAGCACCGGGACGGGCCGTGGCG

GGCGGGTGACCCCGAGTGGGCCGCCGGGCGCTGGTGCACGGTCTACGAGGTGCGGGACTTCCTCGTCCACCGGGCCTTCG

TCTATCTGGACCCCGATTACGCGGGCAAGGACACCGCGCGTTACCCGTGGCTGTGA

SEQ ID NO: 9 cvm3

GTGACCCGGCCTCCGGGCCTTTCCGCGCACACCCACGGGTCCGTGTCCGGGAGTCTGCTGCGCCGGGTGGCGGGCCACTA

TCCCACCGGGGTGGTCCTGGTCACCGGTCCGCCGAGGCTCCGGGGCAGCCGCCGCCCGCCATGGTGGTGGGGACGTTCA

CCTCGGTGTCGCTCGATCCGGTGCTGGTGGGTTTCCTCCCGGCCAGGTCGTCGACGACCTGGCCGCGGCTCCGGGCGGCC

GGGCGTTTCTGCGTCAATGTGCTCGGCGCGGATCAGGGCCCGGTCTGCCGGAGTTTCGCCGGGGGCGATCCGGGGCGCTG

GGAGGTGCCGTACCGGACGACGGCCACCGGCTCCCCCGTCCTGCTCGACGCGCTCGCGTGGTTCGACTGCGAGGTGGCGG

GGGAGACGGAGGCGGGCGACCACTGGTTCGTCACCGGGGCGGTGCGCGACCTCGGGGTGATCCGCGAGGGTTCGCCCCTG

-continued

GTCTTCCTGCGGGGCGACTACGGGCACTGGGCCGGGGCGGCGGCTCGGCCGGGCGGGGCGGCGGTCCGCCGTCTGCCC

GGTCTGA

SEQ ID NO: 10 cvm4

GTGGAATGCCGCATATTCGAGATCGACGAACTGCCGTTGCTGGACGGGGAGGTCCTGCGGGACGCCCGGATCGGTTACGC

CATGTACGGCACGCCGAACGCCGACGGGACGAACGTGGTGCTCTGTCCGTCGTTCTTCGGCCGGGACCACACCGGGTACG

ACTGGCTGATCGGTGCGGGGCTGCCGCTGGACACCCGGCGGTACTGCGTCGTCACCGCCGGACTCTTCGGCAACGGGGTC

TCCAGCTCGCCCGGCAACCACCCGTCGGGGTCCCGCTTTCCGCTGATCACTCCGCAGGACAATGTCGCGGCGCAGCACCG

GCTGCTCACCGAGGAGCTGGGGGTACGGGAACTGGCCCTGGTCACGGGCTGGTCGATGGGCGCGGCCCACGCCTACCAGT

GGGCCGTGTCGCATCCGGGGATGGTGCGCCGGATCGCCCCGATCTGCGGGGCGCCGGTGAGCAGCCCGCACAGCCTGGTC

CTGCTGTCCGGTCTGGCCGCGCGCTCAGCGCCGACGCCGGGGAGCGGGGGCGGAAGGCGGCGGGCCGGGTGTTCGCCGG

GTGGGGGACCTCGCGTTCCTTCTGGGCCCGCCGTGCCCACCGGGAGCTGGGTTTCGCCACCCGCGAGGAGTACCTCACCG

GCTTCTGGGAGCAGGTCTTCCTCTCCGGGCCCGGCGCCGCGGATCTGCTCACCATGGTGCGCACCTGGGAGAACACGGAT

GTGGGGGCGACACCCGGGGCCGGGGGGAGCGTCGAGGCGGCGCTGGCCTCCGTCACGGCGCGGGCCGTGGTGCTGCCGGG

CGCCCTGGACGTGTGTTTCGCCGTCGAGGACGAGAAGCGGGTGGCCGATCTGCTGCCGTATGCCTCGCTGGAGGTGATCC

CGGGAGTGTGGGGGCATCTCGCGGGGTCCGGGGGGTCGGCCGCCGACCGGGAGTTCATCGGGGCGCGCTGCGGCGGCTG

CTGGACAGCCCGGTGGACGGGGGCTGA

SEQ ID NO: 11 cvm5

GTGAAGTCCATTCTCTTCTATCTGCCAACGGTCGGCAGTCATGCGCAGGTCCAGCGGGGTATGGCGGGGGTCAATCCGCA

GAACTACCAGAACATGCTCCGGCAGCTCACCCGGCAGGCGCAGGCGGCCGACGAACTCGGCTACTGGGGACTGTCCTTCA

CCGAGCACCACTTCCACACCGAGGGGTTTCGAGGTCTCCAACAACCCGATCATGCTGGGGCTCTACCTCGGCATGCAGACC

CGGCACATCCGGGTCGGCCAGATGGCCAACGTCCTGCCGCTGCACAATCCGCTGCGGCTGGCCGAGGATCTGGCGATGCT

CGACCACATGACCCGGGGCCGCGCCTTCGTCGGGATCGCGCGCGGGTTCCAGAAGCGCTGGGCCGACATCATGGGGCAGG

TGTACGGGGTCGGCGGCACCCTGTCCGACGCCGGGGAGCGGGACCGGCGCAATCGTGCCCTCTTCGAGGAGCACTGGGAG

ATCATCAAGAAGGCGTGGACGACCGAGACGTTCACCCACTCCGGGGAGCAGTGGACGATCCCGGTGCCGGACCTGGAGTT

CCCCTACGAGGCGGTGCGCCGCTACGGCCGGGGCCTCGACGAGAACGGCGTCATCCGCGAGGTGGGCATCGCGCCCAAGC

CCTACCAGCGCCCCCACCCGCCCGTCTTCCAGCCGTTCAGCTTCAGTGAGGACACGTTCCGGTTCTGTGCCCGGGAGGGC

GTGGTGCCGATCCTGATGAACACCGACGACCAGATCGTCGCCCGGCTGATGGACATCTACCGGGAGGAGGCCGAGGCGGC

GGGCCACGGCACCCTGCGGCGGGGCGAGCGGGTCGGGGTGATGAAGGACGTCCTGGTCTCCCGGGACTCCGGCGAGGCCC

ACCACTGGGCGTCCCGCGGCGGCGGCTTCATCTTCGAGAACTGGTTCGGCCCCATGGGCTTCACCGAGGCGCTGCGCGCG

ACCGGCGAGACGGGTCCGATCGGCTCGGACTACAAGACCCTGGTCGACCGGGGGCTGGAGTGGGTCGGCACCCCGGACGA

CATCAACCGCATGATCGAGAAGCTGGTGGAGCGGCACGATCCGGAGTATcTGCTCCAGTGCCAGTACTCCGGGcTGATCC

CGCACGATGTCCAGCTGCGCAGCCTGGAGCTGTGGGCCACCGAGATCGCCCCCAACTGGcTCTGA

SEQ ID NO: 12 orf2para

TCAGATGGCCAGGGCGGCGAAACCGCCGGACTGGAAGTCGTAGGCCACCGGTACCTCGATCAGGAACGGGCGGCCGAGTC

CGGCGCCCTTGGTGAGGGCGGCGAGCAGCGAGGTGCGGTCGGTGGCGCGGACGGCCTCGCAGCCGTTGGCCTCGGCGAGC

TGGACGAAGTCGACGCTTCCGAAGCCGACGGCGGGGCGTGGAGCGCTGGTGTCCGAGGTTCTGGTACAGCTCGATCAG

GCCGTTGCGGTCGTTGTTGACGACGACCATGACGATCGGCAGGCCCAGGCGCACGGCCGTCTCGATGTCGGCGCTGTTGG

AGTGGAAGCCGCCGTCGCCCGCGATGAGGAAGACGGGCTCGCCGGGCCGGGCGATCTGGGCGGCCATGGCGGCGGGCAGT

CCGTAGCCGAAGCTGGAGCAGCCCGCGGAGGTGAGGAATCCGTACGGCTGGTCGGACTTGGCGAAGAGCACGCCGTAGTG

GCGGAAGAAGCCGATGTCGCTGACGAAGGTGCCGTTGTCGAGGACGGAGTTCATGCAGTCGATCACCTGGTGGACCCGCA

-continued

```
TGCCGTCCTCGTACTCGGTGGGGTCGGCGAGGAATTCGGCGACGCGGGCGCGCAGGGCGCTGAGGTCGTGCCGGGTCTTG

GGGGCGAGGCCCGAGGTCGCGTCGTCGAGCGCGGTGACGAATTCGGCGACGTTGGTGACGATGTCGATGTCGGCGCGGAA

CAGCTCCGGGATCGGGTTGACCTCGGGGGCGACCCGGACCGTGGTCTTGGCCCGGCCCCGCGTCCACATGGAGGGGCGCA

GGTCCTCGGCGTAGTCGTAGCCGATCGCCAGGAGGAGGTCGGCGGGGCCGAAGATCTCGTCGAGGGCCGGGTGGCCGAGA

ATGCCGTCCATGTAGCCGCTGATGGCGCCGTAGTTGAGCGGGTGGTCGTGCGGCAGGACGCCCTTGGCGGTGTAGGTGGT

GACGACGGGGATGTTCAGCCGCTCGGCGAGGGCGCGCAGGGCGTCGACGGCCCCGGCGCGGATGACGGCGCTACCGACGA

CGAGGAGGGGGTTCTCGGCCTCGCGCACCAGCTCAGCGGCCTCGTCGAGGCGGGCGCGCCAGTCGGCGTCCAGGGCGTGG

GTGGCGGTGGCCCGGACCAGGGGGCGTCGGTGGGGGTGCCGTTCAGCTCGGCGCCGAGGAGGTCGACCGGCAGGCTGAT

GAAGCTGGGACCCACGGGCTCGATCCGGCTGTTGAGGACGGCGCTGTCGACGAGGTTGACGATGTCCTCGCCGCGTTCGA

GCTGGACGCTGAACTTGGTCAGCGGGCCCATCACGGCGGTGCTGTCCAGGCACTGGTGGGTGACGTTGGGGTAGCAGTCG

TACGACTCGGACTGCGCGGCCAGCGCGATGACCGAGCTGCGGTCCAGGGCGGAGGTGGCGACGCCGGTGGCCAGGTTGGT

CATGCCGGGGCCCAGGGTCGCGAAGCACGCCTGGGGGCGGTTGGTGATCCGGGCGAGGACGTCCGCCATCACCCCGGCGG

TGAACTCGTGCCGGGTCAGGACGAAGTCGAGTCCTTCGACCTCGTCGAAGAGAATGGCGGACGCCTCCCGGCCGACGACG

CCGAATACATGGTCGACACCGTACTGGTGAAGACGTTCCAGCATGGCTTTCGCGGTCGTGGTGGCCAT
```

SEQ ID NO:13 orf3para

```
TCATACGACCACCCGGCCCTGGAGCCTGAGCCTGCGCACCGCGTCGACGGAGCGCCGCACCGTCTCGCCGAAGTCCACGT

CCTCCGGCGGCACCGTGTCGATGACCACCGCGTCGTACAGGCGCCGTGCCATGGCGCCCTTGACGGCCGTCACCTCGTCG

CGCCGGATCCCTTCGGCGAGGAGCAGTCCGGTCCACGCGCTGGTGGTGCCGGACCCCTCGTGGATGCCCAGCTTGGGGCG

GGCCACGGTCTCGGCGGGCAGCAGGCCGGAGAGGGCCTGCCGCAACACCCACTTGTCGGTGCCCCGCCGCGTTTGAGCC

CGGGTTCGAGGGAGACCAGCGCGTCCAGGACCGCGCGGTCCCAGTACGGGTGGGTGGTCCACTTCCCGGCGATGCCCGCG

AGGACGGGGGACATCTCGTTGAGGCCGTCGAAGCCCGCCATGTCGCCCGCGATCTCGTCGTCGAGGGACCAGAGCGAGGC

CGTGCGCCGGTGCATACCGCCGAGCGGGATGTCGGCGCCGTACCCGGTGAGGATGCGGAGCGGCCCGGTGTCGAGCCGCC

GGTAGAGGGCGACGAGCGGCAGCAGGTACTCCAGGACCGTGGGGTCGGTGATCTCCGCGGCGGCGACCGCCCAGGGCAGT

TCCCTGACGAGTTCGGCCGAGTGGAGCCGGATCTCGCTGTGCGCGGTGCCCAGGTGGACGGCGACCGAGCGGGCCGCGTC

GAACTCGTCGGACACCTCGGTGCCCATCGACACGGACCGTGTCCCGGGTGCCAGGGCCGCCGTGTGGGCGGCGACTCCCC

CGGAGTCGATGCCGCCGGACAGGACGACGGTGGGGGCCGCCTCCCCGCCGCGCAGCCGGGTGCGGACCGCCGTGGCGAGG

CGTTCGCCGACCAGGTCCACCGCCTCCCGTTCGCCGGGCAGCGCCCGGGAGAGCGGGGGTGTCCAGGTGCGGACCGCCCT

GGCGGTGATGTCGGAGCCGCCGACTCCGTGCAGCAGGAGGGCGGTCCCGGCGGGGACCCGGCAGACGCCCGCCGCCCCCG

GCGCGGTGTGGGTGCCGGACAGGCCCAGCGGCCGGCCCGGCTCGTGCGCCAGGGTCTTCGCCTCGGTGGCGGCGCTCAGC

CCCGTCACGTCGGCGCGCAGCCACAGCGGTACCGAACCGGCGTGGTCGGTGGCCGCGACGGTCGCGCCGGTGGAGGCGTC

GGTGAGCAGTGCGGCGAACCGTCCGTTCAGGAGCCGGAAGGCCCCGGGGCCCCAGCGCCGCCAGGCGGCCAGCAGCAGTT

CGGCGTCGCCGAGGGCGGCAGAGGAGCCGCCGAGCGCTCCGGTCAGCTCGGCGCGGTTGTACAGCTCGCCCGCCAGGAGC

AGCCGGACCTGGCCGTCGGCGACCAGGACGGGCGGACGGCCCAGGGTCACGGCCGTTCCGCTCCAGAGCGGGTACGCGGT

GCCGTCGTGCACGGGGACATGGGTCCCGCGGACGGCGAAGCGGGGTGCGCTGCCGGGTTCGGAGTGACCGCCGGGGCCGC

CGCCGGGGCGGCCCTCGGTGCCGATGCGCACCCGGAATCCGTACACGAGGTCGGGGCCGGGCAT
```

SEQ ID NO: 14 orf4para

```
CTACCCCCACCGCTGCCCGGCGAAGTCCACGGCGCTCTCGGCGTCCACCGCGTCCACCGCGTTCTCGGCGTTCTCGGCGT

CGTCCGCCGCCGCCCCGGTGGCAGGGGAGAGTCCACCGGTGCCGACGCGGGCGACGTGGTGGCGCGGGCGTACTGGTAG

AGCAGTTCGGCCCCGATCTCCGCCGCCAGCAGGGAGGTGATCCCCGACGGGTCGTACGCCGGGGACACCTCGACCACGTC

GAAGCCGACGGGCCTGAGCTGCCCGACCACGTCGAGCAGGGTCAGCACCTCGCGCGAGGACAGCCCGCCGGGGGCCGGTG
```

-continued

```
TGCCGGTGCCCGGGGCGTACGCCGGGTCGACGACGTCGATGTCGACGGAGACGTACAGCGGCAGGCCGCCGACGGTGCGC

CGGATCTGCTCGGCGATGCCGCGCGGTGAGCGCCGGGTGAAGTCGGCGGCGGTGACGATGCTGACGCCGTGCCCGCGCGC

GTAGTCCAGGGAGTCGGGCCGCGGATTGTGGCCGCGGATGCCGACCTGGACCAGGCGCTCCGGGTCCACCAGGCCCTCTT

CGATGGCCCAGCGGAAGGGGGTGCCGTGGTGGTAGGTGCCGCCGTAGACGGGTGGGTTGGTGTCGCTGTGCGCGTCCAGG

TGCAGGACGGCGACCCGGCCGTGGCGGGCGTGCACGGCGCGCAGGGCGGCCAGGGAGAGCGAGTGGTCCCCGCCCAGCAT

CAGGAACGCGTCGTTGCGTTCCAGGAGCCGGGTCAGGGCGACCGTCGCGGTGTCCATCGCCAGGTCCATCGAGAAGGGGC

TGAGGTCGATGTCGCCCCCGTCGACCACGTCGATCCGGTCGAAGACCCCTGGGCCCCGGTCGATGCCGACGCCGTGGATC

AGGCTGGACTCGTGCCGGATGGCGCGCGGCGCGAACCGCGCGCCGGGCCGGTAGCTGGTGCCTCCGTCGTACGGGCGCC

GACGACCACCACGTCATGGCCGATCGGGTCGGGCCGGTGGCGCAGCCGCATGAAGGTCGCCGGTTGGGCGTAGCGCGGGG

AGACGGCGGTGGACAC
```

SEQ ID NO:15 orf6para
```
ATGCGTGCCTCTTCGCCCAGAGGGTTCCGCGTGCACCACGGTCACGCCGGGATCAGGGGGTCCCACGCGGACCTCGCCGT

CATCGCCTCCGACGTTCCCGCGGCGGTCGGCGCGGTGTTCACCCGTTCGCGGTTCGCCGCGCCGAGTGTGCTGCTCAGCC

GGGACGCGGTCGCCGACGGGATCGCCCGGGGCGTGGTGGTGCTGTCCGGCAACGCCAACGCCGGGACGGGCCCGCGGGGG

TACGAGGACGCCGCGGAGGTGCGCCATCTGGTGGCCGGGATCGTCGACTGCGACGAGAGGGATGTGCTGATCGCCTCCAC

GGGACCCGTCGGCGAGCGGTATCCGATGTCCCGTGTCCGGGCCCATCTGCGGGCGGTGCGCGGGCCCTTACCGGGTGCCG

ACTTCGACGGCGCGGCGGCGGCCGTGCTGGGCACCGCGGGCGCCCGTCCCACGATCCGGCGGGCGCGGTGCGGCGACGCG

ACGCTGATCGGTGTCGCCAAGGGCCCGGGTACGGGCCCGGCGGAGCAGGACGACCGGTCGACGCTGGCGTTCTTCTGCAC

GGACGCCCAGGTGAGCCCCGTCGTCCTCGACGACATCTTCCGCCGGGTCGCGGACCGCGCCTTCCACGGGCTGGGCTTCG

GCGCCGACGCCTCCACCGGCGACACGGCGGCCGTTCTCGCCAACGGGCTCGCGGGCCGGGTGGACcTCGTCGCGTTCGAA

CAGGTCCTGGGCGCGCTGGCGCTGGACCTGGTCAGGGACGTCGTCCGGGACAGCGGCTGCGGCGGCGCCCTGGTCACGGT

GCGGGTCACCGGGGCCCACGACACCGAGCAGGCCGGGCGCGTGGGCCGGGCGGTGGTCGACGCGCCGTCGCTGAGGGCCG

CGGTGCACGGCCCGGCACCCGACTGGGCGCCGGTCGCCGCCGTGGCGGGTGGACACGGGACGAAGGCCCCGGCCGGTCT

CCCGGGCGGATCACGATCCGGGTCGGCGGCCGGGAGGTCTTCCCCGCCCCCGCGACCGGGCCCGCCCGGACGCCGTCAC

CGCGTATCCGCACGGCGGCGAGGTGACCGTCCATATCGACCTCGGTGTCCCGGGCCGGGCGCCCGGCGCGTTCACGGTCC

ACGGCTGCGACCTCCTGGCGGGGTACCCGCGCCTCGGCGCCGGCCGGGCCGTCTGA
```

SEQ ID NO: 16 para cluster
```
CCATGGGAGCAGCATCGCAGTGCGCCTCCCCGGCCGCCATGCCGCTAGCTGGTAGTCCCCCTGCCGGGTGCCGACCGCCG

GGGCGGTCCCGGGTGCGGCGGCCGGATCTAGTCGGTGTGCTCCGACGGTGCCTGCTGGGTGAGGGGCAGTGTCAGGCGGA

TGGTGGTTCCCGCGCCGGGCGGGCTGTGCAGCCGCAGTTGGCCGCCGAGTGCCTCCACCCGGTCGGTGAGGCCGACGAGG

CCCGAGCCCCGGCAGGGGCGGCGCCACCGCGGCCGTCGTCGCGGATGCCGACGTGGAGCCGTCCGTCCCGGGTGGCCAC

ATGGACGTCGACGACGGTGGCACCGGAGTGCTTGGCGGCGTTGGTCAGGGCCTCGGAGACGGCGTAGTACGCGGCGGTCT

CGACCGGTTCGGGGTGGCGTTCCCCGGTCTGGATGTCGAGCCGGACCGGGATGGCGGAGCGCCGGGCCAGGGCCTTGAGC

GCCGGGCGGAGTCCGCCCTCGGCGAGTACCGCCGGGTGGATGCCCCGGGCGACCTCCCGGAGTTCGTCGACGGCGGCGGC

CAGCCCGTCGGTCACCTCGTCGAGCTGCCGGATCAGCTCGTCGGCGTCGAGCGGCACCGACAGTTGCACGGTGCGCACCC

GCAGCGCCAGGGAGACCAGGCGCTGTTGGGGCCGTCGTGCAGGTCGCGTTCGATACGGCGGCGGCGGTGTCGGCGGCG

GCGACGATCCGGGCCCGTGACGCGGTGAGGGCCGCCTGCGTCTCCGCGTTGGCGATGGCGGTGGCCACCAGTTCGGTGAA

GCCGGCCAGCCGGTCCTCGGTGTCCGACGGCATCGGCTTGTCGTTCATCGACGCCACGCTGAGCGCGCCCCACAGTTGTC

CGTCGACGTTGATCGGCATGCACACCGTGGCGCGGAATCCCCACTCCTTGCCGACGACGGAGGCCGGGCCCGAGGACACG

GCCGCGTAGTCGTCGATCCGCGCCGGGCAGCCCGACTCGAACACCAGGGTGTGCACATTCCGGCCGCCGGGCGGTACCTG
```

-continued

```
GATACCGGCGGGAAAATCACGGCCGGTCCTGGTCCAGGCGGCGACATACAGGGCGGTTCCGTTGGGCTCGTAACGGCCGA
GGACCGCGAAGTCGGCCGAGAGGAGCTGTCCGGCCTCGGCGGCGACCGCGGCGAACACCTCCTTCGGCGGTGCCGCCCGC
GCGACCAGGGTCGCCACGCGCCGCAGCGCCGCCTGCTCCTCGGCGGCCCCCGCAGCTCCACACGTGCCTGGGTGTTCGC
GATGGCGGTGGCCACGAGGTCGGTGAAACCGGCCAGCCGGTCCTCGGTGTCGGGCGGCAGCGGTTCCGCGGTCAGCGAGA
TCGCCATCATCACGCCCCACAGCCGTCCCTCGACGTTGATCGGCACGCCGACGACCGAACCGAAGCCGCGCGCCCTGGCG
AAGTCGGCGGGTGCCCCGGACGACTCGGCGGCGTCGTCGATCCGGGCCGGCCGCCCCGTCTCGGACACCAGCGTCACCAC
GTTCCGGCCGTCGGGGTCCACCCGGGTGCCGATGGGGAAGAGCGGGCCGTGCAGACTTCTGGACCAGCCGCCGACGGCGC
TCGCCATGCCGTCCGGATCGAGCCTGATGATTCCGGTCACATCGTTGCCGAGCAGTTCTCCGACTTCGGCGGCGACCGTC
GCGAACATCTGTTCCGGTGGGGTGGCCCTGGCCACCAGGGTCGCCACCCGTCGGAGTGCCGCCCGCTCCTCGACGATCTG
TTCGCACGACACGACCGCTGCCAGGCCCCCCTACCCGCCCGATGACGCCCGCATACCGGGTATCACGGCACATCAGCATG
ACGTCCGCCGTGAACGCCCGTCAACGTGGCCCGCCGGAGTCGGGAACACGCGTCCGGAATCAGCCCCCGGAACGGCGGGA
CCGTCTTCCTCCGTCCGGCGCGGGGCACTGCGCCGCGGCGGAATCCGCCCTGACCTCGGGAGTTTGCAGCTAGCTGGAAT
CAGCGGTTCGGGTTGGTGGGAAGGGATGTTGGCCGCTGGCGGCGATGCGGAAGCCGATCGTTCCCAGTACTTCTGGGAAG
TGCGTCGCGGAGAGTCGGTCCGCTTCCCCGAGTGGGCCGCGACGACGCTGCGGGTTCTCCACGGGGAGAGATCCGCGAA
CCGGCGAAGGAGCTGCCGTGTCGGACGTCTTCGCATCCGAGAAGAGTTCGCCCGGTGTCCGGACCCGCGCGGCAACGTCC
CCACCGCGCTCTGTCATCAGCGCCGTCGGCGCCGTCAGCCACGCAGAGAAGATCGGATACGCAGTGTACGAGTGCAGCGA
TGAGGTTCGTCACGACGTCCCCGGCCTGCCGGGTCCGTCACCGTCCATCACCGTCCTGGGCTGTCTGGGCGTACGCGCCG
ACGGCCGGAAACTGGAGCTGGGCCCTCCGCGTCAGCGGGCCGTTTTCGCCCTGCTGCTCATCAACGCGGGCAGTGTGGTG
CCGGTCGACTCGATCGTCTTCCGTATCTGGGGCAACTCACCACCGGGCGCGGTCACCGCGACGCTCCATGCCTATGTGTC
CCGGCTGCGGAAACTCCTGGCCGAGTGTGTGCTCCCGGACGGTTCGACACCCGAACTGCTGCACCAGCCGCCGGGCTACA
CCCTCGCGCTCGGCACCGAGCACATCGACGCGAACCGTTTTGAGCAGGCCATCAGGACAGGGCGCCGGCTCTCGCGCGAG
GAGCAGCACCAGGAGGCGCGGGCCGTGCTCTGCCAGGCCCTGCTGAGCTGGGGCGGGACACCGTACGAGGAGCTGAGCGC
GTACGACTTCGCCGTCCAGGAGGCCAATCGGCTGGAGCAGCTCCGGCTGGGCGCCGTGGAGACATGGGCGCACTGCTGTC
TGCGGCTGGGGCGGGACGAGGAGGTGATGGACCAGCTCAAGCCGGAGGTGCAGCGCAATCCGCTGCGGGAGCGGCTGATC
GGGCAGCTCATGCAGGCGCAGTACCGGCTGGGGTGCCAGGCGGACGCGCTCAGGACGTACGAGGCGACGCGGCGGGCCCT
GGCCGAGGAGCTGGGGACCGATCCGGGCAAGGAGCTGGCGGCGCTGCACGCGGCGATCCTGCGTCAGGACAACGGTCTGG
ACCGCGTCGTCCCGGCGTCCGCGCCGCCGTCGGCGGGGGTCGGGCGGGGGGCCGTGACGGTGTCGGTCCCGGCACAGCGG
TCGAGGCCGTTGACGCGGCCGGTGGCGGGGCGGGCGCGGGTCCCGGGGGCGATGACGGTGGCGGCGGGCGCGGGGCGGC
CCCCGCGTCCGCCTCCGGCTCCGTTTCCGCGTCCGTTTCCGGCTCCGGCTCCGGCTCCGGCTCCGCTCCTGCGTCGGTTC
CCACCTTCTTTCCCGGCTCCGTTTCTGGCTCGGCGTCCGTTGCCGCGTCCGTAGCCGCGCCCGTTTCCGGCCATGTCTCC
GGGCCCGGGTCCGCTTTCGGGTCCGTGGCGCTCCACCGGCCGCAGACCCTCCGGGGCGAGCCGGTCCACGGGGGCGCGCA
GGGGATGCGCACCGGGCAGGTGTTCCCCACGCTGCCGCCGTTCGTCGGGCGCGGCGACGAGCTGCGCGGTCTGCTGGAGT
CCGCGACGTCCGCGTTCCACACCTCGGGGCGGGTGGCGTTCGTCGTCGGCGAGGCGGGCAGCGGCAAGACCCGGCTCCTC
TCCGAGTTGGAGCGCTCGGTTCCGGACAGTGTGCGCACCGTCTGGGCGTCCTGTTCGGAGAGTGAGGACCGGCCCGACTA
CTGGCCGTGGACGACCGTGCTGCGGCATCTGTACGCGATGTGGCCGGAACGTATGCACGGATTCCCCGGTTGGCTGCGGC
GCGCACTCGCGAACTGCTTCCCGAGGTGGGCCCGGAGCCACAGGGGCCGCACTCCCCGACGGGGCGAGGAGAACAGC
GGCAACGGGACGGTGCGGGCGACGGGACAGCACCCCGGCGCACACCCTCACGCTCGCGCCCGCTCTCGCGCCCCGCG
CTCCAGAGAGGCTCGTTTCACCCTGCACGACGCCGTGTGCCAGGCGCTTCTGCGCACGGTCCGCGAACCCGTGGTGATCA
TGCTGGAGGACATGGAGCGGGCCGACGCCCCCTCGCTCGCCCTGCTGCGCCTCCTGGTGGAGCAACTGCGCACCGTCCCC
CTGCTGCTCGTGGTCACCACGCGCACCTTCCGGCTCGCGCACGACGCCGAGCTGCGACGGGCCGCCGCCGTGATCCTCCA
```

-continued

```
GTCGACCGGCGCGCGCCGGGTCCTGCTGAACGCCCTGGACGCACGGGCCACCGGGGAACTCGCCGGAGGGATGcTGGGCA
AGGCCCCGGACACCCTCCTCGTACGGGCCCTGCACGAGCGCTCCGCCGGGAACCCGTACTTCCTCGTCCAGCTCCTCCGC
TCGCTCCGGCAGGGGCTCGCCGCCGCGTGGGAGACGGAGATCCCGGACGAGCTGGCCGGGGTCGTGCTGCAACGGCTGTC
GAGCGTGCCGCCCGCCGTGCGCCGGGTGCTCGACATCTGCGCGGTCGTGGAGCGCAGTTGCGAACGGCGTGTGATCGAGA
CCGTGCTGCGCCATGAGGGAATCCCGCTGGAGAACGTCCGTACGGCGGTCCGCGGCGGTCTGCTGGAGGAAGACCCCGAC
GACCCCGGGCGGCTGAGGTTCGTGCATCCGCTGGTCCGGGAGGCCGTCTGGGACGACCTGGAGAACACCCGTCGGCCCGT
GTCCCGTTCCTCCGCGCTCGGGGCGCTGGCCACGGTCTGAGTCCCGGGCCCGGGGTCCTCGGCGGCGGGCGGCGCTTGC
GCGCTCCCCGACGCCGGGCTTGATCCCCCGGGGCAGCCGGACGCGCAGCCGGGTGCAAGGGGCGGTGCCGACACTGGGCG
GGCGGCGGCCGTGGCCGGTCGCCGCCCCCACGGCCCACCGAGGAGCCCCCATTGGACACGTACGCAGCGGATACGTACC
CGCGGTCCGGCACCCACCCCGAGCCGCGTCCCGACGCACCTCCCCACGCGCGTCCCGGGACCCGTCCCGGCACCCGTTCC
GAGCCGCGCCCGGACCCGGGCGCCGAGGCCGCGTGGCTGCTCGCGGCGGACCGCGCCCATATGTTCCACCCGGTCCTGCC
CCGGGGCCGCGAGGACCGCACCGTTCTGGTCTCCGGCCGCGGCTGCACCGTACGGGACACCGAAGGGCGCACCTATCTCG
ACGCCTCGTCGGTGCTCGGACTGACCCAGATCGGCCATGGACGTGAGGAGATCGCGCAGGCCGCCGCCGAGCAGATGCGG
ACACTCGGTCACTTCCACACCTGGGGCACCATCAGCAACGACAAGGCCATCCGACTGGCCGCGCGCCTCACCGACCTGGC
GCCCCAGGGTCTCCAGCGCGTCTACTTCACCAGCGGCGGCGGCGAGGGCGTCGAGATCGCCCTGCGCATGGCCCGTTACT
TCCACCACCGCACCGGCAGCCCGGAGCGCACCTGGATCTTGTCGCGCCGCACCGCCTACCACGGCATCGGCTACGGCAGC
GGTACGGTGTCGGGCTCGCCCGCCTACCAGGACGGGTTCGGCCCGGTGCTGCCCCATGTGCACCACCTCACGCCGCCCGA
CCCGTACCACGCCGAGCTGTACGACGGCGAGGACGTCACGGAGTACTGCCTGCGCGAACTCGCCCGCACCATCGACGAGA
TCGGCCCCGGGCGGATCGCCGCGATGATCGGGGAGCCGGTCATGGGCGCGGGCGGCGCCGTCGTCCCGCCGCCGGACTAC
TGGCCGCGCGTCGCCGCGCTGCTGCGCTCCCACGGCATCCTGCTGATCCTGGACGAGGTCGTCACCGCGTTCGGCCGCAC
GGGGACCTGGTTCGCGGCCGAGCACTTCGGGGTGACCCCCGATCTGCTGGTGACCGCGAAGGGCATCACCTCCGGGTATG
TCCCGCACGGGGCGGTGCTCCTGACCGAGGAGGTCGCGGACGCCGTGAACGGGGAGACGGGGTTCCCGATCGGCTTCACC
TATACCGGTCACCCCACGGCGTGCGCCGTCGCGCTCGCCAATCTCGACATCATCGAACGGGAAGGGCTGCTGGAGAACGC
GGTGAAGGTGGGCGACCACCTCGCCGGGCGGCTGGCCGGCCCTGCGCGGGCTGCCCGCCGTGGGGACGTCCGGCAACTGG
GCATGATGCTCGCCGTCGAGCTGGTGTCGGACAAGACGGCCCGCACCCCGCTGCCGGGCGGCACCCTCGGGGTCGTGGAC
GCGCTGCGCGAGGACGCGGGCGTCATCGTCCGGGCCACGCCGCGCTCCCTGGTCCTCAATCCGGCGCTCGTGATGGACCG
GGCCACGGCGGACGAGGTGGCGGACGGGCTGGACTCGGTGCTGCGGCGGCTGGCACCCGACGGGCGGATCGGCGCGCCC
CCCGGCGGGGGTGACGAGACCGCGGGCCGCCACCCGCGGGGGGCGCCGGGTCGGCACAGCGGCCGACCCGGCGCCTTCCC
CGTTTCCCGGCGCCTTTTCCGTGCCCCGGCGCCGTTCCCGTGGCCCCTGCCCCTGCCCCTGCTCGGGCGCTCCTCCCTCC
GCTGTGGCGCCGTTCCCGTTCCAGCGCGCTGTCGAGCCGCCGCCAAGCGCCCCGTGCCACGGTGGGAGACCGCCGCCCGA
CGGGGCGCGCGGAGCCCGGCAAGCCGAAGGGAAGTCCCGTCCGATGCGTGCCTCTTCGCCCAGAGGGTTCCGCGTGCACC
ACGGTCACGCCGGGATCAGGGGGTCCCACGCGGACCTCGCCGTCATCGCCTCCGACGTTCCCGCGGCGGTCGGCGCGGTG
TTCACCCGTTCGCGGTTCGCCGCGCCGAGTGTGCTGCTCAGCCGGGACGCGGTCGCCGACGGGATCGCCCGGGGCGTGGT
GGTGCTGTCCGGCAACGCCAACGCCGGGACGGGCCCGCGGGGGTACGAGGACGCCGCGGAGGTGCGCCATCTGGTGGCCG
GGATCGTCGACTGCGACGAGAGGGATGTGCTGATCGCCTCCACGGGACCCGTCGGCGAGCGGTATCCGATGTCCCGTGTC
CGGGCCCATCTGCGGGCGGTGCGCGGGCCCTTACCGGGTGCCGACTTCGACGGCGCGGCGGCGGCCGTGCTGGGCACCGC
GGGCGCCCGTCCCACGATCCGGCGGGCGCGGTGCGGCGACGCGACGCTGATCGGTGTCGCCAAGGGCCCGGGTACGGGCC
CGGCGGAGCAGGACGACCGGTCGACGCTGGCGTTCTTCTGCACGGACGCCCAGGTGAGCCCCGTCGTCCTCGACGACATC
TTCCGCCGGGTCGCGGACCGCGCCTTCCACGGGCTGGGCTTCGGCGCCGACGCCTCCACCGGCGACACGGCGGCCGTTCT
CGCCAACGGGCTCGCGGGCCGGGTGGACCTCGTCGCGTTCGAACAGGTCCTGGGCGCGCTGGCGCTGGACCTGGTCAGGG
```

-continued

```
ACGTCGTCCGGGACAGCGGCTGCGGCGGCGCCCTGGTCACGGTGCGGGTCACCGGGGCCCACGACACCGAGCAGGCCGGG
CGCGTGGGCCGGGCGGTGGTCGACGCGCCGTCGCTGAGGGCCGCGGTGCACGGCCCGGCACCCGACTGGGCGCCGGTCGC
CGCCGTGGCGGGTGGACACGGGGACGAAGGCCCCGGCCGGTCTCCCGGGCGGATCACGATCCGGGTCGGCGGCCGGGAGG
TCTTCCCCGCCCCCCGCGACCGGGCCCGCCCGGACGCCGTCACCGCGTATCCGCACGGCGGCGAGGTGACCGTCCATATC
GACCTCGGTGTCCCGGGCCGGGCGCCCGGCGCGTTCACGGTCCACGGCTGCGACCTCCTGGCGGGGTACCCGCGCCTCGG
CGCCGGCCGGGCCGTCTGAACGGGCGCTCCCGGGCGGACGGCGACCGCGAGGGCGCGGGAGCGCAGGGAACACGGGAGCG
GGCCCGGTGGTCGATCGGCCACCGGGCCCGCTCCCGTCGTTCCGTCCGCTGTCCCCGGCCGCCCTACCCCCACCGCTGCC
CGGCGAAGTCCACGGCGCTCTCGGCGTCCACCGCGTCCACCGCGTTCTCGGCGTTCTCGGCGTCGTCCGCCGCCGCCCCC
GGTGGCAGGGGAGAGTCCACCGGTGCCGACGCGGGCGACGTGGTGGCGCGGGCGTACTGGTAGAGCAGTTCGGCCCCGAT
CTCCGCCGCCAGCAGGGAGGTGATCCCCGACGGGTCGTACGCCGGGGACACCTCGACCACGTCGAAGCCGACGGGCCTGA
GCTGCCCGACCACGTCGAGCAGGGTCAGCACCTCGCGCGAGGACAGCCCGCCGGGGGCCGGTGTGCCGGTGCCCGGGCG
TACGCCGGGTCGACGACGTCGATGTCGACGGAGACGTACAGCGGCAGGCCGCCGACGGTGCGCCGGATCTGCTCGGCGAT
GCCGCGCGGTGAGCGCCGGGTGAAGTCGGCGGCGGTGACGATGCTGACGCCGTGCCCGCGCGCGTAGTCCAGGGAGTCGG
GCCGCGGATTGTGGCCGCGGATGCCGACCTGGACCAGGCGCTCCGGGTCCACCAGGCCCTCTTCGATGGCCCAGCGGAAG
GGGGTGCCGTGGTGGTAGGTGCCGCCGTAGACGGGTGGGTTGGTGTCGCTGTGCGCGTCCAGGTGCAGGACGGCGACCCG
GCCGTGGCGGGCGTGCACGGCGCGCAGGGCGGCCAGGGAGAGCGAGTGGTCCCCGCCCAGCATCAGGAACGCGTCGTTGC
GTTCCAGGAGCCGGGTCAGGGCGACCGTCGCGGTGTCCATCGCCAGGTCCATCGAGAAGGGGCTGAGGTCGATGTCGCCC
CCGTCGACCACGTCGATCCGGTCGAAGACCCCTGGGCCCCGGTCGATGCCGACGCCGTGGATCAGGCTGGACTCGTGCCG
GATGGCGCGCGGCGCGAACCGCGCGCCGGGCCGGTAGCTGGTGCCTCCGTCGTACGGGGCGCCGACGACCACCACGTCAT
GGCCGATCGGGTCGGGCCGGTGGCGCAGCCGCATGAAGGTCGCCGGTTGGGCGTAGCGCGGGGAGACGGCGGTGGACACC
CTGGCCGTTCCCCGCGCACCCGGCCCTGCTCCCGTTCCCGTACCGACGCCCGGCCACCCCGTGCGGGCTCCcGTTCCCGT
GCCGACCCCCGTTCCCGAACGGGCTCCCGTTCCCGCGTGGAATCCCGTTCCCGCGCCCGCGGCGCCGTCCGGGCCGCGGC
TGCCCCTCCCTCCGAGACCGCTCCTGCCGTTCCTGCGGCCGTTGCCGCTCTGCGGGCCGGTGCCCGCGCCCACGCCCGCT
GCACCGTCCGCGCCGCCGCCGGTGCCGTTGCCGCCGCCGGTGCCGTTCTGGCCACCGGTGCCGTTCTGGCCGCTCATACG
ACCACCCGGCCCTGGAGCCTGAGCCTGCGCACCGCGTCGACGGAGCGCCGCACCGTCTCGCCGAAGTCCACGTCCTCCGG
CGGCACCGTGTCGATGACCACCGCGTCGTACAGGCGCCGTGCCATGGCGCCCTTGACGGCCGTCACCTCGTCGCGCCGGA
TCCCTTCGGCGAGGAGCAGTCCGGTCCACGCGCTGGTGGTGCCGGACCCCTCGTGGATGCCCAGCTTGGGGCGGGCCACG
GTCTCGGCGGGCAGCAGGCCGGAGAGGGCCTGCCGCAACACCCACTTGTCGGTGCCCCGCCGGCGTTTGAGCCCGGGTTC
GAGGGAGACCAGCGCGTCCAGGACCGCGCGGTCCCAGTACGGGTGGGTGGTCCACTTCCCGGCGATGCCCGCGAGGACGG
GGGACATCTCGTTGAGGCCGTCGAAGCCCGCCATGTCGCCCGCGATCTCGTCGTCGAGGGACCAGAGCGAGGCCGTGCGC
CGGTGCATACCGCCGAGCGGGATGTCGGCGCCGTACCCGGTGAGGATGCGGAGCGGCCCGGTGTCGAGCCGCCGGTAGAG
GGCGACGAGCGGCAGCAGGTACTCCAGGACCGTGGGGTCGGTGATCTCCGCGGCGGCGACCGCCCAGGGCAGTTCCCTGA
CGAGTTCGGCCGAGTGGAGCCGGATCTCGCTGTGCGCGGTGCCCAGGTGGACGGCGACCGAGCGGGCCGCGTCGAACTCG
TCGGACACCTCGGTGCCCATCGACACGGACCGTGTCCCGGGTGCCAGGGCCGCCGTGTGGGCGGCGACTCCCCCGGAGTC
GATGCCGCCGGACAGGACGACGGTGGGGGCCGCCTCCCCGCCGCGCAGCCGGGTGCGGACCGCCGTGGCGAGGCGTTCGC
CGACCAGGTCCACCGCCTCCCGTTCGCCGGGCAGCGCCCGGGAGAGCGGGGGTGTCCAGGTGCGGACCGCCCTGGCGGTG
ATGTCGGAGCCGCCGACTCCGTGCAGCAGGAGGGCGGTCCCGGCGGGGACCCGGCAGACGCCCGCCGCCCCCGGCGCGGT
GTGGGTGCCGGACAGGCCCAGCGGCCGGCCCGGCTCGTGCGCCAGGGTCTTCGCCTCGGTGGCGGCGCTCAGCCCCGTCA
CGTCGGCGCGCAGCCACAGCGGTACCGAACCGGCGTGGTCGGTGGCCGCGACGGTCGCGCCGGTGGAGGCGTCGGTGAGC
AGTGCGGCGAACCGTCCGTTCAGGAGCCGGAAGGCCCCGGGGCCCCAGCGCCGCCAGGCGGCCAGCAGCAGTTCGGCGTC
```

-continued

```
GCCGAGGGCGGCAGAGGAGCCGCCGAGCGCTCCGGTCAGCTCGGCGCGGTTGTACAGCTCGCCCGCCAGGAGCAGCCGGA
CCTGGCCGTCGGCGACCAGGACGGGCGGACGGCCCAGGGTCACGGCCGTTCCGCTCCAGAGCGGGTACGCGGTGCCGTCG
TGCACGGGGACATGGGTCCCGCGGACGGCGAAGCGGGGTGCGCTGCCGGGTTCGGAGTGACCGCCGGGGCCGCCGCCGGG
GCGGCCCTCGGTGCCGATGCGCACCCGGAATCCGTACACGAGGTCGGGGCCGGGCATGGTGAACTCGTCCTCCACGGTGG
TCAGATGGCCAGGGCGGCGAAACCGCCGGACTGGAAGTCGTAGGCCACCGGTACCTCGATCAGGAACGGGCGGCCGAGTC
CGGCGCCCTTGGTGAGGGCGGCGAGCAGCGAGGTGCGGTCGGTGGCGCGGACGGCCTCGCAGCCGTTGGCCTCGGCGAGC
TGGACGAAGTCGACGCTTCCGAAGCCGACGGCGGGGGCGTGGGAGCGCTGGTGTCCGAGGTTCTGGTACAGCTCGATCAG
GCCGTTGCGGTCGTTGTTGACGACGACCATGACGATCGGCAGGCCCAGGCGCACGGCCGTCTCGATGTCGGCGCTGTTGG
AGTGGAAGCCGCCGTCGCCCGCGATGAGGAAGACGGGCTCGCCGGGCCGGGCGATCTGGGCGGCCATGGCGGCGGGCAGT
CCGTAGCCGAAGCTGGAGCAGCCCGCGGAGGTGAGGAATCCGTACGGCTGGTCGGACTTGGCGAAGAGCACGCCGTAGTG
GCGGAAGAAGCCGATGTCGCTGACGAAGGTGCCGTTGTCGAGGACGGAGTTCATGCAGTCGATCACCTGGTGGACCCGCA
TGCCGTCCTCGTACTCGGTGGGGTCGGCGAGGAATTCGGCGACGCGGGCGCGCAGGGCGCTGAGGTCGTGCCGGGTCTTG
GGGGCGAGGCCCGAGGTCGCGTCGTCGAGCGCGGTGACGAATTCGGCGACGTTGGTGACGATGTCGATGTCGGCGCGGAA
CAGCTCCGGGATCGGGTTGACCTCGGGGGCGACCCGGACCGTGGTCTTGGCCCGGCCCCGCGTCCACATGGAGGGGCGCA
GGTCCTCGGCGTAGTCGTAGCCGATCGCCAGGAGGAGGTCGGCGGGGCCGAAGATCTCGTCGAGGGCCGGGTGGCCGAGA
ATGCCGTCCATGTAGCCGCTGATGGCGCCGTAGTTGAGCGGGTGGTCGTGCGGCAGGACGCCCTTGGCGGTGTAGGTGGT
GACGACGGGGATGTTCAGCCGCTCGGCGAGGGCGCGCAGGGCGTCGACGGCCCCGGCGCGGATGACGGCGCTACCGACGA
CGAGGAGGGGGTTCTCGGCCTCGCGCACCAGCTCAGCGGCCTCGTCGAGGCGGGCGCGCCAGTCGGCGTCCAGGGCGTGG
GTGGCGGTGGCCCGGACCAGGGGGGCGTCGGTGGGGGTGCCGTTCAGCTCGGCGCCGAGGAGGTCGACCGGCAGGCTGAT
GAAGCTGGGACCCACGGGCTCGATCCGGCTGTTGAGGACGGCGCTGTCGACGAGGTTGACGATGTCCTCGCCGCGTTCGA
GCTGGACGCTGAACTTGGTCAGCGGGCCCATCACGGCGGTGCTGTCCAGGCACTGGTGGGTGACGTTGGGGTAGCAGTCG
TACGACTCGGACTGCGCGGCCAGCGCGATGACCGAGCTGCGGTCCAGGGCGGAGGTGGCGACGCCGGTGGCCAGGTTGGT
CATGCCGGGGCCCAGGGTCGCGAAGCACGCCTGGGGGCGGTTGGTGATCCGGCGAGGACGTCCGCCATCACCCCGGCGG
TGAACTCGTGCCGGGTCAGGACGAAGTCGAGTCCTTCGACCTCGTCGAAGAGAATGGCGGACGCCTCCCGGCCGACGACG
CCGAATACATGGTCGACACCGTACTGGTGAAGACGTTCCAGCATGGCTTTCGCGGTCGTGGTGGCCATGGAGATCTCCTT
CGCATCGGACGGGCGCCGGGATGGCGCCCCGGAAAACGCGGCACCGGGCGGTGCGCACCGGGTGGCGCACACCGTGGGTG
GTGGCGTTGCCACTGTGCGGATCGCCTCTTGGCGGCGGTCGGACGCCCGGCTTGGACAGAATGGGCAAGGCGCGTTCAAG
GCATGGCGTCCATCGTCCTCGTGGCGCTTTTCGTGAAATCCGTCCGGCGCCGACGGTCTCCATCCGATTCCGTCCCCTTC
CGTCCACCGATCCGAGGAGAATCCATGGATGTCCTGGCCGCGTTGGAGCGCAAGCCCAGCCTGAATCTTTTCCCCATCGA
GAACCGGCTGTCGCCGCGCGCCAGTGCCGCGCTGGCCACCGACGCCGTCAACCGCTATCCGTACTCCGAGACCCCGGTGG
CCGTCTACGGCGATGTCACGGGGCTGGCCGAGGTGTACGCGTACTGCGAGGACCTGGCCAAGCGCTTCTTCGGGGCGCGC
CACGCCGGTGTGCAGTTCCTGTCCGGTCTGCACACCATGCACACCGTGCTGACCGCCCTGACCCCGCCCGGCGGGCGCGT
CCTGGTCCTCGCGCCGGAGGACGGCGGCCACTACGCCACGGTGACGATCTGCCGGGGCTTCGGCTACGAGGTCGAGTTCT
TACCTTCGACCGCCGGACACCTGGAGATCGACT
```

SEQ ID NO: 17 cvm cluster

```
GGTACCGGCATCCGACCCAGGCCCCGGGCGCAGGACCCGGAGGCAGGCACCGGCACACCC
CGGCCGGGCGGCCCGGCTCCCGGCGGTCGGTGTCCGGCGACCCGCAATCGGCAGCCGCCC
CAGGCCCGGGACAGGAGCCCGGCTCAAGGCACCGGCCCTGCGCACCCGCTGAGGCGGCAG
GTTCCTGACAGCCGGCATCCGCCAGTCGGCGCGGGGCAGCCGCCCCAGGCGCCCGGCCCG
GCACACCCGTGCGAGCGCCCGGCTCCCGGCGGTCGGTGCCCCGGAGGCGGCGACCGGCAG
```

-continued

```
CCGGACACGGCCCCGCTCGGGGCGCGGCCCAGGGCACAGGCCCTGGGCACCCGCTCGGAC
GCCCGTTCGGACAGCAGGCCCGTGGGAAGCCGCCGGTCAGGCCCGCAGGCAGCCACCGGT
CGGCGGGCGGATCAGGTGTTGGCGGGGGACTCGTCCGGGAAGATCTTTGTGACGACGGTC
CCGTCCTCGGTCAGATAGCCGTGCAGCATCCCGGGGCTGCTGTGCGGCGCGTCGAAGTCG
CCCCGGGGGTCGAGGGCGATCACGCCGCCCTGCCCGCCGAGCCGGGGCAGGCGCTTGACG
ATCACCTCGTAAGCGGCGGACGCCACGCCGAGCCCCTTGAACTCGATCAGATGGGAGAGG
GTCGAGGTCGCCGCGCCCCGGATGAACACCTCACCGGCGCCGGTGGCGCTCGCGGCGACG
GTCCGGTTGTCGGCGTAGGTCCCGGCCCCGATCAGCGGGGAGTCGCCGATCCGGCCGGGG
AGCTTGTTGGTGAGCCCGCCGGTGGAGGTGGCCGCCGCGAGATCGCCGCGCCGGTCGAGG
GCCACCGCGCCCACCGTCCCCGTCGACTGCGCGTCGGCCAGTGCCTCCGGGGCCCTCCGG
GCGGCGGGATCGCCCGCCTCGGTCTCCTTCGCGCGCAGCAGCGCGTCCCAGCGGGCCTGG
GTCCAGTAGTAGTCCTGGGTGACGGTGCGCAGCCCGTGCCGGGCGCCGAAGTCGTCGGCG
CCCTCGCCGGAGAGGAGGACGTGCTTCGACTTCTCCAGCACCAGCCGGGCGCCCTCGACC
GGGTTGCGCAGGGAGGTGACCCCGGCGACCGCTCCCGCCTTCAGATCGGAGCCCCGCATC
ACGGAGGCGTCCAGCTCATGCCCGGCGTCGGCGGTGAAGACGGCGCCCTTGCCCGCGTTG
AACAGCGGGTTGTCCTCCAGTTCGCGGACGGCGGCCTCGACCGCGTCCAGGCTGTCCCCG
CCGCGCGCGAGCACCCGCTGTCCGGCGCGGAGCGCTGCGGCGAGCCCGTCCCGGTACGCC
TTCTCCCGTTCCGGGCCGGTCGTCTCCCGGTCCAGGGCGGCTCCGGCCCCGCCGTGGACG
GCGATGACCACGTCACGGGCGTCCGGCCGGGCTTCCCCGGCGGCGCTCCCCCGTTCCTTC
TTCTCCTCCCGCGCCTGCTGCTCCTGCTTCTGTTGCGTCGTGTGGGCCGCCGCGGTGGGT
CCATGGCCGCCCGAGGCCCCGGGTACGACGATGAGCGTGGTCGTCAGCACCGCGGCGGCG
AGCAGGGAGGACGCCAGCCAGGCGGTGGCGGGGCGGTGGGGCATCGGGCACTCCTCGGGA
CGGGGGTGAGAGACGCTCCGGCCGACTGTACTGACATGCCCATGCCCCCTCTAGTGCCCC
GGAGCCGCCTTCCGCCCTCCCCGCCGCCCGGCGGCGCCCGCCCGGCGCGCTCAGTCCAGG
GCCAGGTCCTCCGGGGCGGAGCGGGCGAGTCCGGCGAGTGTGCCGAGCGCCCGGGTCAGT
TCGTCCGCCGACGGCGACGCCAGGCCCAGCCGGACCGCGTGCGGTGTACGGCCCTGCCCG
GCGCAGAACGCGGCGGCGGGCGTCACCCCGATCCCGTGCCGCGCGGCGGCGGCGACGAAG
GTGTCGGCGCGCCAGGGGCGGGGCAGCACCCACCAGCAGTGGTACGAGCCGGGGTCGCCC
GACACGGCGAAGCCGTCGAGCGCGCGCCGGGCGATCTCCTGCCGTACGCCCGCGTCCCGC
CGCTTGGCGCGTACCAGCGCGTCGACCGTGCCGTCGGTCTGCCAGCGGACCGCCGCCTCC
AGCGCGAACCGCGCGGGGCCGAGACCGCCGGAGCGCAGCGCGGCGCCGACCGCTCCGTCG
AGCCCCGGGGGCACCACCGCGAACCCCAGGGTCAGCCCGGGGGCGAGCCGCTTGGAGAGG
CTGTCGACGAGCACCGTCCGCCCGGGGCGACCGCCGCGAGCGGAGCCGTGCCCTCCCGC
AGGAAGCCCCAGACGGCGTCCTCGACCGCGGGAAGGTCCAGCCGCTCCAGGACCGCGGCG
AGCTGGGCGAGACGCCCGTCCGACAGGGTGAGGGAGAGCGGGTTGTGCAGGGTGGGCTGG
ACATAGACCGCCGGAGCGGAGCGCTCCGGTTGGCCTCGTCCAGCGCCTCCGGAATCACC
CCGTCCGCGTCCATGGCGAGGGGACGAGCGTGATGCCGAGCCGGGCCGCGATCGCCTTG
ACCACGGGGTAGGTCAGCTCCTCGACCCCAGTCGGCCCCCGGCGGCACCAGCGCGCCG
AGCACGGCGGAGAGTGCCTGCCGACCGTTGCCCGCGAACAGCACCCGCCGGGGGTCCGGC
CGCCAGCCGCCCCGGGCGAGCAGCCCGGCGGCGGCCTCGCGCGCCTCGGGGGTCCCGGCG
```

-continued

```
GCACCGGCCGGCCGGAGCACGGACTCCAGGACATCGGGCCGCAGCAGCCCGCCGAGCCCG
GTGGCCAGCAGCGCGGCCTGCTCGGGGACGACGGGGTGGTTCAGCTCCAGGTCGATCCGG
CTTCCGGCGGGCTCGGAGAGCGCGGGGCCGACGCCCGCCCGCGCCGCGCGGACATAGGTG
CCGCGCCCCACCTCGCCGACGGTGAGCCCTCTGCGGGCCAGCTCCCGGTAGACCCGGGCG
GCGGTGGAGTCGGCGATGCCGCACCCGCGGGCGAACTCCCGCTGCGGCGGAAGCCGGTCC
CCGGGGCGCAGCCCGCCCGTCCTGATCTCCTCGGCGACCGCGTCGGCCACCTGCCGGTAG
TCCTTCATCTCCCGTACCTCCCCTGTCCGGTGGACCGCTTCCCGCCCGGCCCCGCCGACC
GTGAAACGGAAGCACCCCGTTCCGGAGCTCGAGCTCCCCGTCCGGAAGCTCCCCGTCCGG
AAGCTCCCCGTTCCAGAATTGCACCGAGAGCAATATTCCCTATTGCACCGATCAAAACAC
CGATCTACGCTCGGAATTGCCTCACACAGACCGTCGACGCATCTGCCGCACACCGGTACT
GACGCCCCGTCGGACCGCACCCGCGCGGAGCCGTCGCCCCGCCCGCCCCGTTCGCGCACA
GGAGAGAGAAGGAGATGGTGGAGACCAGCGCACTCGCCGGTGTGGTGATGGTCGCCCTCG
GAATGGTCCTCACCCCGGGACCGAACATGATCTATCTCGTCTCCCGCAGCATCACCCAGG
GCCGACGTGCGGGATCATCTCGCTGGGCGGTGTGGCCCTCGGTTTTCTGGTCTATCTGC
TCGCCGCGAATCTCGGCCTGTCGGTGATCTTCGTCGCCGTGCCGGAGTTGTATGTCGCGG
TCAAACTGGCCGGTGCGGCCTATCTGGCATATCTCGCCTGGAACGCCCTGCGGCCCGGTG
GCGTGAATGTGTTCTCCCCCGAGGAGGTTCCGCACGACTCCCCGAGCAGGCTGTTCACCA
TGGGGCTGATGACGAACATCCTCAACCCCAAGATCGCCGTCATGTATCTCGCACTCATCC
CGCAGTTCGTCGACCCGAACGCGGACCGTGTCCTGTTCCAGGGGCTGATTCTCGGCGGTC
TCCAGATCGCGGTGAGCGTCGCGGTCAATCTCGCGATCGTGCTGGCGGCCGGAGCCATCG
CCGCCTTTCTCGGCCGCCACCCCTTCTGGCTCAGGGTTCAGCGCCGCGTGATGGGCGCGG
CGCTCGGTACGCTCGCGGTCTCCCTGGCCCTCGACACCTCCGCCCCCGCCGCACCCGTCT
CCTGAGGCCGCCGGACCGGAGCCGACGCGAAGGCACCCCTGGGCAACCGTTCGGAGAGC
TTATCCGTTACCCCATGAATCCCGATATAAGTGCATTGGCCACTTACCCATGCATGGAAC
AGGCCAACCTGACCAAAAAATGAGCCCTCCCCACCCGGAATAGATGCTTCCCAGTGTGAA
GAAATTTCATAGCGGGAGCGTCTGCCGA~CAGGACGGCCCATACGCCGCAAGGCAGAACG
GACATCGCCGCCCGCCCGGGTCCAGAAAATTCGGAGGACACATCGGACGACCGTCTCCGC
ATCGGCGTCAACTCCCGATTACAGAGAATATTGAGTACGTATCAACCGGGCCTTGATCTA
CTCAGCCTCCATTGTTCTCTCCAGTCGGGATGTGCAATGAAGTACGACATAACCCCACCA
TCCGGCCTTCGGTTCGACCTCCTCGGCCCGTTGACCGTGACCGCCGGCGAGCAPCCCGTG
GACCTGGGCGCGCCACGGCAGCGCGCCCTGCTCGCCCTGCTGCTCATCGATGTCGGCAAC
GTGGTCCCGCTGCCGGTCATGACCGCGTCGATCTGGGGGCCGACCCACCGTCCCGGGTC
CGGGGGACGCTCCAGGCTTATGTGTCCCGACTGCGGAAACTCCTGCACCGCCATGACCGT
TCCCTTCGCCTTGTCCACCAGCTCCAGGGGTATCTCCTCGAAGTGGATTCGGCGAAGGTG
GACGCCGTGGTTTTCGAGACACGTGTCAGGGAGTGCCGGGAATTGAGCAGGGCCCGGAAC
CCCGAGGCCACCCGGGCCGTGGCCTGGTCCGCCCTGGAGATGTGGAAGGGCACACCCATG
GGCGAGCTGCATGATTATGAATTTGTGGCGGCGGAGGCCGACCGGCTGGAAGGAATCCGG
TTACGCGCGCTGGAGACCTGGTCCCAGGCGTGTCTCGATCTCCAGCACTATGAAGAGGTT
GCATTTCAGCTCGGCGAGGAGATCCACCGCAATCCGGAACTGGAACGGCTGGGCGGTCTC
TTCATGCGGGCCCAGTATCATTCCGGACGGTCGGCGGAAGCCCTGTTGACGTATGAACGT
```

-continued

```
ATGCGTACCGCGGTGGCGGAGAATCTGGGGGCCGATATCAGTCCGGAGCTCCAGGAACTC
CATGGAAAGATTCTGCGCCAGGAACTCACGGAGACACCCGCCGCGCGATCGACGGCCTCC
CTCACACGGGCGGCGGGCCCGCACGGGCCCCCGCCCCTGGCCGAAACCGGCACCCCCGCC
GCACCCGCGGACATGGCCGAAACCACGGTGGCGGAGGAAAGCGCCGCGCCCCCCGCCCCG
GCGGCGCCCGGGACCCCGCCCCCCATGCCGTCCCCCGTACCGCTCCCCCATCCGTCAGGG
GCCGTCCCGCCGGTCACCCCGGTGCCTCCCCCGGTCCCCCGCTCGGCCCTCCGTTCAGCG
GCACCCGCCGAGACCGAGGACCCGGAACCGGCGCCGCCCCCTCCCCCTCCGCCGGGCGGC
CGACTCATCGGCCGCCGCGCCGAACTGCGCAGGCTGCGGCTGCTGCTGACGAAGACCCGC
GCGGGCCACGGCCATGTCCTGCTGGTCTGCGGCGAACAGGGCATCGGGAAGACCCGGCTC
CTGGAGCACACCGAGCACACCCTGGCCGCGGGCGCGTTCCGGGTGGTCCGTTCGCACTGC
GTCGCCACCCTCCCGGCACCGGGCTACTGGCCCTGGGAGCACCTCGTACGCCAGCTCGAC
CCGGACAGCGGCCTCGGTGACGACGGCGACGCCGACCCCGTCGCCCAGGCCGAGTGGCTG
CCGGAACACCACCTCACCCACCAGATGCGGATCTGCCGGACGGTGCTCGCCGCGGCGCGG
CGGACCCCGCTCCTGTTGATCCTGGAGGATCTGCACCTCGCCCACGCGCCGGTCCTGGAT
GTGCTCCAGCTCCTGGTCAAACAGATCGGCCAGGCCCCCGTCATGGTCGTCGCCACCCTG
CGCGAGCACGATCTCGCCCGGGACCCCGCCGTCCGCCGGGCCGTGGGCCGCATCCTCCAG
GCGGGCAACACCGGCACCCTCCGGCTGGACGGGCTCACCGAGGAGCAGAGCCGGGAGCTG
ATCGTCTCGGTCGCGGGGGCCCCGTTCGCGCCCCATGACGCCCAACGGCTCCAGCGCGCC
TCGGGCGGCAACCCGTTTCTGCTGCTCAGCATGGTCACAGGGGAGGACGGCACCCAGGAG
TGGGCACGGCCGTGCGTCCCGTTCGAGGTGCGCGAGGTGCTGCACGAGCGGCTGAGCGAA
TGCTCCCCGTCCACCCAGGACGTGCTCACGCTCTGCGCCGTGCTCGGCATGAGCGTGCGC
CGACCGCTGCTCACCGACATCATGTCCACGCTCGACATCCCGCACACCGCGCTCGACGAC
GCGCTCGGCACGGGCTGCTGCGCCACGACCGGAACACCGACGGAATGGTCCACTTCGCC
CATGGGCTGACCCGGGACTTCCTGCTCGACGACACCCCGCCGGTCACCCGCGCCCGCTGG
CACCACCGGGTCGCCGCCACCCTCGCCCTGCGCTTCCAGCAGGGCGACGACCACGCCGAG
ATCCGCCGCCACTGTCTGGCCGCGGCCCGTCTGCTCGGCGCCCGCGCGGGGTGCGCCCC
CTGCTGGCGCTGGCCGACCGGGAGCAGTCCCGCTTCTCCCACGCGGAGGCGCTGCGCTGG
CTGGAGAGCGCGGTCGCGGTCGTCGCGGCGCTGCCCCGGGACCAGCCGGTGTCCGCCGTC
GAACTCCAGTTGCGCAAACGGATGATGGCGCTGCACGCGCTGATGGACGGCTATGGATCG
GCCCGCGTCGAGACGTTCCTCTCCCAGGTCACCCAGTGGGAACACGTCTTCGACAACACC
CAGCCCACCGGGCTGCTGCACGTCCAGGCGCTGAGCGCGCTCACCACGGGCCGCCATGAG
CAGGCGGCGGAGCTGGCCGGGCTGCTGCACGAGCTGGCCGACCACGGCGGCGGACCGGAG
GCCCGGTCGGCGGCCTGCTATGTGGACGGCGTCACCCTGTATGTGGGCGGACGGGTCGAC
GAAGCCCTCGCCGCGCTCGCCCAGGGCACCGAGATCACGGACGCCCTCCTGGCCGGACAC
CGCAGGACCGCCGCCCCGCACGGCGGCGGGCACCTCCAGGACCGGCGTATCGACTTCCGC
GCCTATCTGGCGCTCGGCCACTGTCTCAGCGGCGACCGGATTCAGACCCAGCGCTACCGG
ACGGAACTCCTCCACCTCACCCAGTCGGAACGGTACGACCGGCCGTGGGACCGGGCCTTC
GCCCGCTATGTGGACGCGCTCATCGCCGTCACGGAGTGCGATGTCCAGGGGGTGTGGCTG
GCCGCGCGGGCGGGGCTCGACCTCGCCGCCCGCTGCCAGCTCCCGTTCTGGCAGCGGATG
CTCGCCGTCCCCCTCGGCTGGGCCGAGGTCCACCAGGGGGCGCACGACAAGGGGCTGGCC
```

-continued

CGGATGCGGGAGGCGCTGCACGAGGCGGCCCGGCACCGGACCCTGCTGCGCCGTACGCTC

CACCTCGGCCTGCTCGCCGACGCCCTCCAGTACACGGGCGCCCGGGAACAGGCCCGGCGC

ACGATGTCCTCCGCCGTACGGGAGATCGAGCGCCGCGGCGAGTACTTCTGTCTCCGGCCG

CAGTGGCCCTGGGCCCGGCTCCTCOACAGCCACGGCACCTCCGCCGCGGCGGAGCACCGG

GTCGTCCACGGCAGGCACTGACCCGGGGCCGGCCGGAGCCGGGCCCGTACGGTACGGGTC

CGGCTCCGGACCCGGCGGCCCGGAGCCGGGCGGGGCGGGGCGGCCCGACGGTTCCGGGGC

CGGCGGTTGTGGGAGGGGGCGGCCCCCGATCGCTCAGACCGGGCAGACGGCGGACCGCCG

CCCCGCCCGGCCCGAGCCGCCGCCCCCGGCCCAGTGCCCGTAGTCGCCCCGCAGGAAGAC

CAGGGGCGAACCCTCGCGGATCACCCCGAGGTCGCGCACCGCCCCGGTGACGAACCAGTG

GTCGCCCGCCTCCGTCTCCCCCGCCACCTCGCAGTCGAACCACGCGAGCGCGTCGAGCAG

GACGGGGAGCCGGTGGCCGTCGTCCGGTACGGCACCTCCCAGCGCCCCGGATCGCCCCC

GGCGAAACTCCGGCAGACCGGGCCCTGATCCGCGCCGAGCACATTGACGCAGAAACGCCC

GGCCGCCCGGAGCCGCGGCCAGGTCGTCGACGACCTGGCCGGGAGGAAACCCACCAGCAC

CGGATCGAGCGACACCGAGGTGAACGTCCCCACCACCATGGCGGGCGGCGGCTGCCCCGG

AGCCTCGGCCGGACCGGTGACCAGGACCACCCCGGTGGGATAGTGGCCCGCCACCCGGCG

CAGCAGACTCCCGGACACGGACCCGTGGGTGTGCGCGGAAAGGCCCGGAGGCCGGGTCAC

AGCCACGGGTAACGCGCGGTGTCCTTGCCCGCGTAATCGGGGTCCAGATAGACGAAGGCC

CGGTGGACGAGGAAGTCCCGCACCTCGTAGACCGTGCACCAGCGCCCGGCGGCCCACTCG

GGGTCACCCGCCCGCCACGGCCCGTCCCGGTGCTCACCGTGGGTGGTGCCCTCCGCGGCG

AGGAGTTCGGTCCCGGTCAGAATCCAGTTGACGGACCACAGATGGTGGGTGATCGAGCGG

ATGGTGCCCCCGAGGTCGTCGAAGAGCCGGGCGATCTCGGACTTGCCCCGGGCCAGACCC

CACTTGGGGAAGAAGAAGACCGCGTCCTCGGCGAAGTAGTCGATCGCGGGGTGCCGTCG

CTGCCGACGCCGCCGTTGTCGAACGCCTTGAAGTACGCGGTGATGACCGCCTTGCGCTGC

TCGTCCGTCATACCGGCCGATGCCACGGACATGAAACGACCTCCAGAGATTCCGGGTGGC

TGTGCTGGGCTGCGGAAGGGGTGTCCCCCGCGAAGGACGGCGGACGCCGCGGACGCCGC

GGCCGTCTCCCCGGCGGACGGGTCCCAGCGTCCTGGAGAGGGCTTGGCGGCGGCTTGACG

CCGTGCTGTCCCGCGGCTTGCGGAACGCGAAGTACCGGCCAGCGTACGGGCGTTGCACCG

GACGTGTACGCCGGTCGGGACCCCTCGTACCCCCGGAGCCGGCCGACCCCGGCGGCTCCG

GGGGTACGGACGCGCCGGACCGGCCCGAGCGAGCCGGACGGGTCGGACGGTGCGCGTGGT

TCCGGTGTGTCGGACAGCTCGGACGGACCGGACGGTGCGCGTGGTTCCGGTGTGTCGGAC

AGCTCGGACGGGTCGGACGGTGCGCGTGGTTCCGGCACGCCGGACGGGTCAGTTGCCGAT

CATGGCGAGCAATGCCGGGGTGTACCGCTCCCCGGACACCGGGTGGGAGATCGCGGCCGT

CACCTCCGCGAGGGACCGGTCGTCCAGCCGGATCGAGGCGGCGGAGATTGTCCGCGAG

ATGGGCCGGGTTCGCGGTGCCCGGGATCGGGACGACGTCCTCGCCCCGGTGGTGCAGCCA

GGCGAGCGCGAGCTGTGCCAGGGTCAGCCCCAGACCGTCCGCGACCGGGCGCAGCCGGTG

CAGCAACGAGCGGTTGCGCGCGAGGGCCGGAGCGCTGAACCGGGGCTGGCCCCGGCGGAA

GTCCTCGTCCCCAGATCGTCGGTGGTGCGGATGGTGCCGGTGAGAAAACCCCGTCCCAG

AGGGGCGTAAGCGACGATCCCGATCCCCAGCTCCCGGCAGACGGGCACCACCTCGTCCTC

GATCCCGCGCGACCACAGGCTCCACTCGCTCTGCACCGCCGTCACCGGGTGCACCGCGTC

CGCCCGGCGCAGCGTGGCCGCGGAGGGCTCGGAGAGACCGAGCCTGCGGACCTTGCCCTC

-continued

```
GCGCACCAGCTCGGCCACCGCACCCACGGTCTCCTCGATCGGCACCGCCGGGTCCGTCCA
GTGCTGGTAGTACAGGTCGATGCGGTCGGTGCCGAGACGACGCAGGGACCGTTCGCAGGC
CGCGCGGACGTAGGACGGCTCGCCGCACAAGCCCTGGGAGGCGCCGTCGGACGAGCGCAC
CATGCCGAACTTGGTGGCGATCAGCACCTCGTCCCGGCGGCCCGCGACCGCCCGTCCGAG
CAGCTCCTCACCGGCGCCGAGCCCCTGGACGTCGGCGGTGTCCAGCAGGGTGACCCCGGC
GTCGACGGCGGCGCGGATGGTGGCCGTCGCCCGGGCGCGGTCCGGGCGTCCGTAGAAGTC
GGTGGTCGGCAGGC~GCCGAGCCCCTGGGCACTGACCGGAAGGTCCCGCAGGGCGCGGAC
CGGCGGACGCGGAACCGCGGCGGACACGGAACCGGCCGGGGACTCGGGCGGAGAGCGGGA
CATACGGAACCTCCACAGGCGGAGCCGGGAACGGGACGAGGGCGAGGACGGGACGGAACG
AAGGAGAGGACGGGACGGACAGCACGGACGGGACGGACGGAACGGAGTCGGGAACCGGGG
GGGGTGACCGGAACCGGGCCGTCCTTGGCCCTCCCCCGTCCTCCCCGCCATCCGCCGTTC
TCCCCCGTTCCCTCTCCCGTCCTCCAGCCAACACCGCCGCCCTTTCCAAGCGCTTGACAC
GGCACCGACAGCCGCCGCCGGGCGCCCGATGGGGACCCGTGCCCGCCGGTGAGCGGCGGT
GAGCGCCGGTACGGGACCCCACGCGCCGCCGCCCGGGCGCCCGCCAGGGCCCGCGCGGCC
ACCCCGGCCCGCCCCGGCCGGAGCGGCGATCCGGGCCGCTCGCTGCAAGAGGAACATCCA
CAGCCGCACAAGGAGCGCTCCGCACAGTGGGCACCACGTCCGCCCCGTCCCCCACACCGT
GGCCGGTCCCCACCGGACAGCACAGCACCGCACAGCACCACATCGCACGGCACAGCACAG
CACCACCGGCACGAGGAACCAAGGAAAGGAACCACACCACCATGACCTCAGTGGACTGCA
CCGCGTACGGCCCCGAGCTGCGCGCGCTCGCCGCCCGGCTGCCCCGGACCCCCCGGGCCG
ACCTGTACGCCTTCCTGGACGCCGCGCACACAGCCGCCGCCTCGCTCCCCGGCGCCCTCG
CCACCGCGCTGGACACCTTCAACGCCGAGGGCAGCGAGGACGGCCATCTGCTGCTGCGCG
GCCTCCCGGTGGAGGCCGACGCCGACCTCCCCACCACCCCGAGCAGCACCCCGGCGCCCG
AGGACCGCTCCCTGCTGACCATGGAGGCCATGCTCGGACTGGTGGGCCGCCGGCTCGGTC
TGCACACGGGGTACCGGGAGCTGCGCTCGGGCACGGTCTACCACGACGTGTACCCGTCGC
CCGGCGCGCACCACCTGTCCTCGGAGACCTCCGAGACGCTGCTGGAGTTCCACACGGAGA
TGGCCTACCACCGGCTCCAGCCGAACTACGTCATGCTGGCCTGCTCCCGGGCCGACCACG
AGCGCACGGCGGCCACACTCGTCGCCTCGGTCCGCAAGGCGCTGCCCCTGCTGGACGAGA
GGACCCGGGCCCGGCTCCTCGACCGGAGGATGCCCTGCTGCGTGGATGTGGCCTTCCGCG
GCGGGGTGGACGACCCGGGCGCCATCGCCCAGGTCAAACCGCTCTACGGGGACGCGGACG
ATCCCTTCCTCGGGTACGACCGCGAGCTGCTGGCGCCGGAGGACCCCGCGGACAAGGAGG
CCGTCGCCGCCCTGTCCAAGGCGCTCGACGAGGTCACGGAGGCGGTGTATCTGGAGCCCG
GCGATCTGCTGATCGTCGACAACTTCCGCACCACGCACGCGCGGACGCCGTTCTCGCCCC
GCTGGGACGGGAAGGACCGCTGGCTGCACCGCGTCTACATCCGCACCGACCGCAATGGAC
AGCTCTCCGGCGGCGAGCGCGCGGGCGACGTCGTCGCCTTCACACCGCGCGGCTGAGCTC
CCGGGTCCGACACCGCGCGGCTGAACCCACGGTCCGGGGCCCACGGTCCGGCACCGCGCG
GCTGAGCCCCCGGGTCCGGCAGCGGGCGGCTGAACCCCCGCCCCGGGCCACCGCCCGACC
GCCCCCGCGCACCGGACGCGCCCGCCTGTACGGCGGTCCCGCCCGGGCCCGTACACCTGA
AGCGCCCGGCGGACCGCCGCCCCGCCGGGGGACGGACAGAGCCGGGTGCGGGAGGACGTC
CTCCCGCACCCGGCTCCCACCGTTCCGCACCGACCGCACCCGACCGTGCCGCAGGCGCCA
CCGGCACCGCACCGCCCGCGCCGGCAGCCACCACAGGCGCCACGCCGCCCGCACGGTGCC
```

-continued

```
CGCGCTGCTCAGCCCCCGTCCACCGGGCTGTCCAGCAGCCGCCGCAGCGCGCCCCCGATG
AACTCCCGGTCGGCGGCCGACCCCCCGGACCCCGCGAGATGCCCCCACACTCCCGGGATC
ACCTCCAGCGAGGCATACGGCAGCAGATCGGCCACCCGCTTCTCGTCCTCGACGGCGAAA
CACACGTCCAGGGCGCCCGGCAGCACCACGGCCCGCGCCGTGACGGAGGCCAGCGCCGCC
TCGACGCTCCCCCCGGCCCCGGGTGTCGCCCCCACATCCGTGTTCTCCCAGGTGCGCACC
ATGGTGAGCAGATCCGCGGCGCCGGGCCCGGAGAGGAAGACCTGCTCCCAGAAGCCGGTG
AGGTACTCCTCGCGGGTGGCGAAACCCAGCTCCCGGTGGGCACGGCGGGCCCAGAAGGAA
CGCGAGGTCCCCCACCCGGCGAACACCCGGCCCGCCGCCTTCCGCCCCCGCTCCCCGGCG
TCGGCGCTGAGCGCCGCGGCCAGACCGGACAGCAGGACCAGGCTGTGCGGGCTGCTCACC
GGCGCCCCGCAGATCGGGGCGATCCGGCGCACCATCCCCGGATGCGACACGGCCCACTGG
TAGGCGTGGGCCGCGCCCATCGACCAGCCCGTGACCAGGGCCAGTTCCCGTACCCCCAGC
TCCTCGGTGAGCAGCCGGTGCTGCGCCGCGACATTGTCCTGCGGAGTGATCAGCGGAAAG
CGGGACCCCGACGGGTGGTTGCCGGGCGAGCTGGAGACCCCGTTGCCGAAGAGTCCGGCG
GTGACGACGCAGTACCGCCGGGTGTCCAGCGGCAGCCCCGCACCGATCAGCCAGTCGTAC
CCGGTGTGGTCCCGGCCGAAGAACGACGGACAGAGCACCACGTTCGTCCCGTCGGCGTTC
GGCGTGCCGTACATGGCGTAACCGATCCGGGCGTCCCGCAGGACCTCCCCGTCCAGCAAC
GGCAGTTCGTCGATCTCGAATATGCGGCATTCCACCGCTGACCTCCTTGTTCGATCCCCC
CGGACAACAGGTCGGTCGTGGCCGGAGACTCAGAGCCAGTTGGGGGCGATCTCGGTGGCC
CACAGCTCCAGGcTGCGCAGCTGGACATCGTGCGGGATCAGCCCGGAGTACTGGCACTGG
AGCAGATACTCCGGATCGTGCCGCTCCACCAGCTTCTCGATCATGCGGTTGATGTCGTCC
GGGGTGCCGACCCACTCCAGCCCCGGTCGACCAGGGTCTTGTAGTCCGAGCCGATCGGA
CCCGTCTCGCCGGTCGCGCGCAGCGCCTCGGTGAAGCCCATGGGGCCGAACCAGTTCTCG
AAGATGAAGCCGCCGCCGCGGGACGCCCAGTGGTGGGCCTCGCCGGAGTCCCGGGAGACC
AGGACGTCCTTCATCACCCCGACCCGCTCGCCCCGCCGCAGGGTGCCGTGGCCCGCCGCC
TCGGCCTCCTCCCGGTAGATGTCCATCAGCCGGGCGACGATCTGGTCGTCGGTGTTCATC
AGGATCGGCACCACGCCCTCCCGGGCACAGAACCGGAACGTGTCCTCACTGAAGCTGAAC
GGCTGGAAGACGGGCGGTGGGGCGCTGGTAGGGCTTGGGCGCGATGCCCACCTCGCGG
ATGACGCCGTTCTCGTCGAGGCCCCGGCCGTAGCGGCGCACCGCCTCGTAGGGGAACTCC
AGGTCCGGCACCGGGATCGTCCACTGCTCCCCGGAGTGGGTGAACGTCTCGGTCGTCCAC
GCCTTCTTGATGATCTCCCAGTGCTCCTCGAAGAGGGCACGATTGCGCCGGTCCCGCTCC
CCGGCGTCGGACAGGGTGCCGCCGACCCCGTACACCTGCCCCATGATGTCGGCCCAGCGC
TTCTGGAACCCGCGCGCGATCCCGACGAAGGCGCGGCCCCGGGTCATGTGGTCGAGCATC
GCCAGATCCTCGGCCAGCCGCAGCGGATTGTGCAGCGGCAGGACGTTGGCCATCTGGCCG
ACCCGGATGTGCCGGGTCTGCATGCCGAGGTAGAGCCCCAGCATGATCGGGTTGTTGGAG
ACCTCGAAACCCTCGGTGTGGAAGTGGTGCTCGGTGAAGGACAGTCCCCAGTAGCCGAGT
TCGTCGGCCGCCTGCGCCTGCCGGGTGAGCTGCCGGAGCATGTTCTGGTAGTTCTGCGGA
TTGACCCCCGCCATACCCCGCTGGACCTGCGCATGACTGCCGACCGTTGGCAGATAGAAG
AGAATGGACTTCACCCTGGCTCCTCCGGTTCGCGGCGCCCTCCATTGACGTGCGCCGAAA
GCGGCTCGACCGTCCCACTCCGCCCTTGAGTTCCGTCTGACGCCGCGCCAGTCGGCGGGC
CGTCCGCCGGGGTGCCCGCCGGGGTCCGCACCCGCCGGACGGCACGGCGCGCACCGCGCG
```

```
-continued
CGCGGCGCTTCGGGGCACCGGGCTCGACGGGGTGCTCAGCGGGACGTCCAACGGAAGGCA

AGCCCCCGTACCCAGCCTGGTCAAGGCGCTCATCGCCATTCCCTGAGGAGGTCCCGCCTT

GACCACAGCAATCTCCGCGCTCCCGACCGTGCCCGGCTCCGGACTCGAAGCACTGGACCG

TGCCACCCTCATCCACCCCACCCTCTCCGGAAACACCGCGGAACGGATCGTGCTGACCTC

GGGGTCCGGCAGCCGGGTCCGCGACACCGACGGCCGGGAGTACCTGGACGCGAGCGCCGT

CCTCGGGGTGACCCAGGTGGGCCACGCCGGGCCGAGCTGGCCCGGGTCGCGGCCGAGCA

GATGGCCCGGCTGGAGTACTTCCACACCTGGGGACGATCAGCAACGACCGGGCGGTGGA

GCTGGCGGCACGGCTGGTGGGGCTGAGCCCGGAGCCGCTGACCCGCGTCTACTTCACCAG

CGGCGGGGCCGAGGGCAACGAGATCGCCCTGCGGATGGCCCGGCTCTACCACCACCGGCG

CGGGGAGTCCGCCCGTACCTGGATACTCTCCCGCCGGTCGGCCTACCACGGCGTCGGATA

CGGCAGCGGCGGCGTCACCGGCTTCCCCGCCTACCACCAGGGCTTCGGCCCCTCCCTCCC

GGACGTCGACTTCCTGACCCCGCCGCAGCCCTACCGCCGGGAGCTGTTCGCCGGTTCCGA

CGTCACCGACTTCTGCCTCGCCGAACTGCGCGAGACCATCGACCGGATCGGCCCGGAGCG

GATCGCGGCGATGATCGGCGAGCCGATCATGGGCGCGGTCGGCGCCGCGGCCCCGCCCGC

CGACTACTGGCCCCGGGTCGCCGAGCTGCTGCACTCCTACGGCATCCTGCTGATCTCCGA

CGAGGTGATCACGGGGTACGGGCGCACCGGGCACTGGTTCGCCGCCGACCACTTCGGCGT

GGTCCCGGACATCATGGTCACCGCCAAGGGCATCACCTCGGGGTATGTGCCGCACGGCGC

CGTCCTGACCACCGAGGCCGTCGCCGACGAGGTCGTCGGCGACCAGGGCTTCCCGGCGGG

CTTCACCTACAGCGGCCATGCCACGGCCTGCGCGGTGGCCCTGGCCAACCTGGACATCAT

CGAGCGCGAGAATCTGCTCGACAACGCCAGCACCGTCGGCGCCTACCTGGGCAAACGCCT

GGCCGAGCTGAGCGATCTGCCGATCGTCGGGGACGTCCGGCAGACCGGTCTGATGCTCGG

TGTCGAACTGGTCGCCGACCGCGGAACCCGGGAGCCGCTGCCGGGCGCCGCCGTCGCCGA

GGCCCTGCGCGAGCGGGCGGGCATCCTGCTGCGCGCCAACGGCAACGCCCTCATCGTCAA

CCCCCCGCTGATCTTCACCCAGGAAGACGCCGACGAACTCGTGGCGGGCCTGCGCTCCGT

ACTCGCCCGCACCAGGCCGGACGGCCGGGTGCTCTGACCCCTTTGGCCCTCCCCGGCCCC

ACCGGGCACCACCCCGCCGCACCCCGAGCGCAAAAAGACCCCTCTGCCTGCGTTTCCGC

AGGTCAGAGGGGTCTGGTGCAGTGGAGCCTAGGGGAGTCGAACCCCTGACATCTGCCATG

CAAAGACAGCGCTCTACCAACTGAGCTAAGGCCCCGAAGCGACAGAACGGCCCTGGACTG

CTCCGTCCCGGCCACTGCCGCAGACCAGAGTACCGGGTGTTCCCGGTGATCCTCCAAAAC

ATTGAGGTCTCCCGGTGGGCGACCACTCTCCGTAAGATGCTCGACGTGGTTCGCAGCAGC

GAAGCCCGCTTGGGGAAGCGATGGGGAGACGCGCATGGACGCCGCTCAGCAGGAGACGAC

CGCAAGAGCCCGGGAGCTACAGCGAAGCTGGTACGGGAGCCCCTGGGGGCCCTGTTCCG

CAGGCTGATAGACGATCTGGGGCTGAACCAGGCGCGTCTCGCGGCGGTGCTGGGCCTCTC

CGCCCCCATGCTCTCCCAGCTCATGAGCGGCCAGCGGGCCAAGATCGGCAACCCGGCCGT

GGTCCAACGGGTCCAGGCGCTCCAGGAGTTGGCCGGACAGGTGGCCGACGGCAGCGTCAG

CGCGGTGGAGGCCACCGACCGCATGGAGGAGATCAAGAAGTCGCAGGGAGGCTCCGTCCT

GACCGCGAACAGCCAGACCACCAACAGCTCGGGGCGCCGACCGTCCGCCGGGTCGTCCG

GGAGATCCAGTCGCTGCTGCGGTCCGTGTCCGCCGCGGGGACATCATCGACGCGGCGAA

CTCCCTCGCCCCGACCCATCCGGAGCTGGCAGAGTTCCTGCGGGTGTACGGGGCCGGGCG

CACCGCGGACGCCGTGGCGCACTACGAGTCCCACCAGAGCTGACGACCGAGGCCGGCCCC
```

-continued

GGAACGGACCAGAGCCTCATGAGGGACGGGGAGCGGACGCGGCACCATGGGTGAGGTCTT

CGCCGGCCGGTACGAGCTGGTCGACCCGATCGGACGCGGAGGGGTCGGCGCGGTCTGGCG

CGCCTGGGACCACCGGCGCCGCCGCTATGTGGCGGCCAAGGTGCTCCAGCAGAGCGACGC

GCACACCCTGCTGCGCTTCGTCCGCGAGCAGGCCCTGCGGATCGACCATCCCCATGTCCT

GGCCCCGGCGAGCTGGGCCGCGGACGACGACAAAGTCCTCTTCACCATGGATCTCGTGGG

CGGCGGATCACTCGCGCACGTGATCGGCGACTACGGCCCGCTCCCGCCGCGCTATGTGTG

CGCCCTGCTGGACCAACTCCTCTCCGGGCTCGCCGCGGTGCACGCCGAGGGCGTGGTGCA

CCGCGACATCAAACCGGCGAACATCCTGATGGAGGCCACCGGGACGGGCCGCCCCCCATCT

GCGCCTGTCCGACTTCGGCATCTCCATGCGCAAGGGCGAGCCCCGGCTGACCGAGACCAA

CTATGTCGTGGGTACGCCCGGTTACTTCGCCCCCGAGCAGGTCGAGGGCGCGGAGCCGGA

CTTCCCCGCCGATCTCTTCGCCGTCGGCCTGGTCGCCCTCTATCTGCTGGAGGGTCAGAA

ACCCGACACCAAGGCCCTGGTGGACTTCTTCACCGCCCATGGCACCCCCGGTGCTCCCCG

GGGGATACCGGAGCCGCTGTGGCAGGTGCTCGCGGGGCTGATCCAGCCCGACCCCGCCGC

CCGGTTCCGTACGGCGACGGGGGCCCGGAAGGCCCTCGCCGCCGCCGTGGAACTGCTTCC

CGAGAGCGGCCCCGACGACGAACCGGTGGAGATATTCGACCAACTGGGCCCGCTGCCGCC

GGGGTTCGGCCCCGGCGGCCCCGAGAACACGCCGCCCTCCGGTCTGCTGCGCTCGGCGGC

CTCCGGTACC

SEQ ID NO: 18 orf2par reverse complement

ATGGCCACCACGACCGCGAAAGCCATGCTGGAACGTCTTCACCAGTACGGTGTCGACCATGTATTCGGCGTCGTCG

GCCGGGAGGCGTCCGCCATTCTCTTCGACGAGGTCGAAGGACTCGACTTCGTCCTGACCCGGCACGAGTTCACCGC

CGGGGTGATGGCGGACGTCCTCGCCCGGATCACCAACCGCCCCCAGGCGTGCTTCGCGACCCTGGGCCCCGGCATG

ACCAACCTGGCCACCGGCGTCGCCCACCTCCGCCCTGGACCGCAGCTCGGTCATCGCGCTGGCCGCGCAGTCCGAGT

CGTACGACTGCTACCCCAACGTCACCCACCAGTGCCTGGACAGCACCGCCGTGATGGGCCCGCTGACCAAGTTCAG

CGTCCAGCTCGAACGCGGCGAGGACATCGTCAACCTCGTCGACAGCGCCGTCCTCAACAGCCGGATCGAGCCCGTG

GGTCCCAGCTTCATCAGCCTGCCGGTCGACCTCCTCGGCGCCGAGCTGAACGGCACCCCCACCGACGCCCCCCTGG

TCCGGGCCACCGCCACCCACGCCCTGGACGCCGACTGGCGCGCCCGCCTCGACGAGGCCGCTGAGCTGGTGCGCGA

GGCCGAGAACCCCCTCCTCGTCGTCGGTAGCGCCGTCATCCGCGCCGGGGCCGTCGACGCCCTGCGCGCCCTCGCC

GAGCGGCTGAACATCCCCGTCGTCACCACCTACACCGCCAAGGGCGTCCTGCCGCACGACCACCCGCTCAACTACG

GCGCCATCAGCGGCTACATGGACGGCATTCTCGGCCACCCGGCCCTCGACGAGATCTTCGGCCCCGCCGACCTCCT

CCTGGCGATCGGCTACGACTACGCCGAGGACCTGCGCCCCTCCATGTGGACGCGGGGCCGGGCCAAGACCACGGTC

CGGGTCGCCCCCGAGGTCAACCCCGATCCCGGAGCTGTTCCGCGCCGACATCGACATCGTCACCAACGTCGCCGAAT

TCGTCACCGCGCTCGACGACGCGACCTCGGGCCTCGCCCCAAGACCCGGCACGACCTCAGCGCCCTGCGCGCCCG

CGTCGCCGAATTCCTCGCCGACCCCACCGAGTACGAGGACGGCATGCGGGTCCACCAGGTGATCGACTGCATGAAC

TCCGTCCTCGACAACGGCACCTTCGTCAGCGACATCGGCTTCTTCCGCCACTACGGCGTGCTCTTCGCCAAGTCCG

ACCAGCCGTACGGATTCCTCACCTCCGCGGGCTGCTCCAGCTTCGGCTACGGACTGCCCGCCGCCATGGCCGCCCA

GATCGCCCGGCCCGGCGAGCCCGTCTTCCTCATCGCGGGCGACGGCGGCTTCCACTCCAACAGCGCCGACATCGAG

ACGGCCGTGCGCCTGGGCCTGCCGATCGTCATGGTCGTCGTCAACAACGACCGCAACGGCCTGATCGAGCTGTACC

AGAACCTCGGACACCAGCGCTCCCACGCCCCCGCCGTCGGCTTCGGAAGCGTCGACTTCGTCCAGCTCGCCGAGGC

CAACGGCTGCGAGGCCGTCCGCGCCACCGACCGCACCTCGCTGCTCGCCGCCCTCACCAAGGGCGCCGGACTCGGC

CGCCCGTTCCTGATCGAGGTACCGGTGGCCTACGACTTCCAGTCCGGCGGTTTCGCCGCCCTGGCCATCTGA

-continued

SEQ ID NO: 19 orf3par reverse complement

ATGCCCGGCCCCGACCTCGTGTACGGATTCCGGGTGCGCATCGGCACCGAGGGCCGCCCCGGCGGCGGCCCCGGCG

GTCACTCCGAACCCGGCAGCGCACCCCGCTTCGCCGTCCGCGGGACCCATGTCCCCGTGCACGACGGCACCGCGTA

CCCGCTCTGGAGCGGAACGGCCGTGACCCTGGGCCGTCCGCCCGTCCTGGTCGCCGACGGCCAGGTCCGGCTGCTC

CTGGCGGGCGAGCTGTACAACCGCGCCGAGCTGACCGGAGCGCTCGGCGGCTCCTCTGCCGCCCTCGGCGACGCCG

AACTGCTGCTGGCCGCCTGGCGGCGCTGGGGCCCCGGGGCCTTCCGGCTCCTGAACGGACGGTTCGCCGCACTGCT

CACCGACGCCTCCACCGGCGCGACCGTCGCGGCCACCGACCACGCCGGTTCGGTACCGCTGTGGCTGCGCGCCGAC

GTGACGGGGCTGAGCGCCGCCACCGAGGCGAAGACCCTGGCGCACGAGCCGGGCCGGCCGCTGGGCCTGTCCGGCA

CCCACACCCGCCGGGGCGGCGGGCGTCTGCCGGGTCCCCGCCGGGACCGCCCTCCTGCTGCACGGAGTCGGcGGC

TCCGACATCACCGCCAGGGCGGTCCGCACCTGGACACCCCCGCTCTCCCGGGCGCTGCCCGGCGAACGGGAGGCGG

TGGACCTGGTCGGCGAACGCCTCGCCACGGCGGTCCGCACCCGGCTGCGCGGCGGGGAGGCGGCCCCCACCGTCGT

CCTGTCCGGCGGCATCGACTCCGGGGGAGTCGCCGCCCACACGCGGCCCTGGCACCCGGGACACGGTCCGTGTCG

ATGGGCACCGAGGTGTCCGACGAGTTCGACGCGGCCCGCTCGGTCGCCGTCCACCTGGGCACCGCGCACAGCGAGA

TCCGGCTCCACTCGGCCGAACTCGTCAGGGAACTGCCCTGGGCGGTCGCCGCCGCGGAGATCACCGACCCCACGGT

CCTGGAGTACCTGCTGCCGCTCGTCGCCCTCTACCGGCGGCTCGACACCGGGCCGCTCCGCATCCTCACCGGGTAC

GGCGCCGACATCCCGCTCGGCGGTATGCACCGGCGCACGGCCTCGCTCTGGTCCCTCGACGACGAGATCGCGGGCG

ACATGGCGGGCTTCGACGGCCTCAACGAGATGTCCCCCGTCCTCGCGGGCATCGCCGGGAAGTGGACCACCCACCC

GTACTGGGACCGCGCGGTCCTGGACGCGCTGGTCTCCCTCGAACCCGGGCTCAAACGCCGGCGGGGCACCGACAAG

TGGGTGTTGCGGCAGGCCCTCTCCGGCCTGCTGCCCGCCGAGACCGTGGCCCGCCCCAAGCTGGGCATCCACGAGG

GGTCCGGCACCACCAGCGCGTGGACCGGACTGCTCCTCGCCGAAGGGATCCGGCGCGACGAGGTGACGGCCGTCAA

GGGCGCCATGGCACGGCGCCTGTACGACGCGGTGGTCATCGACACGGTGCCGCCGGAGGACGTGGACTTCGGCGAG

ACGGTGCGGCGCTCCGTCGACGCGGTGCGCAGGCTCAGGCTCCAGGGCCGGGTGGTCGTATGA

SEQ ID NO:20 orf4par reverse complement

GTGTCCACCGCCGTCTCCCCGCGCTACGCCCAACCGGCGACCTTCATGCGGCTGCGCCACCGGCCCGACCCGATCG

GCCATGACGTGGTGGTCGTCGGCGCCCCGTACGACGGAGGCACCAGCTACCGGCCCGGCGCGCGGTTCGCGCCGCG

CGCCATCCGGCACGAGTCCAGCCTGATCCACGGCGTCGGCATCGACCGGGGCCCAGGGGTCTTCGACCGGATCGAC

GTGGTCGACGGGGGCGACATCGACCTCAGCCCCTTCTCGATGGACCTGGCGATGGACACCGCGACGGTCGCCCTGA

CCCGGCTCCTGGAACGCAACGACGCGTTCCTGATGCTGGGCGGGACCACTCGCTCTCCCTGGCCGCCCTGCGCGC

CGTGCACGCCCGCCACGGCCGGGTCGCCGTCCTGCACCTGGACGCGCACAGCGACACCAACCCACCCGTCTACGGC

GGCACCTACCACCACGGCACCCCCTTCCGCTGGGCCATCGAAGAGGGCCTGGTGGACCCGGAGCGCCTGGTCCAGG

TCGGCATCCGCGGCCACAATCCGCGGCCCGACTCCCTGGACTACGCGCGCGGGCACGGCGTCAGCATCGTCACCGC

CGCCGACTTCACCCGGCGCTCACCGCGCGGCATCGCCGAGCAGATCCGGCGCACCGTCGGCGGCcTGCCGCTGTAC

GTCTCCGTCGACATCGACGTCGTCGACCCGGCGTACGCCCCGGGCACCGGCACACCGGCCCCGGCGGGCTGTCCT

CGCGCGAGGTGCTGACCCTGCTCGACGTGGTCGGGCAGCTCAGGCCCGTCGGGTTCGACGTGGTCGAGGTGTCCCC

GGCGTACGACCCGTCGGGGATCACCTCCCTGCTGGCGGCGGAGATCGGGGCCGAACTGCTCTACCAGTACGCCCGC

GCCACCACGTCGCCCGCGTCGGCACCGGTGGACTCTCCCCTGCCACCGGGGCGGCGGCGGACGACGCCGAGAACG

CCGAGAACGCGGTGGACGCGGTGGACGCCGAGAGCGCCGTGGACTTCGCCGGGCAGCGGTGGGGGTAG

SEQ ID NO:21 cvm6 Polypeptide

VPGSGLEALDRATLIHPTLSGNTAERIVLTSGSGSRVRDTDGREYLDASAVLGVTQVGHGRAELARVAAEQMARLEY

FHTWGTISNDRAVELAARLVGLSPEPLTRVYFTSGGAEGNEIALRMARLYHHRRGESARTWILSRRSAYHGVGYGSG

-continued

GVTGFPAYHQGFGPSLPDVDFLTPPQPYRRELFAGSDVTDFCLAELRETIDRIGPERIAAMIGEPIMGAVGAAAPPA

DYWPRVAELLHSYGILLISDEVITGYGRTGHWFAADHFGVVPDIMVTAKGITSGYVPHGAVLTTEAVADEVVGDQGF

PAGFTYSGHATACAVALANLDIIERENLLDNASTVGAYLGKRLAELSDLPIVGDVRQTGLMLGVELVARGTREPLPG

AAVAEALRERAGILLRANGNALIVNPPLIFTQEDADELVAGLRSVLARTRPDGRVL

SEQ ID NO:22 cvm3 Polypeptide

VTRPPGLSAHTHGSVSGSLLRRVAGHYPTGVVLVTGPAEAPGQPPPANVVGTFTSVSLDPVLVGFLPARSSTTWPR

LRAAGRFCVNVLGADQGPVCRSFAGGDPGRWEVPYRTTATGSPVLLDALAWFDCEVAGETEAGDHWFVTGAVRDLG

VIREGS PLGVFLRGDYGHWAGGGGSGRAGRRSAVCPV

SEQ ID NO:23 orf6par Polypeptide

MRASSPRGFRVHHGHAGIRGSHADLAVIASDVPAAVGAVFTRSRFAAPSVLLSRDAVADGIARGVVVLSGNANAGT

GPRGYEDAAEVRHLVAGIVDCDERDVLIASTGPVGERYPMSRVRAHLRAVRGPLPGADFDGAAAAVLGTAGARPTI

RPARCGDATLIGVAKGPGTGPAEQDDRSTLAFFCTDAQVSPVVLDDIFRRVADRAFHGLGFGADASTGDTAAVLAN

GLAGRVDLVAFEQVLGALALDLVRDVVRDSGCGGALVTVRVTGAHDTEQAGRVGRAVVDAPSLRAAVHGPAPDWAP

VAAVAGGHGDEGPGRSPGRITIRVGGREVFPAPRDRARPDAVTAYPHGGEVTVHIDLGVPGRAPGAFTVHGCDLLA

GYPRLGAGRAV.

SEQ ID NO:24 orf4par Polypeptide

VSTAVSPRYAQPATFMRLRHRPDPIGHDVVVVGAPYDGGTSYRPGARFAPRAIRHESSLIHGVGIDRGPGVFDRID

VVDGGDIDLSPFSMDLAMDTATVALTRLLERNDAFLMLGGDHSLSLAALRAVHARHGRVAVLHLDAHSDTNPPVYG

GTYHHGTPFRWAIEEGLVDPERLVQVGIRGHNPRPDSLDYARGHGVSIVTAADFTRRSPRGIAEQIRRTVGGLPLY

VSVDIDVVDPAYAPGTGTPAPGGLSSREVLTLLDVVGQLRPVGFDVVEVSPAYDPSGITSLLAAEIGAELLYQYAR

ATTSPASAPVDSPLPPGAAADDAENAENAVDAVDAESAVDFAGQRWG.

SEQ ID NO:25 orf3par Polypeptide

MPGPDLVYGFRVRIGTEGRPGGGPGGHSEPGSAPRFAVRGTHVPVHDGTAYPLWSGTAVTLGRPPVLVADGQVRLL

LAGELYNRAELTGALGGSSAALGDAELLLAAWRRWGFGAFRLLNGRFAALLTDASTGATVAATDHAGSVPLWLRAD

VTGLSAATEAKTLAHEPGRPLGLSGTHTAPGAAGVCRVPAGTALLLHGVGGSDITARAVRTWTPPLSRALPGEREA

VDLVGERLATAVRTRLRGGEAAPTVVLSGGIDSGGVAAHTAALAPGTRSVSMGTEVSDEFDAARSVAVHLGTAHSE

IRLHSAELVRELPWAVAAAEITDPTVLEYLLPLVALYRRLDTGPLRILTGYGADIPLGGMHRRTASLWSLDDEIAG

DMAGFDGLNEMSPVLAGIAGKWTTHPYWDRAVLDALVSLEPGLKRRRGTDKWVLRQALSGLLPAETVARPKLGIHE

GSGTTSAWTGLLLAEGIRRDEVTAVKGAMARRLYDAVVIDTVPPEDVDFGETVRRSVDAVRRLRLQGRVVV.

SEQ ID NO:26 orf2par Polypeptide

MATTTAKAMLERLHQYGVDHVFGVVGREASAILFDEVEGLDFVLTRHEFTAGVMADVLARITNRPQACFATLGPGM

TNLATGVATSALDRSSVIALAAQSESYDCYPNVTHQCLDSTAVMGPLTKFSVQLERGEDIVNLVDSAVLNSRIEPV

GPSFISLPVDLLGAELNGTPTDAPLVRATATHALDADWRARLDEAAELVREAENPLLVVGSAVIRAGAVDALRALA

ERLNIPVVTTYTAKGVLPHDHPLNYGAISGYMDGILGHPALDEIFGPADLLLAIGYDYAEDLRPSMWTRGRAKTTV

RVAPEVNPIPELFRADIDIVTNVAEFVTALDDATSGLAPKTRHDLSALRARVAEFLADPTEYEDGMRVHQVIDCMN

SVLDNGTFVSDIGFFRHYGVLFAKSDQPYGFLTSAGCSSFGYGLPAAMAAQIARFGEPVFLIAGDGGFHSNSADIE

TAVRLGLPIVMVVVNNDRNGLIELYQNLGHQRSHAPAVGFGSVDFVQLAEANGCEAVRATDRTSLLAALTKGAGLG

RPFLIEVPVAYDFQSGGFAALAI

The invention claimed is:

1. An isolated *S. clavuligerus* microorganism comprising DNA from which SEQ ID NO:1 has been disrupted or deleted such that the production of 5S clavams by said *S. clavuligerus* is reduced and clavulanic acid production is at least maintained when compared with a *S. clavuligerus* comprising SEQ ID NO:1 which has not been disrupted or deleted.

2. An isolated *S. clavuligerus* microorganism comprising DNA from which SEQ ID NO:1 and one or more of: SEQ ID NO:5, SEQ ID NO:7, SEQ ID NO:10, and SEQ ID NO:11 have been disrupted or deleted such that the production of 5S clavams by said *S. clavuligerus* is reduced and clavulanic acid production is at least maintained when compared with a *S. clavuligerus* which has not had said open reading frames disrupted or deleted.

* * * * *

UNITED STATES PATENT AND TRADEMARK OFFICE
CERTIFICATE OF CORRECTION

| | | |
|---|---|---|
| PATENT NO. | : 7,622,302 B1 | |
| APPLICATION NO. | : 10/552571 | |
| DATED | : November 24, 2009 | |
| INVENTOR(S) | : Barton et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 468 days.

Signed and Sealed this
Eleventh Day of January, 2011

David J. Kappos
*Director of the United States Patent and Trademark Office*